(12) United States Patent
Puzas

(10) Patent No.: US 7,241,732 B2
(45) Date of Patent: Jul. 10, 2007

(54) COMPOSITIONS AND METHODS INVOLVED IN BONE GROWTH

(75) Inventor: J. Edward Puzas, Pittsford, NY (US)

(73) Assignee: University of Rochester, Rochester, NY (US)

( * ) Notice: Subject to any disclaimer, the term of this patent is extended or adjusted under 35 U.S.C. 154(b) by 81 days.

(21) Appl. No.: 10/490,064

(22) PCT Filed: Sep. 20, 2002

(86) PCT No.: PCT/US02/30093

§ 371 (c)(1),
(2), (4) Date: Mar. 19, 2004

(87) PCT Pub. No.: WO03/024408

PCT Pub. Date: Mar. 27, 2003

(65) Prior Publication Data

US 2005/0112168 A1 May 26, 2005

Related U.S. Application Data

(60) Provisional application No. 60/323,987, filed on Sep. 20, 2001.

(51) Int. Cl.
*C07K 14/00* (2006.01)
(52) U.S. Cl. .......................... 514/2; 530/350; 530/351
(58) Field of Classification Search .................... 514/2; 530/350, 351
See application file for complete search history.

(56) References Cited

OTHER PUBLICATIONS

Pun et al. Aug. 2000; Anabolic effects of basic fibroblast growth factor in tibial diaphysis of ovariectomized rats. Bone. 27(2): 197-202.*
Hagihara et al. 2000; Glypican-4 is an FGF2-binding heparin sulfate proteoglycan expressed in neural precursor cells. Developmental Dynamics. 219: 353-367.*
Dunstan et al. 1999; Systemic administration of acidic fibroblast growth factor (FGF-1) prevents bone loss and increases new bone formation in ovariectomized rats. J. Bone and Mineral Research. 14(6): 953-959.*
Chikazu et al. Oct. 6, 2000: Fibroblast growth factor (FGF)-2 directly stimulates mature osteoclast function through activation of FGF receptor 1 and p42/p44 MAP kinase. J. Biol. Chem. 275(40): 31444-31450.*
Mancilla et al. 1998; Effects of fibroblast growth factor-2 on longitudinal bone growth. Endocrinology. 139(6): 2900-2904.*
Sheu et al. 2003; A phage displat technique identifies a novel regulator of cell differentiation. J. Biol. Chem. 278(1): 438-443.*
Marie et al. 1990 ; Effects of epidermal growth factor on bone formation and resoption in vivo. Endocrinol. Metab. 21: E275-E281.*
Canalis et al. 1979 ; Effects of epidermal growth factor on bone formation in vitro. Endocrinology 104(4): 862-869.*

Bradford et al. Feb., 2000; The effect of bone morphogenetic protein-7 on the expression of type I inositol 1, 4, 5-triphophate receptor in G292 osteosarcoma cells and primaty osteoblast cutures. Archives of Oral Biology 45(2): 159-166.*
Abe et al., Etidronate inhibits human osteoblast apoptosis by inhibition of pro-apoptotic factor(s) produced by activated T cells. J Lab Clin Med. Nov. 2000;136(5):344-54.
Al Kawas et al., Immunolocalization of the cation-independent mannose 6-phosphate receptor and cathepsin B in the enamel organ and alveolar bone of the rat incisor. Calcif Tissue Int. Sep. 1996;59(3):192-9.
Artmann et al., Micropipette aspiration of human erythrocytes induces echinocytes via membrane phospholipid translocation. Biophys J. Mar. 1997;72(3):1434-41.
Ash et al. (1980) Giant lysosomes, a cytoplasmic marker in osteoclasts of beige mice. Journal of Pathology. 130:237-45.
Barancik et al., Inhibition of the cardiac p38-MAPK pathway by SB203580 delays ischemic cell death. J Cardiovasc Pharmacol. Mar. 2000;35(3):474-83.
Baron (1989) Molecular mechanisms of bone resorption by the osteoclast. Anatomical Record. 224:317-24.
Baron et al. (1986) Kinetic and cytochemical indentification of osteoclast precursors and their differentiation into multinucleated osteoclasts. American Journal of Pathology. 122:363-78.
Baron et al., Polarized secretion of lysosomal enzymes: co-distribution of cation-independent mannose-6-phosphate receptors and lysosomal enzymes along the osteoclast exocytic pathway. J Cell Biol. Jun. 1988;106(6):1863-72.
Baron et al., Selective Internalization Of The Apical Plasma Membrane And Rapid Redistribution Of Lysosomal Enzymes And Mannose 6-Phosphate Receptors During Osteoclast Inactivation By Calcitonin. J Cell Sci. Nov. 1990;97 ( Pt 3):439-47.
Baylink et al., "Coupling Factor." Adv Exp Med Biol. 1982;151:409-21.
Bikle And Halloran, The Response Of Bone To Unloading. Bone Miner Metab. 1999;17(4):233-44.
Blaine et al., "Modulation of the production of cytokines in titanium-stimulated human peripheral blood monocytes by pharmacological agents. The role of cAMP-mediated signaling mechanisms." J Bone Joint Surg Am. Oct. 1997;79(10):1519-28.
Blaine et al., Increased levels of tumor necrosis factor-alpha and interleukin-6 protein and messenger RNA in human peripheral blood monocytes due to titanium particles. J Bone Joint Surg Am. Aug. 1996;78(8):1181-92.
Blair et al., "Recent advances toward understanding osteoclast physiology." Clin Orthop. Sep. 1993;(294):7-22.
Bonewald et al., "Stimulation of matrix vesicle enzyme activity in osteoblast-like cells by 1,25(OH)2D3 and transforming growth factor beta (TGF beta)." Bone Miner. May 1992;17(2):139-44.
Bronckers et al., DNA fragmentation during bone formation in neonatal rodents assessed by transferase-mediated end labeling. J Bone Miner Res. Sep. 1996;11(9):1281-91.

(Continued)

*Primary Examiner*—Karen Cochrane Carlson
(74) *Attorney, Agent, or Firm*—Needle & Rosenberg, P.C.

(57) ABSTRACT

Disclosed are compositions and methods related to osteoblasts, osteoclasts, and osteoclast lacunae.

19 Claims, 27 Drawing Sheets

OTHER PUBLICATIONS

Burger and Klein-Nulend, Mechanotransduction in bone—role of the lacuno-canalicular network. FASEB J. 1999;13 Suppl:S101-12.

Cheifetz et al., Influence of osteogenic protein-1 (OP-1;BMP-7) and transforming growth factor-beta 1 on bone formation in vitro. Connect Tissue Res. 1996;35(1-4):71-8.

Chen et al., A WD-domain protein that is associated with and phosphorylated by the type II TGF-beta receptor. Nature. Oct. 12, 1995;377(6549):548-52.

Choy and Derynck, The type II transforming growth factor (TGF)-beta receptor-interacting protein TRIP-1 acts as a modulator of the TGF-beta response. J Biol Chem. Nov. 20, 1998;273(47):31455-62.

Chung et al., Serial passage of MC3T3-E1 cells alters osteoblastic function and responsiveness to transforming growth factor-beta1 and bone morphogenetic protein-2. Biochem Biophys Res Commun. Nov. 1999;265(1):246-51.

Delaisse et al. (1985) Bisphosphonates and bone resorption: effects on collagenase and lysosomal enzyme excretion. Life Sciences. 37:2291-6.

Epker and Frost, "The nature of bone resorption and formation in normalcy and disease." Henry Ford Hosp Med J. 1968 Spring;16(1):29-39.

Evans et al.. Future of adenoviruses in the gene therapy of arthritis. Arthritis Research. 3(3):142-6, 2001.

Franzoso et al., Requirement for NF-kappaB in osteoclast and B-cell development. Genes Dev. Dec. 15, 1997;11(24):3482-96.

Frost, Journal of Bone & Joint Surgery-American vol. 48 (6): 1192-203, 1966.

Ghivizzani et al.. Gene therapy approaches for treating rheumatoid arthritis. Clinical Orthopaedics & Related Research. (379 Suppl):S288-99, 2000.

Griswold-Prenner, et al., Physical and functional interactions between type I transforming growth factor beta receptors and Balpha, a WD-40 repeat subunit of phosphatase 2A. Mol Cell Biol. Nov. 1998;18(11):6595-604.

Grzesik and Robey, Bone matrix RGD glycoproteins: immunolocalization and interaction with human primary osteoblastic bone cells in vitro. J Bone Miner Res. Apr. 1994;9(4):487-96.

Harris and Heaney, "Skeletal renewal and metabolic bone disease." N Engl J Med. Jan. 30, 1969;280(5):253-9 contd.

Harris and Heaney, "Skeletal renewal and metabolic bone disease." N Engl J Med. Feb. 6, 1969;280(6):303-11 concl.

Harris et al., Effects of transforming growth factor beta on bone nodule formation and expression of bone morphogenetic protein 2, osteocalcin, osteopontin, alkaline phosphatase, and type I collagen mRNA in long-term cultures of fetal rat calvarial osteoblasts. J Bone Miner Res. Jun. 1994;9(6):855-63.

Hayman et al., Mice lacking tartrate-resistant acid phosphatase (Acp 5) have disrupted endochondral ossification and mild osteopetrosis. Development. Oct. 1996;122(10):3151-62.

Hayman et al., Widespread expression of tartrate-resistant acid phosphatase (Acp 5) in the mouse embryo. J Anat. Apr. 2000;196 (Pt 3):433-41.

Hirano et al., Does suppression of bone turnover impair mechanical properties by allowing microdamage accumulation? Bone. Jul. 2000;27(1):13-20.

Hock et al., Osteoblast apoptosis and bone turnover. J Bone Miner Res. Jun. 2001;16(6):975-84.

Howard et al., Parathyroid hormone stimulates bone formation and resorption in organ culture: evidence for a coupling mechanism. Proc Natl Acad Sci U S A. May 1981;78(5):3204-8.

Howard GA. et al., "Coupled bone metabolism in vitro: embryonic chick limbs in organ culture." Prog Clin Biol Res. 1982;101:259-74.

Humphrey and Enoch, Sum1, a highly conserved WD-repeat protein, suppresses S-M checkpoint mutants and inhibits the osmotic stress cell cycle response in fission yeast. Genetics. Apr. 1998;148(4):1731-42.

Ionescu et al. PTHrP modulates chondrocyte differentiation through AP-1 and CREB signaling. J Biol Chem. Apr. 13, 2001;276(15):11639-47. Epub Jan. 2, 2001.

Ishibashi et al., Quantification of the expression levels of lysosomal cysteine proteinases in purified human osteoclastic cells by competitive RT-PCR. Calcif Tissue Int. Feb. 2001;68(2):109-16. Erratum in: Calcif Tissue Int Jun. 2002;68:109-116.

Ishibe, et al., Activation of osteoblast insulin-like growth factor-II/ cation-independent mannose-6-phosphate receptors by specific phosphorylated sugars and antibodies induce insulin-like growth factor-II effects. Endocr Res. 1991;17(3-4):357-66.

Ishibe, et al., Human prostatic acid phosphatase directly stimulates collagen synthesis and alkaline phosphatase content of isolated bone cells. J Clin Endocrinol Metab. Oct. 1991;73(4):785-92.

Ishibe, et al., Stimulation of bone formation in vivo by insulin-like growth factor-II in rats. Calcif Tissue Int. Jul. 1998;63(1):36-8.

Jiang and Clouse, Expression of a plant gene with sequence similarity to animal TGF-beta receptor interacting protein is regulated by brassinosteroids and required for normal plant development. Plant J. Apr. 2001;26(1):35-45.

Karhukorpi et al. (1992) A difference in the enzyme contents of resorption lacunae and secondary lysosomes of osteoclasts. Acta Histochemica. 92:1-11.

Kassem et al., Production and action of transforming growth factor-beta in human osteoblast cultures: dependence on cell differentiation and modulation by calcitriol. Eur J Clin Invest. May 2000;30(5):429-37.

Kleeff et al., The cell-surface heparan sulfate proteoglycan glypican-1 regulates growth factor action in pancreatic carcinoma cells and is overexpressed in human pancreatic cancer. J Clin Invest. Nov. 1, 1998;102(9):1662-73.

Kleeff et al.. Stable transdection of glypican antisense construct decreases tumorigenicity in PANC-1 pancreatic carcinoma cells. Pancreas. 19(3):281-8,1999.

Kremer et al. (1995) Estrogen modulation of osteoclast lysosomal enzymes secretion. Journal of Cellular Biochemistry. 57:271-9.

Kwon et al., Titanium particles inhibit osteoblast adhesion to fibronectin-coated substrates. J Orthop Res. Mar. 2000;18(2):203-11.

Lewis and Dean, Automated site-directed drug design: the concept of spacer skeletons for primary structure generation. Proc R Soc Lond B Biol Sci. Mar. 22, 1989;236(1283):125-40.

Ling and Roberts, Uteroferrin and intracellular tartrate-resistant acid phosphatases are the products of the same gene. J Biol Chem. Apr. 5, 1993;268(10):6896-902.

Lorenzo et al. (1984) Effects of phosphate on calcium release, lysosomal enzyme activity in the medium, and osteoclast morphometry in cultured fetal rat bones. Metabolic Bone Disease & Related Research. 5:187-90.

MacDonald, A single receptor binds both insulin-like growth factor II and mannose-6-phosphate. Science. Mar. 4, 1988;239(4844):1134-7.

Martinez et al. Identification of functional insulin-like growth factor-II/mannose-6-phosphate receptors in isolated bone cells. J Cell Biochem. Oct. 1995;59(2):246-57.

Mundy et al., Unidirectional migration of osteosarcoma cells with osteoblast characteristics in response to products of bone resorption. Calcif Tissue Int. 1982;34(6):542-6.

Ohsawa et al. (1993) Lysosomal cysteine and aspartic proteinases, acid phosphatase, and an endogenous cysteine proteinase inhibitor, cystatin-beta, in rat osteoclasts. Journal of Histochemistry & Cytochemistry. 41:1075-83.

Olbrich, et al., Water permeability and mechanical strength of polyunsaturated lipid bilayers. Biophys J. Jul. 2000;79(1):321-7.

Parfitt AM. , "Bone remodeling and bone loss: understanding the pathophysiology of osteoporosis." Clin Obstet Gynecol. Dec. 1987;30(4):789-811.

Parfitt Am., "The actions of parathyroid hormone on bone: relation to bone remodeling and turnover, calcium homeostasis, and metabolic bone diseases. II. PTH and bone turnover and plasma calcium regulation." Metabolism. Aug. 1976;25(8):909-55.

Pilia et al. (1996) Mutations in GPC, a glypican gene, cause the Simpson-Golabi-Behmel overgrowth syndrome. Nature Genetics 12:241-247.

Pollice et al., Interleukin-10 inhibits cytokine synthesis in monocytes stimulated by titanium particles: evidence of an anti-inflammatory regulatory pathway. J Orthop Res. Nov. 1998;16(6):697-704.

Romano et al., The reversal line may be a key modulator of osteoblast function: observations from an alveolar bone wound-healing model. J Periodontal Res. Jan. 1997;32(1 Pt 2):143-7.

Sasaki and Ueno-Matsuda (1993) Cysteine-proteinase localization in osteoclasts: an immunocytochemical study. Cell & Tissue Research. 27:177-9.

Schmaljohn et al., Production and characterization of human monoclonal antibody Fab fragments to vaccinia virus from phage-display combinatorial library. Virology. May 25, 1999;258(1):189-200.

Schwartz et al., Implant surface characteristics modulate differentiation behavior of cells in the osteoblastic lineage. Adv Dent Res. Jun. 1999;13:38-48.

Schwarz et al., Molecular regulation of human interleukin 2 and T-cell function by interleukin 4. Proc Natl Acad Sci U S A. Aug. 15, 1993;90(16):7734-8.

Schwarz et al., NF-kappaB-mediated inhibition of apoptosis is required for encephalomycarditis virus virulence: a mechanism of resistance in p50 knockout mice. J Virol. Jul. 1998;72(7):5654-60.

Seeman and Delmas, Reconstructing the skeleton with intermittent parathyroid hormone. Trends Endocrinol Metab. Sep. 2001;12(7):281-3.

Shioda et al., A green fluorescent protein-reporter mammalian two-hybrid system with extrachromosomal maintenance of a prey expression plasmid: application to interaction screening. Proc Natl Acad Sci U S A. May 9, 2000;97(10):5220-4.

Siebertz et al. (1999) Expression of glypican-4 in haematopoietic-progenitor and bone marrow stromal cells. Biochemical. J. 344:937-43.

Song et al., OCI-5/rat glypican-3 binds to fibroblast growth factor-2 but not to insulin-like growth factor-2. J Biol Chem. Mar. 21, 1997;272(12):7574-7.

Spanner et al., The iron-binding protein ferritin is expressed in cells of the osteoblastic lineage in vitro and in vivo. Bone. Aug. 1995;17(2):161-5.

Steinfeld et al., Stimulation of fibroblast growth factor receptor-1 occupancy and signaling by cell surface-associated syndecans and glypican. J Cell Biol. Apr. 1996;133(2):405-16.

Stepan et al., "Purification and N-terminal sequence of two tartrate-resistant acid phosphatases type-5 from the hairy cell leukemia spleen." Biochem. Biophys. Res. Commun. 165(3):1027-1034 (Dec. 29, 1989).

Sugawara et al., Sp1 and SF-1 interact and cooperate in the regulation of human steroidogenic acute regulatory protein gene expression. Endocrinology. Aug. 2000;141(8):2895-903.

Tagami et al., The interaction of the vitamin D receptor with nuclear receptor corespressors and coactivators. Biochem Biophys Res Commun. Dec. 18, 1998;253(2):358-63.

Takahashi et al., Osteoclast-like cell formation and its regulation by osteotropic hormones in mouse bone marrow cultures. Endocrinology. Apr. 1988;122(4):1373-82.

Tindberg et al., Contribution of MAP kinase pathways to the activation of ATF-2 in human neuroblastoma cells. Neurochem Res. Apr. 2000;25(4):527-31.

Vaes et al. (1992) Relative roles of collagenase and lysosomal cysteine-proteinases in bone resorption. Matrix Supplement. 1:383-8.

Villanueva AR. et al., "Bone and cell dynamics in the osteoporoses: a review of measurements by tetracycline bone labeling." Clin Orthop. Nov.-Dec. 1966;49:135-50.

Wergedal and Baylink, Distribution of acid and alkaline phosphatase activity in undemineralized sections of the rat tibial diaphysis. J Histochem Cytochem. Dec. 1969;17(12):799-806.

Worapamorn et al. Cell surface proteoglycan expression by human periodontal cells. Connect Tissue Res. 2000;41(1):57-68.

Wrana, Regulation of Smad activity. Cell. Jan. 21, 2000;100(2):189-92.

Xia et al., Localization of rat cathepsin K in osteoclasts and resorption pits: inhibition of bone resorption and cathepsin K-activity by peptidyl vinyl sulfones. Biol Chem. Jun. 1999;380(6):679-87.

Yamada et al., Effects of transforming growth factor-beta1 on the gene expression of decorin, biglycan, and alkaline phosphatase in osteoblast precursor cells and more differentiated osteoblast cells. Histochem J. Oct. 1999;31(10):687-94.

Yamamoto and Nagai, A histochemical study of acid phosphatases in medullary bone matrix and osteoclasts in laying Japanese quail. J Bone Miner Res. Nov. 1992;7(11):1267-73.

\* cited by examiner

COMPOSITIONS AND METHODS INVOLVED IN BONE GROWTH

This application is the National Stage of International Application No. PCT/US02/30093, filed Sep. 20, 2002 and which claims the benefit of United States Provisional Application No. 60/323,987 filed on Sep. 20, 2001, entitled "Compositions and methods involved in bone growth," which application is herein incorporated by reference in its entirety.

I. ACKNOWLEDGEMENT

This invention was made with government support under federal grants RO1 DE 12011 and RO1 ES 08121, awarded by the NIH. The Government has certain rights to this invention.

II. BACKGROUND

The concept of a coupled communication between osteoblastic bone formation and osteoclastic bone resorption was first described in humans by Harris and Heaney in 1969 (Harris W H. Heaney R. P., New England Journal of Medicine. 280(5):253-9 contd, 1969; Harris W H. Heaney R P., New England Journal of Medicine. 280(6):303-11 concd 1969). They showed that in patients with high rates of resorption there was a correspondingly high rate of bone formation and concluded that the maintenance of a steady state skeletal mass required that osteoclastic bone resorption be matched in amount by osteoblastic bone formation. They based their investigations on conceptual principles put forward by Frost (Epker B N. Frost H M., Henry Ford Hospital Medical Journal. 16(1):29-39, 1968; Villanueva A R. et al., Clinical Orthopaedics & Related Research. 49:135-50, 1966; Frost H M., Journal of Bone & Joint Surgery—American Volume. 48(6):1192-203, 1966) and Parfit (Parfitt A M., Clinical Obstetrics & Gynecology. 30(4):789-811, 1987; Parfitt A M., Metabolism: Clinical & Experimental. 25(8):909-55, 1976). William Harris and Robert Heaney coined the term "coupling."

Coupling was defined at a molecular and cellular level by Howard, Baylink and others (Howard G A. et al., Progress in Clinical & Biological Research. 101:259-74, 1982; Howard G A. et al., Proceedings of the National Academy of Sciences of the United States of America. 78(5):3204-8, 1981; Baylink D. et al., Advances in Experimental Medicine & (Biology. 151:409-21, 1982.) as a release of growth factors from bone during resorption leading to the subsequent activation and differentiation of osteoblasts for the process of bone formation. They presented evidence for a "coupling factor" that could be recovered in the medium of bone undergoing resorption. Coupling factor turned out to be a number of molecules including the IGF's, TGFβ's and BMP's.

Therefore, both systemic hormones such as PTH and local factors such as the TGFβ's, BMP's and IGF's are molecules with the potential to stimulate both osteoblast number and osteoblast differentiation. However, what has not been universally appreciated as part of the remodeling process is that bone formation occurs on the immediate surface of the resorptive event. That is, growth factor diffusion from a resorption site occurs with a larger radius than is encompassed by the actual site of bone formation, yet bone is deposited at the site of bone resorption. This argues that there must be a site-specific localization to the formation process. Teleologically, this makes sense, since if bone were deposited at sites other than those undergoing resorption, it might lead to alteration of trabecular architecture and contribute to the formation of structurally unsound bone.

Osteoclastic bone resorption depends on the formation of adhesive bonds between the cell and the bone surface as well as the formation of two critical ultrastructural features; the ruffled boarder and sealing (or clear) zone. At the ruffled border the cell actively pumps large numbers of protons into the space between the cell and bone. pH is decreased to the range of approximately 5.0 to 6.0 and the hydroxyapatite becomes soluble. Secretion of lysosomal enzymes and other acidic hydrolases into this space begins the process of collagen and non-collagen protein breakdown. In many ways the space between the osteoclast and the bone surface becomes an extracellular lysosome characterized by high levels of lysosomal enzymes and a low pH. In fact, the brush border membrane of the osteoclast has been shown to contain high levels of the mannose-6-phosphate receptor (Al Kawas S. et al., Calcified Tissue International. 59(3): 192-9, 1996; Blair H C. et al., Clinical Orthopaedics & Related Research. (294):7-22, 1993 September; Baron R. et al., Journal of Cell Science. 97 (Pt 3):439-47, 1990; Baron R. et al., Journal of Cell Biology. 106(6):1863-72, 1988 June). This receptor is responsible for trafficking lysosomal enzymes to a lysosome. When present on osteoclast (or ameloblast) brush border membranes it presumably can direct these enzymes to the active resorbing surface. These osteoclast enzymes remain firmly attached to the resorption surface (Xia L. et al., Biological Chemistry. 380(6):679-87, 1999 June; Romano P R. et al., Journal of Periodontal Research. 32(1 Pt 2):143-7, 1997).

Mannose-6-phosphate moieties present on lysosomal enzymes have the ability to activate the mannose-6-phosphate receptor. Since the mannose-6-phosphate receptor shares identity with the IGF-II receptor, activation of this receptor by lysosomal enzymes could induce a growth factor like effect (Ishibe, M., et al., J. Clin. Endocrinol. Metab. 73: 785-792 (1991); Ishibe, M., et al., Endocrine Research. 17: 357-366 (1991); Martinez, D. A., et al., (1995) J. Cellular Biochemistry 59: 246-257; Ishibe, M., et al., Cal. Tissue Intl. 63:36-38 (1998).).

Thus, there exists a need for identification of the molecules involved in mediating the osteoblast/osteoclast/osteoclast lacuna interactions and signalings. Disclosed herein are compositions and methods that are involved in these interactions and can mediate the bone resorptive/formative event.

III. SUMMARY

Disclosed are compositions and methods involved in interactions with osteoblasts, osteoclasts, and/or osteoclast lacuna.

IV. BRIEF DESCRIPTION OF THE DRAWINGS

The accompanying drawings, which are incorporated in and constitute a part of this specification, illustrate several embodiments and together with the description, serve to explain the principles of the disclosed compositions and methods.

FIG. 1 shows a diagram of bone resorption and formation.

FIG. 2. shows a bio-panning strategy for use with phage display. Both a random and an osteoblast cDNA phage display library have been utilized. This figure depicts a random library in M13. The "bait" is immobilized TRAP on a tissue culture dish. After three rounds of panning, elution and amplification, the remaining adherent phage are sequenced.

FIG. 3A shows osteoblast binding as a function of resorption area. Bone wafers with different amounts of osteoclast lacunae were used to demonstrate that more osteoblasts adhere to wafers with more lacunae. FIG. 3B shows osteoblasts cultured on wafers with pitted osteoclast lacunae are stimulated to produce more alkaline phosphatase and proliferate at a slightly greater rate. Treatment of the wafers with a endoglycosidase H blocks some of the effect.

FIG. 4 shows the effect of TRAP on osteoblast proliferation, collagen synthesis and alkaline phosphatase activity. TRAP (purified uteroferrin donated by Dr. M. Roberts) was exposed to osteoblasts in culture in a dose dependent fashion. There was a modest stimulation of proliferation and marked stimulation of differentiation as noted by collagen and alkaline phosphatase increases. Treatment of the TRAP with a glycosidase eliminated the effect on alkaline phosphatase. N=4-6. "*" statistically significant at p 0.05.

FIG. 5 shows ELISA assay for the five phage clones with highest consensus frequency from Table 4. TRAP, immobilized in 96 well culture wells, was used as the substrate to demonstrate the affinity of phage. All of these phage demonstrated at least a 40 fold higher binding than wild type (WT) phage. Clone 5 phage (dark bar) was used for further analyses. Non of the phage demonstrated a statistically significant difference from each other, however, all were different from control.

FIG. 6 shows a Scatchard-type analysis for Clone 5 phage binding to TRAP. Immobilized TRAP was used as a substrate and phage binding was determined by measuring the titer of phage in the unbound fraction. A Kd in the sub-nanomolar range was obtained.

FIG. 7 shows a principle of a Far-Western. Phage are used as the probes to identify specific proteins separated by gel electrophoresis. The phage are identified with a HRP-conjugated antibody directed against a phage coat protein.

FIG. 8 shows inhibition of osteoblast binding. A synthetic peptide corresponding to the Clone 5 sequence effectively competes with osteoblast binding to pitted bone wafers. Osteoblasts prelabelled with 3H-leucine were used to measure cell affinity for cortical bone wafers in the presence and absence of resorption lacunae. As shown in FIG. 3 osteoblasts bind with higher affinity to pitted wafers. However, a Clone 5 peptide can inhibit the binding at as little as 10 pM. N=8.

FIG. 9 shows effect of TRAP on activation of a TGFβ reporter construct (P3TPlux). P3TP lux was transfected into osteoblasts and they were then exposed to TRAP or TGFβ Panel A shows that TRAP can activate P3TP lux in a dose dependent fashion. Panel B shows that, as expected, TGFβ can strongly activate P3TP lux but that addition of TRAP augments the TGFβ effect. Note the difference in scales. N=4-6. All data points are statistically significantly different from the first bar in their respective graph.

FIG. 10 shows measuring cell affinity for a substrate. The horizontal axis is the touch number and vertical axis is the cumulative percent of touches that lead to an adhesive event. Each point represents the mean of at least 9 cells. Error bars are omitted so as not to clutter the figure.

FIG. 11 shows TGFβ activation pathways. Three main regulatory pathways converging on two transactivating transcription factors have been described for TGFβ activation. The pathways have been highlighted and from left to right they are: the JNK pathway, the p38 pathway and the Smad pathway.

FIG. 12 shows a mammalian two-hybrid assay for TRAP and glypican 4 (GPC4) interaction. TRAP was expressed as a fusion protein with Ga14 BD (Ga14-BD-TRAP). GPC4 was expressed as a fusion protein with VP16AD (VP-16-AD-GPC4). When both fusion constructs were co-transfected into MG-63 cells, the association of TRAP with GPC4 allowed for promoter activation and polymerase activity to proceed for the transcription and translation of luciferase. Control transfections with single constructs of Ga14-BD-TRAP and VP-16-AD-GPC4 did not stimulate luciferase expression. Transfection with a VP-16-AD-GPC4 construct deficient in the 12 amino acids of Clone 5 (VP-16-AD-GPC412) also could not stimulate luciferase expression. Moreover, and most importantly, co-transfection of Ga14-BD-TRAP with VP-16-AD-GPC412 did not stimulate luciferase activity.

FIG. 13 shows clone 5 peptide interferes with osteoblast binding to osteoclast lacunae. Osteoblasts bind in greater number to wafers containing osteoclasts pits. A synthetic peptide corresponding to the Clone 5 sequence can interfere with this osteoblast binding in a dose dependent fashion. "†" indicates a statistically significant difference between osteoblast binding on osteoclast pitted wafers vs. un-pitted wafers (p 0.005). "*" indicates a statistically significant difference between wafers treated with the Clone 5 peptide and control pitted wafers (to p levels of at least 0.05). Each value is the mean±one SEM; N=6.

FIG. 14 shows the effect of TRAP and TGFβ on osteoblast phenotypic markers. The qualitative pattern of stimulation by TRAP and TGFβ for markers of osteoblast differentiation is similar. The concentration of TRAP was 10 µg/ml and for TGFβ was 2 ng/ml for all determinations. Alkaline phosphatase (Alk. Phos.) was measured in a direct biochemical assay. Runx2 and osteoprotegerin (OPG) were quantified in an ELISA assay using commercially available antibodies. Collagen was measured by determining the amount of collagenase-digestible protein present in pre-labeled osteoblasts (34). All data are expressed as a percent of the control, untreated cells. All data points are the mean±one SEM. * p 0.05. ** p 0.01.

FIGS. 15A and 15B show the specificity and affinity of TRAP binding to TRIP-1. FIG. 15A demonstrates that wild type phage (containing no osteoblast proteins) have little affinity for TRAP that has been immobilized in a culture dish. TRIP-1-containing phage show a dose dependent increase in TRAP binding. Phage titer is expressed as particles/ml. Phage binding was detected with HRP-anti T7 phage antibody in a sandwich ELISA assay. All TRIP-1 phage data points are the mean±one SEM. ** $p \leq 0.01$. FIG. 15B demonstrates the specificity of TRIP-1 binding to TRAP. Human TRIP-i was synthesized as a GST fusion protein. The GST vector alone served as a control protein. Different amounts of TRAP and other proteins (i.e. bovine serum albumin, BSA) were incubated with the GST-TRIP-1 fusion protein and the molecules associating with the GST-TRIP-1 were extracted by exposure to glutathione beads. The "pulled-down" proteins were separated on a denaturing gel and the level of TRAP was measured with Far Western analysis. Lane A shows that GST has no affinity for TRAP. Lane B shows that TRIP-1 does not bind to any molecules in BSA that would be detected in the Far Western. Lanes C and D show that increasing amounts of TRAP can be captured by the GST-TRIP-1 in a dose-dependent fashion. Lane E is a control lane loaded with TRAP to demonstrate the detection of this system.

FIG. 16 shows a two hybrid demonstration of TRAP association with TRIP-1. A mammalian two-hybrid system was utilized to demonstrate an association between TRAP and TRIP-1. 293T cells, when individually transfected with a Ga14-DBD-TRIP-1 or VP-16-AD-TRAP fusion protein, showed no activation of the luciferase reporter. However, co-transfection of the cells with both constructs allowed for interaction of TRAP with TRIP-1. This association permitted the assembly of the transcription machinery for luciferase expression. Substitution of an anti-sense form of TRIP-1 as the Gal4-DBD fusion protein, as expected, did not show any association with TRAP. All data are the mean of four determinations±SEM. ** p 0.01 as compared Gal4-BD-TRAP.

FIG. 17 shows TRAP and TGFβ activate the Smad signaling pathway. P3TPLux is a Smad 2, 3 sensitive reporter. Transfection of this reporter into either of the osteoblast cell lines, SaOS2 or MG-63, and exposure of the cells to TRAP (10 µg/ml) or TGFβ (5 ng/ml) causes an activation of the Smad pathway. The effect of TRAP plus TGFβ are additive. Co-transfection of the cells with a dominant negative TGFβ type II receptor blocks all TRAP and TGFβ signaling. Each bar is the mean of at least four determinations±SEM. * p 0.05 and ** p 0.01 as compared to control. The data for MG-63 cells are shown. The data for the SaOS2 cells are the same (data not shown).

FIG. 18 shows TRAP and TGFβ signaling in a Smad4 deficient cell line. SW408 cells are deficient in Smad4, a requisite co-factor for Smad2 and 3 signaling. The data in this figure demonstrate that neither TRAP nor TGFβ (nor the combination of factors) can activate the Smad signaling pathway in SW408 cells. However, when the cells are transfected with both Smad4 and TRIP-1, restoration of Smad signaling can occur. All values are the mean±SEM. * p 0.05 and ** p 0.01 as compared to control.

FIG. 19 shows a demonstration of a TRIP-1, TGFβ type II receptor, Smad2 complex with TRAP. 293T cells were transfected with TGFβRII. Some of these cells were then co-transfected with a "His"-tagged TRIP-1 (His-TRIP-1). In lane A, in which both the receptor and TRIP-1 were present, but GST-TRAP was not added, no parts of the complex could be "pulled down" with glutathione coated beads. The same was true if His-TRIP-1 was not transfected into the cells. However, if the receptor, TRIP-1 and GST-TRAP were all present, a protein complex composed of the receptor, TRIP-1 and Smad 2 could be extracted with glutathione coated beads. These data indicate that TRAP, TRIP-1, the TGFβRII and Smad2 can be found is close association with each other.

FIG. 20 shows DNA laddering, a hallmark of apoptosis, also occurs in the ROS17/2.8 cell line after exposure to TRAP.

FIG. 21A shows that early passage rat osteoblasts (day 3) (D3 ROB) and MC3T3-E1 cells have very low levels of collagenase III. FIG. 21A and 21C show that this level increases as the rat osteoblasts mature (day 14) (D14 ROB) and reaches a maximum in ROS 17/2.8 cells (21C). FIG. 21B demonstrates an increase in the senescence-associated β-galactosidase in day 14 osteoblasts, with and without the addition of the differentiating agent β-glycerol phosphate.

FIGS. 22A-C show an examination of apoptotic DNA fragmentation in ROS 17/2.8 cells.

FIGS. 25A-C show cleavage of caspase 3 in day 14 cells treated with TRAP.

Figure 26:
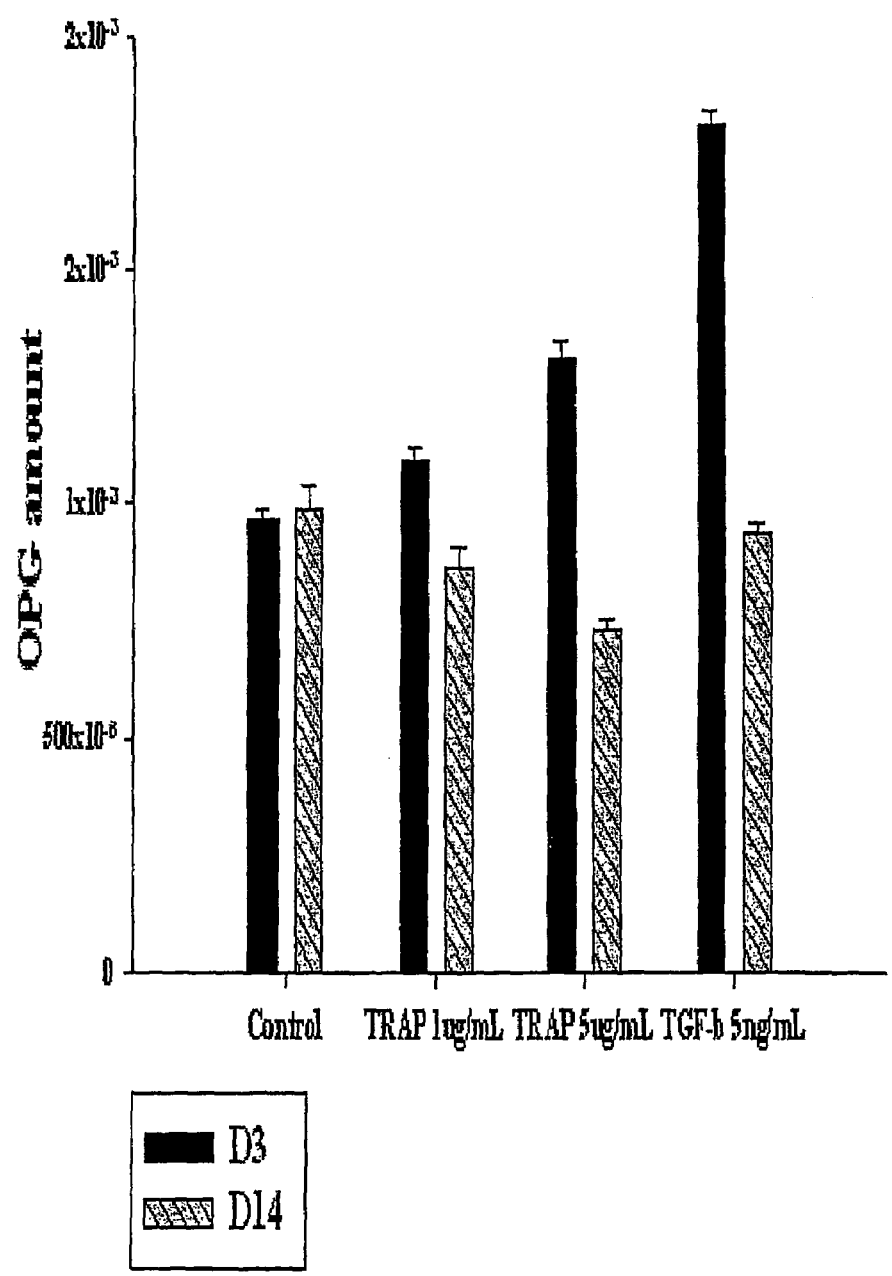

FIG. 26 shows ELISA assays that determine the levels of OPG in primary osteoblast cells.

V. DETAILED DESCRIPTION

Before the present compounds, compositions, articles, devices, and/or methods are disclosed and described, it is to be understood that they are not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs or nucleotide substitutions available in the art.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs or nucleotide substitutions available in the art which do not interfere with the enzymatic manipulation.

Disclosed are the components to be used to prepare the disclosed compositions as well as the compositions themselves and to be used within the methods disclosed herein. These and other materials are disclosed herein, and it is understood that when combinations, subsets, interactions, groups, etc. of these materials are disclosed that while specific reference of each various individual and collective permutation of these compounds may not be explicitly disclosed, each is specifically contemplated and described herein. For example, if a particular TRIP is disclosed and discussed and a number of modifications that can be made to a number of molecules including the TRIP are discussed, specifically contemplated is each and every combination and permutation of TRIP and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Throughout this application, various publications are referenced. The disclosures of these publications in their entireties are hereby incorporated by reference into this application in order to more fully describe the state of the art. The references disclosed are also individually and specifically incorporated by reference herein for the material contained in them that is discussed in the sentence in which the reference is relied upon.

B. Compositions and methods

Figure 1:
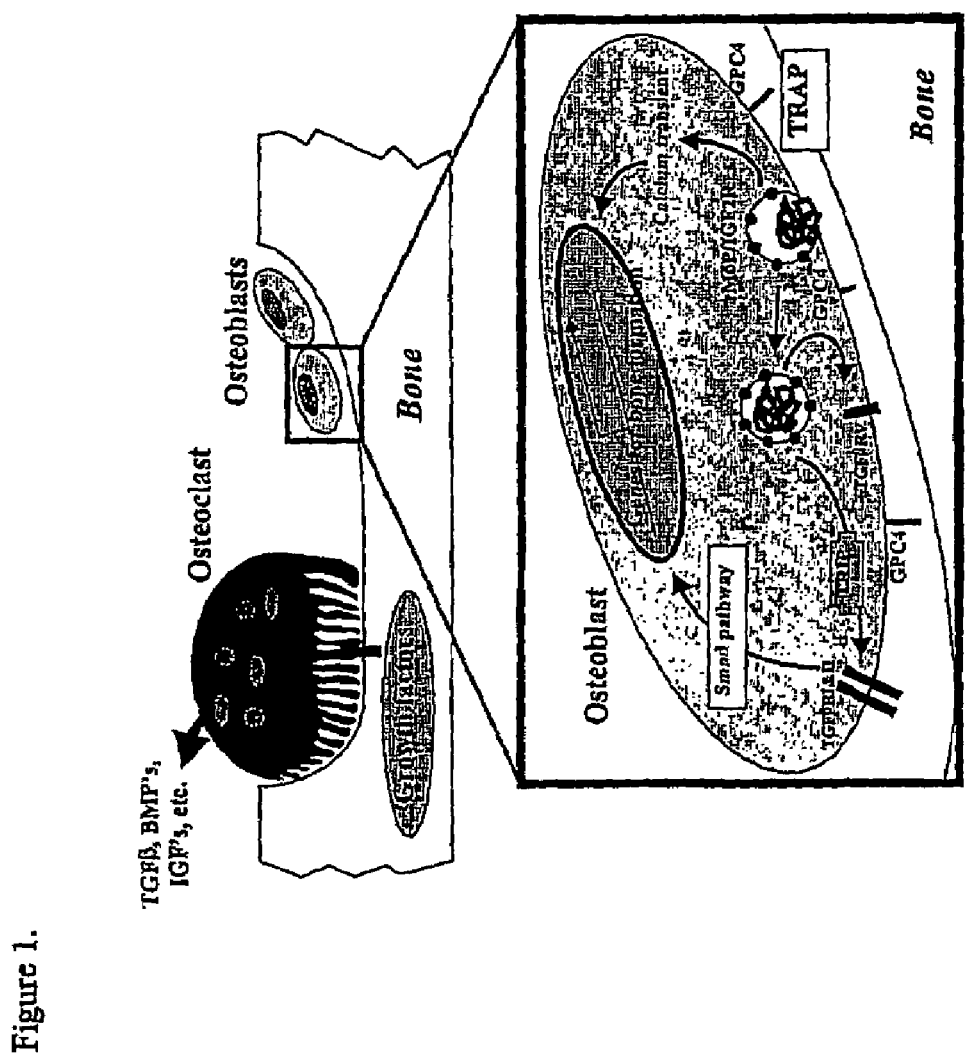

FIG. 1, shows a diagram of the process that occurs during bone resorption and formation. Bone resorption occurs when osteoclasts begin, through lysosomal enzymes and pH regulation of the extracellular space between the bone and the osteoclasts, to degrade the bone at the junction of the osteoclasts and the bone. This produces an osteoclast lacunae which in turn is specifically recognized by osteoblasts. Disclosed herein are compositions and methods that are drawn to this recognition event between osteoblasts and osteoclast lacunae. Once the osteoblasts recognize the osteoclast lacunae, bone formation can begin, through differentiation and proliferation of osteoblasts. This process of differentiation and proliferation occurs at the site of resorption, the osteoclast lacunae and is mediated by this region. Compositions and methods are disclosed which are drawn to and involved in this process of differentiation and proliferation. Thus, disclosed are compositions and methods, which are related to bone resorption and bone formation.

Disclosed are compositions and methods related to osteoblasts, osteoclasts, and osteoclast lacunae. Disclosed are peptides that interact with TRAP and with osteoclast lacunae. One of these peptides has substantial identity to a region of GPC4 (SEQ ID NO:38), which is a peptide that is expressed in osteoblasts, and full length GPC4, as disclosed herein, interacts with TRAP. Thus, compositions and methods that enhance or inhibit the interaction of GPC4 and TRAP, and thus enhance or inhibit the interactions of osteoblasts with osteoclasts and/or osteoclast lacuna, are disclosed.

Furthermore, it is disclosed that TRAP (SEQ ID NO:42) interacts with TRIP (TGFβ receptor interacting protein) (SEQ ID NO:40), which is a G-protein coupled cell signaling protein. It is shown that TRIP is expressed in osteoblasts. Thus, compositions and methods for affecting the interactions between TRAP and TRIP are disclosed. These compositions and methods in turn ultimately effect the bone formation properties controlled by TRAP and the interaction between osteoblasts and osteoclast lacuna.

It is also disclosed that TRAP can activate the Smad3/Smad4 TGFβ signaling pathway as well as that TRAP can stimulate osteoblast differentiation. Thus, disclosed are compositions and methods that affect TGFβ signaling pathways, such as the Smad3/Smad4 pathway and compositions and methods that affect the osteoblast differentiation, for example, through a TGFβ pathway.

It is also disclosed that TRAP can induce apoptosis of mature or end stage osteoblast cells. This apoptosis is mediated through TRIP utilizes a Ras/Raf pathway. Thus, disclosed are compositions and methods that affect the TRAP signaling pathways, involving apoptosis, such as compositions and methods that interrupt signaling between TRAP and Ras/Raf. Also disclosed are compositions and methods that affect the osteoblast apoptosis, for example, through a Ras/Raf pathway.

1. Apoptosis

Osteocyte apoptosis has been speculated to be a signal for bone resorption by osteoclasts in growing bone, and increased activation frequency in estrogen-deficiency osteoporosis. Osteocytes are the terminal differentiation stage of osteoblasts. Osteoclasts can induce osteocyte apoptosis by many singaling pathways. FasL, displayed on the surface of osteoclast, has been shown to directly bind to a receptor, Fas, found on the osteoblasts and osteocytes. Activation of the Fas receptor leads to apoptosis.

Osteoblast apoptosis occurs at sites of local remodeling and fracture repair in adult bone (Burger E H, Klein-Nulend J., *Faseb J* 13 Suppl:S101-12, 1999; Grzesik W J, Robey P G, *J Bone Miner Res* 9:487-96, 1994; Mundy G R, et al., *Calcif Tissue Int* 34:542-6, 1982; Schwartz Z., et al., *Adv Dent Res* 13:38-48, 1999).

Only a 30-50% transient increase osteoblast numbers will become their terminal differentiation stage (lining cell and osteocyte). Upon completion of new bone formation the cellular excess must be resolved by the controlled removal of the surplus cells. Alternative mechanisms for elimination of excess osteoblasts include differentiation, emigration, or cell death. Evidence for the latter course has been provided by the observation of local and selective cell death in the mineralizing rodent calvarium (Spanner M, et al., *Bone* 17:161-5, 1995).

In many tissues, apoptosis is the major mechanism of cell death responsible for modulating cell population size on a local basis (Parfitt A M, Bone Histomorphometry: Techniques and Interpretation.:143-223, (1983)) and is a likely candidate for the physiological regulation of osteoblast cell numbers in adult bone. The growth factors and cytokines, which can modulate and induce apoptosis in osteoblasts are thought to be TNF-α (Hock J M, et al., *J Bone Miner Res* 16:975-84, 2001). FasL (.Abe Y, et al., *J Lab Clin Med* 136:344-54, (2000)), IL-6 and TGF-β may induce apoptosis in osteoblastic cells.

Disclosed herein TRAP protein was added to different bone cell lines that represented either a progenitor or early stage osteoblast as well as a mature or end stage osteoblast. TRAP induced differentiation in early stage osteoblasts and osteoblast progenitors and caused apoptosis in mature or end stage osteoblasts. We also attempted to characterize the TRAP signaling pathway involved in this apoptosis-inducing effect. The traditional Ras and Raf signaling pathways were involved in the TRAP mediated apoptosis.

The cytological stages of apoptosis are characterized by rapid condensation of chromtin and budding of the cell membrane into enclosed apoptotic bodies containing well preserved organelles. A characteristic biochemical feature of the chromatin condensation is a double break of nuclear DNA at the linker regions between nucleosomal fragments. This nucleosomal fragmentation of DNA results from the activation of nucleases in cells. One such nuclease, DNA fragmentation factor (DFF, a caspase-activated deoxyribonuclease (CAD) and its inhibitor (ICAD), is capable of inducing DNA fragmentation and chromatin condensation after cleavage by caspase-3.

Osteoclastic bone resorption can only be initiated on a bare mineral surface. However, virtually all bone surfaces are covered with a layer of stromal cells. These quiescent stromal cells are derived from matured and scenescent osteoblasts that have completed a phase of formation in the past. The question remains; how does the approaching osteoclast clear these cells prior to attachment and initiation of bone formation. Disclosed herein it is consistent with the early secretion of enzymes (i.e. TRAP) in the vicinity of the stromal cells which cause the mature osteoblasts to undergo apoptosis which exposes the mineral surface for the osteoclast.

In vitro, late stage can be defined as the number of days in culture. 14 days of culture would represent late stage and 3 days would represent early stage. Late and early stage characteristics of the cells, as discussed herein, can also be used to determine what stage the cells are in. For example, biochemical or morphological markers as discussed herein can be used to identify the stage of the bone cell. In vivo, i.e. in an animal or human, late stage can be defined by the morphology of the cells. A late stage osteoblasts is flattened against the bone surface, elongated and showing no metabolic activity. An early stage osteoblast is plump, polygonal and a produces protein.

Biochemical confirmation of the effect of TRAP on osteoblast apoptosis can be obtained by assaying levels of caspase-3 and poly ADP-ribose polymerase (PARP) in these cells lines. Caspase-3 is an enzyme that is a key member of the apoptotic cascade. However, most cells have a constitutive amount of this enzyme. It is not until the caspase(s) are cleaved that they become activated. Any elevation of caspase 3 over the levels in early stage cells would be indication of the onset of apoptosis. It is a relative measure, in that the level of caspase 3 in the cell is compared to a control, early stage cell, such as a 3 day old cell.

Thus, another indicator of a cells progression through apoptosis is a measurement of its cleaved caspase 3 levels. Similarly, poly ADP-ribose polymerase is a substrate for active caspase 3 and increased levels of cleave PARP are indicative of an active caspase.

The stage of maturation of the osteoblast cell lines can also be determined by measuring collagenase III levels and levels of the senescence-associated b-galactosidase enzyme. Collagenase III (MMP-13) is marker for late stage osteoblast differentiation. It is induced by hormones and factors that enhance osteoblast development. Thus, presence of the collagenase III MMP-13) marker indicates late stage or mature osteoblasts.

ROS 17/2.8 osteosarcoma cells represent a highly differentiated stage of the osteoblastic lineage despite their transformed phenotype. They can express both high level of osteocalcin, alkaline phosphatase and the E11 antigen defining the osteoblast-osteocyte transition. Late differentiation stage primary osteoblastic cells can be made by using the in vitro cell senescence method (Ishibashi O, et al., *Calcif Tissue Int* 68:109-16, (2001)).

These aged cells are similar to other diploid cell models widely used in research on cellular aging (Bronckers A L, et al., *J Bone Miner Res* 11:1281-91, (1996)) and they exhibit phenotypic characteristics of in vitro cellular senescence, including a limited proliferative capacity in culture, a progressive decline in the rate of macromolecular synthesis and a dramatic change in morphology (an increase in cell size and spreading, and a changed organization of the cytoskeleton) (Howard G A, et al., *Proc Natl Acad Sci USA* 78:3204-8, (1981)).

Also, altered gene expression, higher levels of cytoplasmic neutral β-galactosidase activity, as well as a relative increase in gene expression of the osteoblast-specific collagenase III was demonstrated during aging of these cell lines in culture.

In the results disclosed herein, ROS 17/2.8 cells were incubated with 0.1% DMSO to scavenge the intracellular reactive oxygen species and then incubated with TRAP (5 ug/mL). DMSO, at this low concentration, itself won't cause any toxic effect on cells but can scavenge most of reactive oxygen species. However, this treatment did not protect cells from apoptosis induced by TRAP. Therefore, the TRAP-induced cell apoptosis is not due to a reactive oxygen species effect.

Disclosed herein the late stage (D14) of osteoblasts have less Osteoprotegrin (OPG) production when the cells have been treated with TRAP proteins and TGF-β. OPG is the deccoy receptor for the RNAKL and stop the osteoclastogenesis. RANKL and OPG has been proposed for the regulation of osteoclast differentiation function. Both OPG and RANKL can themselves also be regulated by TGF-β (MacDonald R G, *Science* 239:1134-7, (1988)). TRAP proteins also have the same effect of that of TGF-β to stimulate the osteoblast secreting OPG. The aged osteoblasts have less response to TRAP proteins and TGF-β. This lower the secretion amount of OPG the less the protection afforded from the osteoclast.

Certain branches of the TGF-β signaling pathway can be blocked by transfecting dominated negative form of Smad 2, 3, 4 and smurf 1 and 2 (smad specific ubquitin ligase) separately. Transfection of these dominant negative molecules did not affect the TRAP-induced apoptosis in a ROS 17/2.8 cell. There are also SMAD independent TGF-β signaling pathways also existed (Wrana J L., *Cell* 100:189-92, (2000), MacDonald R G, *Science* 239:1134-7, (1988)).

For instance, TGF-β rapidly activates Rho family guanosine triphophatases (GTPases); MAPKs, including ERKs, p38, and JNKs through their upstream kinase activators such as TAK1; and protein linase B (PKB, also called Akt). Moreover, the downstream pathway of TRIP-1 is the stress-activated MAP kinase pathway, required for cell cycle stress response Humphrey T, Enoch T *Genetics* 148:1731-42, (1998); MacDonald R G, *Science* 239:1134-7, (1988)).

Disclosed herein, ras and raf, the upstream regulators of MEKK affected the TRAP-induced apoptosis. Overexpression dominant negative (DN)-Ras and DN-Raf in the ROS 17/2.8 cells eliminated the TRAP apoptosis effect. Overexpression of Ras signaling can decrease the protein amount of integrin and increase the expression level of Fas in the transfected-osteoblast (MacDonald R G, *Science* 239:1134-7, (1988)).

Disclosed herein osteoclast (TRAP staining +) and aged osteoblast cells (senescence-associated β-galactosidase staining positive) are colocalize to the same area. Most of the SA-βgal positive cells are located in the growth plate area of long bone. This epiphysial growth plate contains most of the trabaculae bone and most of the bone remodeling happens in this area.

C. Compositions

1. Compositions That Bind Tartrate Resistant Acid Phosphatase TRAP

Disclosed are compositions that bind TRAP. Unless otherwise indicated the binding of compositions to TRAP can occur in any way that promotes an interaction between the composition and TRAP that is greater than a non-specific interaction. A non-specific interaction is defined as an interaction between TRAP and bovine serum albumin. Typically the composition has a $K_d$ for TRAP less than or equal to $10^{-5}$ M. In other embodiments the $K_d$ for TRAP is less than or equal to $10^{-6}$ M or the $K_d$ for TRAP is less than or equal to $10^{-7}$ M or the $K_d$ for TRAP is less than or equal to $10^{-8}$ M or the $K_d$ for TRAP is less than or equal to $10^{-9}$ M or the $K_d$ for TRAP is less than or equal to $10^{-10}$ M or the $K_d$ for TRAP is less than or equal to $10^{-11}$ M or the $K_d$ for TRAP is less than or equal to $10^{-12}$ M. An isolated nucleic acid molecule comprising a sequence encoding a peptide that binds tartrate resistant acid phosphatase is disclosed.

The composition can be determined to have an interaction with TRAP greater than a non-specific interaction by performing the following assays. TRAP binding affinity can be measured by use of a Scatchard analysis with TRAP as the immobilized substrate and the target protein as the ligand. The target protein can be expressed in phage and the phage can be detected with anti-phage antibodies. Calculation of the Vmax and Kd for binding would define the interaction. TRAP binding can also be measured with Western and Far-Western technology. Proteins separated on a gel and transferred to a membrane can be probed with TRAP. Detection of TRAP binding to specific proteain bands can be accomplished with antibodies to TRAP or phage expressing proteins with affinity for TRAP.

Disclosed are isolated nucleic acid molecules comprising a sequence encoding a means for binding tartrate resistant acid phosphatase and a region controlling the expression of the means for binding tartrate resistant acid phosphatase.

Also disclosed are isolated nucleic acid molecules comprising a sequence encoding an integration site and a means for binding tartrate resistant acid phosphatase.

Also disclosed are isolated nucleic acid molecules comprising a sequence encoding a replication site and a means for binding tartrate resistant acid phosphatase.

The means for binding TRAP can be any means capable of binding TRAP as discussed herein. For example, the peptides disclosed in SEQ ID NOs: 19-36, in particular SEQ ID NO:23 are means for binding TRAP.

Also disclosed are means for binding TRAP that do not comprise the peptides having the sequence set forth in SEQ ID NOs: 38 and 40.

2. Compositions that Bind Osteoblasts, Osteoclasts, and/or Osteoclast Lacuna

Disclosed are compositions that bind osteoblasts, osteoclasts, and/or osteoclast lacuna. Unless otherwise indicated the binding of compositions to osteoblasts, osteoclasts, and/or osteoclast lacuna can occur in any way that promotes an interaction between the composition and osteoblasts, osteoclasts, and/or osteoclast lacuna that is greater than a non-specific interaction. A non-specific interaction is defined as an interaction between osteoblasts, osteoclasts, and/or osteoclast lacuna and bovine serum albumin. Typically the composition has a $K_d$ for osteoblasts, osteoclasts, and/or osteoclast lacuna less than or equal to $10^{-5}$ M. In other embodiments the $K_d$ for osteoblasts, osteoclasts, and/or osteoclast lacuna is less than or equal to $10^{-6}$ M or the $K_d$ for osteoblasts, osteoclasts, and/or osteoclast lacuna is less than or equal to $10^{-7}$ M or the $K_d$ for osteoblasts, osteoclasts, and/or osteoclast lacuna is less than or equal to $10^{-8}$ M or the $K_d$ for osteoblasts, osteoclasts, and/or osteoclast lacuna is less than or equal to $10^{-9}$ M or the $K_d$ for osteoblasts, osteoclasts, and/or osteoclast lacuna is less than or equal to $10^{-10}$ M or the $K_d$ for osteoblasts, osteoclasts, and/or osteoclast lacuna is less than or equal to $10^{-11}$ M or the $K_d$ for osteoblasts, osteoclasts, and/or osteoclast lacuna is less than or equal to $10^{-12}$ M. An isolated nucleic acid molecule comprising a sequence encoding a peptide that binds tartrate resistant acid phosphatase.

The composition can be determined to have an interaction with osteoblasts, osteoclasts, and/or osteoclast lacuna greater than a non-specific interaction by performing the following assays. Osteoblasts, osteoclasts, and/or osteoclast lacuna binding affinity for the composition can be measured by use of a Scatchard analysis with osteoblasts, osteoclasts, and/or osteoclast lacuna as the immobilized substrate and the target protein as the ligand. The target protein can be expressed in phage and the phage can be detected with anti-phage antibodies. Calculation of the Vmax and Kd for binding would define the interaction. Osteoblasts, osteoclasts, and/or osteoclast lacuna binding can also be measured with Western and Far-Western technology. Proteins separated on a gel and transferred to a membrane can be probed with osteoblasts, osteoclasts, and/or osteoclast lacuna. Detection of osteoblasts, osteoclasts, and/or osteoclast lacuna binding to specific proteain bands can be accomplished with antibodies to osteoblasts, osteoclasts, and/or osteoclast lacuna or phage expressing proteins with affinity for osteoblasts, osteoclasts, and/or osteoclast lacuna.

Disclosed are isolated nucleic acid molecules comprising a sequence encoding a means for binding osteoblasts, osteoclasts, and/or osteoclast lacuna and a region controlling the expression of the means for binding tartrate resistant acid phosphatase.

Also disclosed are isolated nucleic acid molecules comprising a sequence encoding an integration site and a means for binding osteoblasts, osteoclasts, and/or osteoclast lacuna.

Also disclosed are isolated nucleic acid molecules comprising a sequence encoding a replication site and a means for binding osteoblasts, osteoclasts, and/or osteoclast lacunae.

The means for binding osteoblasts, osteoclasts, and/or osteoclast lacuna can be any means capable of binding osteoblasts, osteoclasts, and/or osteoclast lacuna as discussed herein. For example, the peptides disclosed in SEQ ID NOs: 19-36, in particular SEQ ID NO:23 are means for binding osteoblasts, osteoclasts, and/or osteoclast lacuna.

Also disclosed are means for binding osteoblasts, osteoclasts, and/or osteoclast lacuna that do not comprise the peptides having the sequence set forth in SEQ ID NOs: 38 and 40.

3. Implants

The disclosed peptides and proteins can be attached to implants, such as bone and dental implants. A bone or dental implant is an object that is capable of being attached or fixed to bone. There are many different types of bone implants for many different situations and conditions. In addition there are many different ways to attach the implants to the bone or enhance the attachement of the implant to the bone. Likewise there are many different materials which can serve as implants, and many different types of devices can be attached to omplants. It is understood that any implant can be modified as discussed herein by the addition of the TRAP and TRAP variants, or the GPC4 or GPC4 variants or TRIP or TRIP variants or peptide or peptide variants as discussed herein. The disclosed compositions and methods help in implant attachment and the stimulation of bone growth in and around the implant because the disclosed compositions and methods in certain embodiments promote recruitment of osteoblasts and differentiation of osteoblasts. Examples of different bone implants and various materials and methods and devices related to implants can be found in the following U.S. patents, all of which are incorporated by reference for material related to implants: U.S. Pat. No. 6,447,545, Self-aligning bone implant;" U.S. Pat. No. 6,440,444, "Load bearing osteoimplant and method of repairing bone using the same;" U.S. Pat. No. 6,425,920, "Spinal fusion implant;" U.S. Pat. No. 6,413,089, "Immediate post-extraction implant;" U.S. Pat. No. 6,409,730, "Humeral spiral blade;" U.S. Pat. No. 6,406,296, "Implant with enlarged proximal segment;" U.S. Pat. No. 6,398,786, "Strain-inducing conical screw for stimulating bone transplant growth;" U.S. Pat. No. 6,379,153, "Dental implant having a dual-textured exterior surface;" U.S. Pat. No. 6,370,418, "Device and method for measuring the position of a bone implant;" U.S. Pat. No. 6,364,663, "Tooth implant and method to make it;" U.S. Pat. No. 6,350,283, "Bone hemi-lumbar interbody spinal implant having an asymmetrical leading end and method of installation thereof;" U.S. Pat. No. 6,350,126, "Bone implant;" U.S. Pat. No. 6,343,930, "Ceramic dental abutments with a metallic core;" U.S. Pat. No. 6,312,468, "Silicon-substituted apatites and process for the preparation thereof, ";" U.S. Pat. No. 6,309,220, "Bone distention and condensation dental implant distractor apparatus and method;" U.S. Pat. No. 6,302,913, "Biomaterial and bone implant for bone repair and replacement;" U.S. Pat. No. 6,287,115, "Dental implant and tool and method for effecting a dental restoration using the same;" U.S. Pat. No. 6,283,997, "Controlled architecture ceramic composites by stereolithography;" U.S. Pat. No. 6,280,478, "Artefact suitable for use as a bone implant;" U.S. Pat. No. 6,267,785, "Apparatus for positioning a prosthetic element to achieve a desired orientation for cementation;" U.S. Pat. No. 6,264,656, "Threaded spinal implant;" U.S. Pat. No. 6,261,288, "Implant stabilization and locking system;" U.S. Pat. No. 6,241,769, "Implant for spinal fusion;" U.S. Pat. No. 6,238,435, "Assembly tool for prosthetic implant;" U.S. Pat. No. 6,227,858, "Bone anchoring element;" U.S. Pat. No. 6,221,111, "Bioactive surface layer for bone implants;" U.S. Pat. No. 6,217,617, "Bone implant and method of securing;" U.S. Pat. No. 6,213,775, "Method of fastening an implant to a bone and an implant therefor;" U.S. Pat. No. 6,206,924, "Three-dimensional geometric bio-compatible porous engineered structure for use as a bone mass replacement or fusion augmentation device;" U.S. Pat. No. 6,193,762, "Surface for use on an implantable device;" U.S. Pat. No. 6,193,719, "Threaded clamping plug for interconnecting two implants of a spinal osteosynthesis instrumentation or other implants;" U.S. Pat. No. 6,187,009, "Osteosynthesis implant;" U.S. Pat. No. 6,168,436, "Universal dental implant abutment system;" U.S. Pat. No. 6,168,435, "Ceramic dental abutments with a metallic core;" U.S. Pat. No. 6,162,258, "Lyophilized monolithic bone implant and method for treating bone;" U.S. Pat. No. 6,149,432, "Buttress thread dental implant;" U.S. Pat. No. 6,146,384, "Orthopedic fixation device and method of implantation;" U.S. Pat. No. 6,136,038, "Bone connective prosthesis and method of forming same;" U.S. Pat. No. 6,096,080, "Apparatus for spinal fusion using implanted devices;" U.S. Pat. No. 6,090,998, "Segmentally demineralized bone implant;" U.S. Pat. No. 6,074,394, "Targeting device for an implant;" U.S. Pat. No. 6,059,832, "Prosthetic wrist implants, instruments, and related methods of implantation;" U.S. Pat. No. 6,058,590, "Apparatus and methods for embedding a biocompatible material in a polymer bone implant;" U.S. Pat. No. 6,056,750, "Fixing element for osteosynthesis;" U.S. Pat. No. 6,048,344, "Threaded washer and bone screw apparatus;" U.S. Pat. No. 6,046,164, "Therapeutic agent for diseases of periodontal tissue;" U.S. Pat. No. 6,032,677, "Method and apparatus for stimulating the healing of medical implants;" U.S. Pat. No. 6,025,538," Compound bone structure fabricated from allograft tissue;", "U.S. Pat. No. 6,004,327, "Ratcheting compression device;" U.S. Pat. No. 5,976,149, "Method and apparatus for aligning a prosthetic element;" U.S. Pat. No. 5,964,766, "Buttress thread implant;" U.S. Pat. No. 5,961,328, "Dental implant;" U.S. Pat. No. 5,951,564, "Orthopaedic positioning apparatus;" U.S. Pat. No. 5,944,721, "Method for repairing fractured bone;" U.S. Pat. No. 5,938,443, "Impression coping for use in an open tray and closed tray impression methodology;" U.S. Pat. No. 5,921,774, "Supporting body for use in orthodontic appliance and method;" U.S. Pat. No. 5,895,425, "Bone implant;" U.S. Pat. No. 5,885,287, "Self-tapping interbody bone implant;" U.S. Pat. No. 5,881,443, "Apparatus and methods for embedding a biocompatible material in a polymer bone implant;" U.S. Pat. No. 5,876,453, "Implant surface preparation;" U.S. Pat. No. 5,842,865, "Self-tapping implant with multiple concave tapping channels;" U.S. Pat. No. 5,836,768, "Fastening device for fixing orthodontic apparatuses on a dental implant;" U.S. Pat. No. 5,823,777, "Dental implants to optimize cellular response;" U.S. Pat. No. 5,800,550, "Interbody fusion cage;" U.S. Pat. No. 5,788,976, "Method for effecting bone repair;" U.S. Pat. No. 5,769,854, "Instrument system for preparing a distal femur for a posteriorly stabilized femoral component of a knee prosthesis;" U.S. Pat. No. 5,755,799, "Joint implant with self-engaging attachment surface;" U.S. Pat. No. 5,741,256, "Helical osteosynthetic implant;" U.S. Pat. No. 5,739,176, "Biodegradable in-situ forming implants and methods of producing the same;" U.S. Pat. No. 5,738,521, "Method for accelerating osseointegration of metal bone implants using electrical stimulation;" U.S. Pat. No. 5,709,547, "Dental implant for anchorage in cortical bone;" U.S. Pat. No. 5,702,695, "Osseointegration promoting implant composition, implant assembly and method therefor;" U.S. Pat. No. 5,702,475, "Modular bone implant with pan and pins;" U.S. Pat. No. 5,702,470, "Prosthetic wrist implant and related method of implantation;" U.S. Pat. No. 5,697,779, "Temporary implant for use as an anchor in the mouth;" U.S. Pat. No. 5,693,099, "Endoprosthesis;" U.S. Pat. No. 5,693,098, "Fibrin D-domain multimer prostheses and methods for their production;" U.S. Pat. No. 5,691,305, "Bone implant composition comprising a porous matrix, bone growth promoter proteins, and phosphotyrosyl protein phosphatase inhibitor;" U.S. Pat. No. 5,674,288, "Implant with transponder marker;" U.S. Pat. No. 5,665,089, "Bone fixation system;" U.S. Pat. No. 5,628,630, "Design process for skeletal implants to optimize cellular response;" U.S. Pat. No. 5,626,579, "Bone transport and lengthening system;" U.S. Pat. No. 5,624,462, "Bone implant and method of securing;" U.S. Pat. No. 5,609,636, "Spinal implant;" U.S. Pat. No. 5,609,631, "Fibrin D-domain multimer coated prostheses and methods for their production;" U.S. Pat. No. 5,601,558, "Soft tissue anchors and systems for implantation;" U.S. Pat. No. 5,580,246, "Dental implants and methods for extending service life;" U.S. Pat. No. 5,573,401, "Biocompatible, low modulus dental devices;" U.S. Pat. No. 5,571,198, "Acetabular shell with selectively available bone screw holds;" U.S. Pat. No. 5,571,185, "Process for the production of a bone implant and a bone implant produced thereby;" U.S. Pat. No. 5,564,925, "Implant for an artificial tooth;"

U.S. Pat. No. 5,558,517, "Polymeric prosthesis having a phosphonylated surface;" U.S. Pat. No. 5,555,884, "Measuring method by using resonance of a resonance medium;" U.S. Pat. No. 5,545,226, "Implants for cranioplasty;" U.S. Pat. No. 5,542,847, "Method, apparatus and device for dental prosthesis implantation;" U.S. Pat. No. 5,523,348, "Method of preparing collagen-polymer conjugates;" U.S. Pat. No. 5,514,137, "Fixation of orthopedic devices;" U.S. Pat. No. 5,507,829, "Set of fixation stems having similar stiffness;" U.S. Pat. No. 5,507,815, "Random surface protrusions on an implantable device;" U.S. Pat. No. 5,503,558, "Osseointegration promoting implant composition, implant assembly and method therefor;" U.S. Pat. No. 5,449,291, "Dental implant assembly having tactile feedback;" U.S. Pat. No. 5,397,358, "Bone implant;" U.S. Pat. No. 5,397,235, "Method for installation of dental implant;" U.S. Pat. No. 5,395,374, "Orthopedic cabling method and apparatus;" U.S. Pat. No. 5,387,243, "Method for converting a cementable implant to a press fit implant;" U.S. Pat. No. 5,370,693, "Orthopedic implant augmentation and stabilization device;" U.S. Pat. No. 5,336,465, "Method of making bone-implants;" U.S. Pat. No. 5,306,306, "Method for periprosthetic bone mineral density measurement;" U.S. Pat. No. 5,300,120, "Implant with electrical transponder marker;" U.S. Pat. No. 5,290,291, "Method for implant removal;" U.S. Pat. No. 5,282,746, "Method of installing a dental prosthesis;" U.S. Pat. No. 5,258,098, "Method of production of a surface adapted to promote adhesion;" U.S. Pat. No. 5,236,459, "Bone implant and method of making same;" U.S. Pat. No. 5,236,359, "Tapping tool and method for implant dentistry;" U.S. Pat. No. 5,221,204, "Dental implant product and method of making;" U.S. Pat. No. 5,201,735, "Apparatus and method for treating a fracture;" U.S. Pat. No. 5,190,546, "Medical devices incorporating SIM alloy elements;" U.S. Pat. No. 5,190,544, "Modular femoral fixation system;" U.S. Pat. No. 5,181,926, "Bone implant having relatively slidable members;" U.S. Pat. No. 5,171,327, "Bone implant;" U.S. Pat. No. 5,147,408, "Prosthetic device and method of implantation;" U.S. Pat. No. 5,108,453, "Bone implant;" U.S. Pat. No. 5,084,050, "Implant for bone reinforcement and for anchoring bone screws, implants and implant parts;" U.S. Pat. No. 5,066,296, "Apparatus for treating a fracture;" U.S. Pat. No. 5,024,239, "Method and apparatus for determining osseous implant fixation integrity;" U.S. Pat. No. 5,024,232, "Novel radiopaque heavy metal polymer complexes, compositions of matter and articles prepared therefrom;" U.S. Pat. No. 5,013,314, "Instrumentation and method for inserting flexible implants into fractured bones;" U.S. Pat. No. 5,006,070, "Dental implant with y-shaped body;" U.S. Pat. No. 5,002,580, "Prosthetic device and method of implantation;" U.S. Pat. No. 5,002,575, "Bone implant prosthesis;" U.S. Pat. No. 4,997,383, "Dental implant;" U.S. Pat. No. 4,990,163, "Method of depositing calcium phosphate cermamics for bone tissue calcification enhancement;" U.S. Pat. No. 4,990,161, "Implant with resorbable stem;" U.S. Pat. No. 4,978,355, "Plastic bone implant having a reinforced contact surface;" U.S. Pat. No. 4,976,739, "Implant system;" U.S. Pat. No. 4,976,738, "Porous metal overlay for an implant surface;" U.S. Pat. No. 4,969,908, "Lunate implant and method of stabilizing same;" U.S. Pat. No. 4,969,907, "Metal bone implant;" U.S. Pat. No. 4,969,904, "Bone implant;" U.S. Pat. No. 4,955,911, "Bone implant;" U.S. Pat. No. 4,936,855, "Stepped-lock ring system for implantable joint prostheses;" U.S. Pat. No. 4,936,851, "Analytic bone implant;" U.S. Pat. No. 4,919,666, "Implant having recesses for therapeutically effective substances;" U.S. Pat. No. 4,904,264, "Artifical joint system;" U.S. Pat. No. 4,904,187, "Dental implant;" U.S. Pat. No. 4,883,492, "Metal bone implant;" U.S. Pat. No. 4,877,020, "Apparatus for bone graft;" U.S. Pat. No. 4,865,602, "Gamma irradiation of collagen/mineral mixtures;" U.S. Pat. No. 4,854,873, "Oral implant;" U.S. Pat. No. 4,851,008, "Bone implant prosthesis with substantially stress-free outer surface;" U.S. Pat. No. 4,842,606, "Bone implant;" U.S. Pat. No. 4,834,757, "Prosthetic implant;" U.S. Pat. No. 4,828,563, "Implant;" U.S. Pat. No. 4,801,299, "Body implants of extracellular matrix and means and methods of making and using such implants;" U.S. Pat. No. 4,800,639, "Method of making a metal bone implant;" U.S. Pat. No. 4,793,335, "Bone implant for fixing artificial tendons or ligaments with application and extraction means;" U.S. Pat. No. 4,790,849, "Malar implant and method of inserting the prothesis;" U.S. Pat. No. 4,784,124, "Bone implant for prostheses and tool for inserting the implant into a bone;" U.S. Pat. No. 4,781,721, "Bone-graft material and method of manufacture;" U.S. Pat. No. 4,781,591, "Endosteal implant and method for performing implantation thereof;" U.S. Pat. No. 4,776,330, "Modular femoral fixation system;" U.S. Pat. No. 4,768,956, "Dental implant;" U.S. Pat. No. 4,753,657, "Fixation of implants in bone;" U.S. Pat. No. 4,752,295, "Metal bone implant;" U.S. Pat. No. 4,744,754, "Dental implant and method for installing same into bone tissue;" U.S. Pat. No. 4,722,948, "Bone replacement and repair putty material from unsaturated polyester resin and vinyl pyrrolidone;" U.S. Pat. No. 4,718,914, "Metal bone implant;" U.S. Pat. No. 4,713,004, "Submergible screw-type dental implant and method of utilization;" U.S. Pat. No. 4,713,003, "Fixture for attaching prosthesis to bone;" U.S. Pat. No. 4,687,486, "Implant, particularly endoprosthesis;" U.S. Pat. No. 4,677,972, "Coupling assembly for joining an implant tool to a bone implant;" U.S. Pat. No. 4,658,808, "Arrangement for preparing an anatomically measured endoprosthesis;" U.S. Pat. No. 4,650,109, "Method of manufacture of bone implant porous surfaces;" U.S. Pat. No. 4,645,505, "Wrist implant;" U.S. Pat. No. 4,645,503, "Moldable bone-implant material;" U.S. Pat. No. 4,619,655, "Plaster of Paris as a bioresorbable scaffold in implants for bone repair;" U.S. Pat. No. 4,599,085, "Bone implant member for prostheses and bone connecting elements and process for the production thereof;" U.S. Pat. No. 4,599,084, "Method of using biological tissue to promote even bone growth;" U.S. Pat. No. 4,576,152, "Injector for bone cement;" U.S. Pat. No. 4,571,185, "Retaining device for removable dental prostheses;" U.S. Pat. No. 4,570,271, "Porous coatings from wire mesh for bone implants;" U.S. Pat. No. 4,548,959, "Hydroxyapatite, ceramic material and process for preparing thereof;" U.S. Pat. No. 4,538,304, "Bone implant;" U.S. Pat. No. 4,530,116, "Anchoring shank for a bone implant;" U.S. Pat. No. 4,484,570, "Device comprising an implant and screws for fastening said implant to a bone, and a device for connecting two separated pieces of bone;" U.S. Pat. No. 4,472,840, "Method of inducing osseous formation by implanting bone graft material;" U.S. Pat. No. 4,406,623, "Screw-type bone implant for receiving a dental prosthesis;" U.S. Pat. No. 4,336,618, "Bone connective prostheses adapted to maximize strength and durability of prostheses-bone cement interface; and methods of forming same;" U.S. Pat. No. 4,279,598, "Dental half-implants;" U.S. Pat. No. 4,278,091, "Soft tissue retainer for use with bone implants, especially bone staples;" U.S. Pat. No. 4,272,855, "Anchoring surface for a bone implant;" U.S. Pat. No. 4,270,905, "Replacement system for dental and other bone implants;" U.S. Pat. No. 4,244,689, "Endosseous plastic implant;" U.S.

Pat. No. 4,237,559, "Bone implant embodying a composite high and low density fired ceramic construction;" U.S. Pat. No. 4,227,265, "Bone implant with plastic insert between elements of different mechanical properties;" U.S. Pat. No. 4,199,824, "Intramedullary stem;" U.S. Pat. No. 4,179,809, "Dental implant;" U.S. Pat. No. 4,171,544, "Bonding of bone to materials presenting a high specific area, porous, silica-rich surface;" U.S. Pat. No. 4,164,793, "Lunate implant;" U.S. Pat. No. 4,156,943, "High-strength porous prosthetic device and process for making the same;" U.S. Pat. No. 4,155,124, "Burnt ceramic bone implant;" U.S. Pat. No. 4,131,597, "Bioactive composite material process of producing and method of using same;" U.S. Pat. No. 4,120, 298, "Implant to secure the greater trochanter;" U.S. Pat. No. 4,109,382, "Enossal implant;" U.S. Pat. No. 4,024,638, "Wide vent dental implants;" U.S. Pat. No. 4,012,796, "Interpositioning collar for prosthetic bone insert;" U.S. Pat. No. 4,000,525, "Ceramic prosthetic implant suitable for a knee joint plateau;" U.S. Pat. No. 3,981,079, "Dental implant and method of mounting the same in the jaw bone;" and U.S. Pat. No. 3,973,277, "Attaching fibrous connective tissue to bone."

It is understood that in certain embodiments, the proteins or peptides attached to the implant can be cleavable from the implant. In these embodiments the peptide or protein is attached to the implant such that the peptide or protein can be removed from the implant over time or in certain conditions. For example, this type of embodiment can further enhance diffusion of the molecules for the purpose of inducing differentiation of osteoblasts near the implant because it allows for the importation of the TRAP or TRAP fragment or TRAP like molecule into the cell to promote interaction with TRIP. There are many systems and reagents for attaching proteins or peptides to surfaces in a non-permanent manner.

For example, U.S. Pat. No. 6,416,758, which is herein incorporated by reference for material related to linkers for peptides discusses biochemical cross linkers and peptidase cross linkers. U.S. Pat. No. 6,416,758 provides different heterofunctional biochemical cross linkers which can be used to link peptides to other peptide or surfaces which are able to react with one of the reactive groups on the cross linker. For example, various hetero-bi-functional cross linkers discussed in U.S. Pat. No. 6,416,758 are SMPT, SPDP, LC-SPDP, Sulfo-LC-SPDP, SMCC, Sulfo-SMCC, MBS, Sulfo-MBS, SIAB, Sulfo-SIAB, SMPB, Sulfo-SMPB, EDC/Sulfo-NHS, and ABH. The key aspect of hetero-bi-functional linkers is that there is typically one group that reacts with a primary amine (e.g., N-hydroxy succinimide), for example, the primary amine present on most proteins and petides, and another group that reacts with a thiol group (e.g., pyridyl disulfide, maleimides, halogens, etc.), which could be for example, present on the implant. For example, primary or secondary amine groups, hydrazide or hydrazine groups, carboxyl alcohol, phosphate, or alkylating groups may be used for binding or cross-linking.

It is understood that the linking groups may have a spacer arm, or linker, between them, which may be any length appropriate for the situation. These various cross linkers and others have a variety of stabilities in vivo, in the presence of blood, for example, and linkers can be utilized which have more or less stability in vivo, to achieve a lesser or greater release respectively. These types of linkers are termed biologically releaseable linkers. For example, linkers can be utilized which are acid cleavable. A biologically-releasable linker includes all linkages that are releasable, cleavable or hydrolyzable only or preferentially under certain conditions. This includes disulfide and trisulfide bonds and acid-labile bonds, as described in U.S. Pat. Nos. 5,474,765 and 5,762, 918, each specifically incorporated herein by reference at least for material related to linkers. Biologically releasable linkers can also have enzyme-sensitive bonds, including peptide bonds, esters, amides, phosphodiesters and glycosides, which allow for the cleavage by enzymes or environmental conditions. For example, there are numerous proteases that exist, particularly at the site bone resorption and formation, and these proteases are typically activated in an acidic environment. There are also many proteases t t are circulating, such as proteases involved in the blood coagulation system. For example, peptide linkers that include a cleavage site for urokinase, pro-urokinase, plasmin, plasminogen, TGF.beta., staphylokinase, Thrombin, Factor IXa, Factor Xa or a metalloproteinase, such as an interstitial collagenase, a gelatinase or a stromelysin, exist and are discussed in U.S. Pat. Nos. 6,004,555 and 5,877,289 which are herein incorporated by reference at least for material related to linkers and biologically releasable bonds. These patents discuss the use of linkers typically in the context of tumor cell envronments, but can be adapted for use with the disclosed implants. An exemplary list of cleavable linker sequences set forth in U.S. Pat. No. 6,416,758 is: Plasmin cleavable sequences, such as Pro-urokinase (PRFKIIGG, SEQ ID NO:51, PRFRIIGG, SEQ ID NO:52); TGFβ (SS-RHRRALD, SEQ ID NO:53); Plasminogen (RKSSIIIRM-RDVVL, SEQ ID NO:54); Staphylokinase (SSSFD-KGKYKKGDDA, SEQ ID NO:55, SSSFDKGKYKRGDDA, SEQ ID NO:56); Factor Xa cleavable sequences (IEGR, SEQ ID NO:57, IDGR, SEQ ID NO:58, GGSIDGR, SEQ ID NO:59); MMP cleavable sequences, such as Gelatinase A (PLGLWA, SEQ ID NO:60); Collagenase cleavable sequences such as Calf skin collagen (α1(I) chain) (GPQGIAGQ, SEQ ID NO:61), Calf skin collagen (α2(I) chain) (GPQGLLGA, SEQ ID NO:62), Bovine cartilage collagen (α1(II) chain) (GIAQQ, SEQ ID NO:63); Human liver collagen (α1(III) chain) (QPLG-TIAGI, SEQ ID NO:64), Human $α_2$ M (GPEGLRVG, SEQ ID NO:65), Human PZP (YGAGLGVV, SEQ ID NO:66, AGLGVVER, SEQ ID NO:67, AGLGISST, SEQ ID NO:68), Rat $α_1$ M (EPQALAMS, SEQ ID NO:69, QALAMSAI, SEQ ID NO:70), Rat $α_2$ M (AAYHLVSQ, SEQ ID NO:71, MDAFLESS, SEQ ID NO:72), Rat $α_1$ $I_3$ (2J) (ESLPVVAV, SEQ ID NO:73), Rat $α_1$ $I_3$ (27J) (SAPA-VESE, SEQ ID NO:74), Human fibroblast collagenase (autolytic cleavages) (DVAQFVLT, SEQ ID NO:75, VAQFV-LTE, SEQ ID NO:76, AQFVLTEG, SEQ ID NO:77, PVQPIGPQ, SEQ ID NO:78). These are examples of cleavable peptide linkers and they can be adapted for use with the disclosed implants and compositions.

It is understood that any biologically releasable linker can be used with the implants disclosed herein, as long as the linkers allow for the release of the peptide or protein such that it can interact with TRAP, TRIP, or GPC4.

4. Nucleic Acids

Nucleic acid molecules that encode peptides that bind TRAP and osteoclast lacuna are disclosed. Nucleic acid molecules that encode peptides that can inhibit osteoblasts from interacting with osteoclast lacuna are disclosed. Also disclosed are nucleic acid molecules that encode proteins expressed in osteoblasts, such as TRIP and GPC4, which interact with TRAP.

Disclosed are isolated nucleic acid molecules comprising a sequence set forth in SEQ ID NO:1, SEQ ID NO:2, SEQ ID NO:3, SEQ ID NO:4, SEQ ID NO:5, SEQ ID NO:6,SEQ ID NO:7,SEQ ID NO:8,SEQ ID NO:9,SEQ ID NO:10,SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:37, SEQ ID NO:39, or SEQ ID NO:41.

Disclosed are isolated nucleic acid molecules comprising a complement to a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:37, SEQ ID NO:39, or SEQ ID NO:41.

Also disclosed are isolated nucleic acid molecules comprising a sequence having at least 80% identity to a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:37, SEQ ID NO:39, or SEQ ID NO:41.

Disclosed are isolated nucleic acid molecules comprising a sequence having at least 80% identity to a complement to a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 SEQ ID NO:18, or SEQ ID NO:37, SEQ ID NO:39, or SEQ ID NO:41.

Disclosed are isolated nucleic acid molecules comprising a sequence that hybridizes under stringent hybridization conditions to a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:37, SEQ ID NO:39, or SEQ ID NO:41.

Also disclosed are isolated nucleic acid molecules comprising a sequence that hybridizes under stringent hybridization conditions to a complement of a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:37, SEQ ID NO:39, or SEQ ID NO:41.

Disclosed are isolated nucleic acid molecules comprising a sequence encoding a peptide set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:38, SEQ ID NO:40, or SEQ ID NO:42.

Disclosed are isolated nucleic acid molecules comprising a sequence encoding a peptide having at least 80% identity to a peptide set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:35, SEQ ID NO:38, SEQ ID NO:40, or SEQ ID NO:42.

Also disclosed are isolated nucleic acid molecules comprising a sequence encoding a peptide having at least 80% identity to a peptide set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:35, SEQ ID NO:38, SEQ ID NO:40, or SEQ ID NO:42, wherein any change from SEQ ID Nos:19-36, SEQ ID NO:35, SEQ ID NO:38, SEQ ID NO:40, or SEQ ID NO:42. is a conservative change.

Also disclosed are isolated nucleic acid molecules that encode a peptide, wherein the encoded peptide binds an osteoclast cell, isolated nucleic acid molecules that encode a peptide, wherein the encoded peptide binds an osteoclast lacuna, isolated nucleic acid molecules that encode a peptide, wherein the encoded peptide binds a lysosomal protein expressed in osteoclasts, and isolated nucleic acid molecules, wherein the encoded peptide binds the lysosomal protein, tartrate resistant acid phosphatase. Other known lysosomal proteins are for example, the family of cathepsin enzymes, galactosidase and glucosidase enzymes, lysozyme, tartrate sensitive acid phosphatase (TSAP).

Disclosed are isolated nucleic acid molecules, wherein the encoded peptide binds with a $K_d$ less than or equal to $10^{-5}$, less than or equal to $10^{-6}$, less than or equal to $10^{-7}$, less than or equal to $10^{-8}$, less than or equal to $10^{-9}$, less than or equal to $10^{-10}$, less than or equal to $10^{-11}$, or less than or equal to $10^{-12}$.

Disclosed are primers comprising a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO: 16, SEQ ID NO:17, SEQ ID NO:18, SEQ ID NO:37, SEQ ID NO:39, or SEQ ID NO:41 or a portion thereof.

Disclosed are primers comprising a sequence which is a complement to a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO:39, or SEQ ID NO:41 or a portion thereof.

Disclosed are primers comprising a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO:39, or SEQ ID NO:41.

Disclosed are primers comprising a sequence which is a complement to a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO:39, or SEQ ID NO:41.

Disclosed are primers and probes that comprise a potion of the sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO:39, or SEQ ID NO:41.

Disclosed are vectors comprising a nucleic acid set forth in any one of claims SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO:39, or SEQ ID NO:41.

Also disclosed are vectors comprising a nucleic acid having at least a 80%, 85%, 90, or 95% identity to or hybridize under stringent conditions to a sequence set forth in any one of claims SEQ ID NO:1, SEQ ID NO:2, SEQ ID NO:3, SEQ ID NO:4, SEQ ID NO:5, SEQ ID NO:6, SEQ D NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO:39, or SEQ ID NO:41.

Also disclosed are cells comprising any of the non-naturally occurring disclosed nucleic acids. Non-naturally occurring means occurring in a cell in a way that has been affected by a recombinant molecular biology technique or delivery of the composition to the cell.

Also disclosed are cells, wherein the cell is selected from the group consisting of a fibroblast cell, a cartilage cell, a bone cell, bone marrow cell, a stem cell, and an adipocyte cell, osteoblast cell.

Also disclosed are cells, wherein the exogenous nucleic acid in the cell is under the control of a cell specific promoter. Also disclosed are cells, wherein the cell specific promoter is a bone cell specific promoter such as, type I collagen, alkaline phosphatase, osteonectin, osteocalcin, and the cbfa1 promoter.

Also disclosed are implants for promoting bone growth, wherein the implant comprises the cells disclosed herein or the peptides and proteins disclosed herein.

Also disclosed are animals comprising any of the non-naturally occurring nucleic acids disclosed.

Also disclosed are microarrays comprising any of the nucleic acids disclosed herein.

Disclosed are pharmaceutical compositions comprising any of the nucleic acids disclosed herein along with pharmaceutically acceptable carrier.

Also disclosed are isolated nucleic acid molecules, wherein the identity is at least 81%, 82%, 83%, 84%, 85%, 86%, 87%, 88%, 89%, 90%, 91%, 92%, 93%, 94%, 95%, 96%, 97%, 98%, 99% to any of the disclosed nucleic acid sequences wherein the disclosed nucleic acid sequence is not SEQ ID NOs:37, 39, and 41.

a) Sequence Similarities

Disclosed are nucleic acids and peptides that are involved in interactions and modulating interactions that can occur between osteoblasts and osteoclasts/osteoclast lacuna, and peptides that are expressed by osteoblasts and osteoclasts. It is understood that the disclosed nucleic acids and peptides can be defined by the homology or identity that they have to particular sequences or variants of the disclosed compositions.

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

b) Hybridization/Selective Hybridization

Disclosed are nucleic acids and it is understood that nucleic acids have certain properties, among them the ability to interact in a sequence specific manner, termed hybridization. The level or amount of hybridization that occurs between nucleic acids is understood to be one way to define the relationship between those two nucleic acids.

The term hybridization typically means a sequence driven interaction between at least two nucleic acid molecules, such as a primer or a probe and a gene. Sequence driven interaction means an interaction that occurs, for example, between two nucleotides or nucleotide analogs or nucleotide derivatives or nucleotide substitutions, in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 3rd Ed., Cold Spring Harbor Laboratory, Cold Spring Harbor, N.Y., 2001; Kunkel et al. Methods Enzymol. 1987:154: 367, 1987 which are herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed under conditions where both the limiting and non-limiting primer are for example, 10 fold or 100 fold or 1000 fold below their $K_d$, or where only one of the nucleic acid molecules is 10 fold or 100 fold or 1000 fold or where one or both nucleic acid molecules are above their $K_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

c) Nucleotides and Related Molecules

These discussion of nucleotides and nucleotide related molecules are not meant to be limiting, but rather are exemplary of the wide range of compositions that are related to nucleotide molecules.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMF (3'-adenosine monophosphate) or 5'-GMP (5'-guanosine monophosphate).

It is understood when the terms "nucleotide" or "nucleotides" are used that nucleotide analogs, nucleotides substitutions, any other nucleotide related molecules are contemplated unless specifically indicated to the contrary.

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil- 5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often base modifications can be combined with for example a sugar modification, such as 2'-O-methoxyethyl, to achieve unique properties such as increased duplex stability. There are numerous United States Patent Nos. such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the allyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[$(CH_2)_n$O]$_m$ $CH_3$, —O$(CH_2)_n$ $OCH_3$, —O$(CH_2)_n$ $NH_2$, —O$(CH_2)_n$ $CH_3$, —O$(CH_2)_n$—$ONH_2$, and —O$(CH_2)_n$ON[$(CH_2)_n$ $CH_3)]_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacolcinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and amninoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289;

5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al, Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexyla-mino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

Nucleic acids are typically made up of nucleotides, nucleotide analogs, or nucleotide substitutions, or combinations thereof.

d) Sequences

Disclosed are nucleic acids and peptides. Certain disclosed nucleic acids, encode peptides that have a particular function, such as binding TRAP, increasing osteoblast binding to TRAP and to osteoclast and/or osteoclast lacuna, or inhibiting osteoblast binding to osteoclast lacuna, in for example a competitive binding reaction with TRAP or osteoclasts or osteoclast lacuna. Other disclosed nucleic acids can themselves either inhibit or affect the interactions between osteoblasts and osteoclast lacuna or TRAP, for example, such as aptamers, or that can effect the expression of various nucleic acids, such as antisense molecules. Other nucleic acids that are disclosed are related to genes that produce proteins expressed in either osteoclasts or osteoblasts, for example.

For example, there are a variety of sequences related to the GPC4 gene (nucleic acid is SEQ ID NO:37, peptide sequence is SEQ ID NO:38) having the following Genbank Accession Number: XM_029542, and the TRIP gene (nucleic acid is SEQ ID NO:39 and peptide is SEQ ID NO:40) having Genbank accession number U36764 these sequences and others are herein incorporated by reference in their entireties as well as for individual subsequences contained therein.

One particular sequence, set forth in SEQ ID NO:37 and having Genbank accession number XM_029542 is used herein, as an example, to exemplify the disclosed compositions and methods. It is understood that the description related to this sequence is applicable to any sequence related to GPC4 or TRIP or any other disclosed sequence unless specifically indicated otherwise. Those of skill in the art understand how to resolve sequence discrepancies and differences and to adjust the compositions and methods relating to a particular sequence to other related sequences (i.e. sequences of TRIP). Primers and/or probes can be designed for any GPC4 or TRI sequence or sequence disclosed herein, given the information disclosed herein and known in the art.

e) TRAP Binding Region GPC4

The GPC4 gene encodes a protein that contains a TRAP binding region, which is amino acids 252-263 of SEQ ID NO:38. This region has been shown to have a high degree of homology to clone 5, which is SEQ ID NO:23. It is understood that the region defined by amino acids 252-263 of the SEQ ID NO:38 represent one variant of a TRAP binding region, and that there are other variants which will function in binding TRAP. For example, this sequence indicates that there is a 5 amino acid stretch that is 100% conserved, amino acids 259-263 of SEQ ID NO:38. Thus, disclosed are isolated compositions that comprise amino acids 259-263 of SEQ ID NO:38, which function to bind TRAP or compositions which encode these amino acids. Also disclosed are isolated compositions that comprise amino acids 259-263 of SEQ ID NO:38, which function to bind TRAP or compositions which encode these amino acids which are non-natural proteins or nucleic acids. Also disclosed are compositions having the level of homology observed between SEQ ID NO:23 and SEQ ID NO:38. Furthermore, it is understood that there are regions for attachment to the cellular membrane. Variants, as discussed herein, are considered disclosed and described.

f) Primers and Probes

Disclosed are compositions including primers and probes, which are capable of interacting with the GPC4, TRIP, and TRAP genes or mRNAs or their complements or any other nucleic acid as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner.

The size of the primers or probes for interaction with, for example, GPC4 or TRIP or TRAP genes, mRNA or their complements in certain embodiments can be any size that supports the desired enzymatic manipulation of the primer, such as DNA amplification or the simple hybridization of the probe or primer. A typical GPC4 or TRIP or TRAP primer or probe, for example, would be at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a GPC4 or TRIP or TRAP primer or probe, for example, can be less than or equal to about 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the GPC4 or TRIP or TRAP typically will be used to produce an amplified DNA product. In general, typically the size of the product will be such that the size can be accurately determined to within 3, or 2 or 1 nucleotides.

In certain embodiments this product is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

g) Functional Nucleic Acids

Disclosed are compositions and methods that can involve functional nucleic acids, such as nucleic acids that affect the mRNA or interact with the mRNA of for example, GPC4, TRIP or TRAP. Other functional nucleic acids and methods of using them, may affect or interact with the genes of GPC4, TRIP, or TRAP. Other functional nucleic acids and methods of using them, may affect or interact with the function of the gene products of GPC4, TRIP, or TRAP. Also disclosed are methods of isolating and identifying the functional nucleic acids disclosed herein.

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of GPC4, TRIP, or TRAP or the genomic DNA of GPC4, TRIP, or TRAP or they can interact with the GPC4, TRIP, or TRAP polypeptide. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than $10^{-6}$. It is more preferred that antisense molecules bind with a $K_d$ less than $10^{-8}$. It is also more preferred that the antisense molecules bind the target molecule with a $K_d$ less than $10^{-10}$. It is also preferred that the antisense molecules bind the target molecule with a $K_d$ less than $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Antisense molecules that interact with the mRNA of GPC4 and TRIP or TRAP are disclosed. For example, antisense molecules to GPC4 are provided in Kleeff J. Wildi S. Kumbasar A. Friess H. Lander A D. Korc M. Stable transfection of a glypican antisense construct decreases tumorigenicity in PANC-1 pancreatic carcinoma cells. Pancreas. 19(3):281-8,1999 and Kleeff J. Wildi S. Kumbasar A. Friess H. Lander A D. Korc M. Stable transfection of a glypican-1 antisense construct decreases tumorigenicity in PANC-1 pancreatic carcinoma cells. Pancreas. 19(3):281-8, 1999 which are herein incorporated by reference at least for the material related to antisense of GPC4.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $K_d$ less than $10^{-6}$. It is more preferred that the aptamers bind the target molecule with a $K_d$ less than $10^{-8}$. It is also more preferred that the aptamers bind the target molecule with a $K_d$ less than $10^{-10}$. It is also preferred that the aptamers bind the target molecule with a $K_d$ less than $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $K_d$ with the target molecule at least 10 fold lower than the $K_d$ with a background binding molecule. It is more preferred that the aptamer have a $K_d$ with the target molecule at least 100 fold lower than the $K_d$ with a background binding molecule. It is more preferred that the aptamer have a $K_d$ with the target molecule at least 1000 fold lower than the $K_d$ with a background binding molecule. It is preferred that the aptamer have a $K_d$ with the target molecule at least 10000 fold lower than the $K_d$ with a background binding molecule. It is preferred when doing the comparison for a polypeptide for example, that the background molecule be a different polypeptide. For example, when determining the specificity of GPC4, TRIP, or TRAP aptamers, the background protein could be bovine serum albumin. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$. It is more preferred that the triplex forming molecules bind with a $K_d$ less than $10^{-8}$. It is also more preferred that the triplex forming molecules bind the target molecule with a $K_d$ less than $10^{-10}$. It is also preferred that the triplex forming molecules bind the target molecule with a $K_d$ less than $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci.* USA 89:8006-8010 (1992); WO 93/22434 by Yale; WO 95/24489 by Yale; Yuan and Altman, *EMBO J* 14:159-168 (1995), and *Carrara et al., Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162

5. Peptides

Disclosed are isolated peptides that bind TRAP. For example, disclosed are isolated peptides set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36.

Also disclosed are isolated peptides comprising at least 80% identity to a peptide set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36.

Also disclosed are isolated peptides comprising at least 80% identity to a peptide set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:3 1, SEQ ID NO:32, SEQ ID NO:33, SEQ ID NO:34, SEQ ID NO:35, or SEQ ID NO:36, wherein any change from the SEQ ID Nos:19-36 are conservative changes.

Also disclosed are isolated peptides, wherein the peptide binds an osteoclast cell and isolated peptides, wherein the peptides binds osteoclast lacuna and isolated peptides, wherein the peptide binds a lysosomal protein expressed in osteoclasts and isolated peptides, wherein the lysosomal protein is tartrate resistant acid phosphatase.

Disclosed are isolated peptides, wherein the peptides bind with a $K_d$ less than or equal to $10^{-5}$, wherein the peptides bind with a $K_d$ less than or equal to $10^{-6}$, wherein the peptides bind with a $K_d$ less than or equal to $10^{-7}$, wherein the peptides bind with a $K_d$ less than or equal to $10^{-8}$, wherein the peptides bind with a $K_d$ less than or equal to $10^{-9}$, wherein the peptides bind with a $K_d$ less than or equal to $10^{-10}$, wherein the peptides bind with a $K_d$ less than or equal to $10^{-11}$, wherein the peptides bind with a $K_d$ less than or equal to $10^{-12}$.

Also disclosed are cells comprising any of the non-naturally occurring disclosed peptides. Non-naturally occurring means occurring in a cell in a way that has been affected by a recombinant molecular biology technique or delivery of the composition to the cell.

Also disclosed are animals comprising any of the non-naturally occurring disclosed peptides.

Disclosed are pharmaceutical compositions comprising any of the disclosed peptides and a pharmaceutically acceptable carrier.

Disclosed are isolated peptides, wherein the peptide inhibits the binding of an osteoblast to an ostcoclast lacuna.

Also disclosed are isolated peptides, wherein the peptides have a $K_d$ of inhibition less than or equal to $10^{-5}$ and, wherein the peptides have a $K_d$ of inhibition less than or equal to $10^{-6}$ and, wherein the peptides have a $K_d$ of inhibition less than or equal to $10^{-7}$ and, wherein the peptides have a $K_d$ of inhibition less than or equal to $10^{-8}$ and, wherein the peptides have a $K_d$ of inhibition less than or equal to $10^{-9}$ and, wherein the peptides have a $K_d$ of inhibition less than or equal to $10^{-10}$ and, wherein the peptides have a $K_d$ of inhibition less than or equal to $10^{-11}$ and, wherein the peptides have a $K_d$ of inhibition less than or equal to $10^{-12}$.

Also disclosed are isolated peptides, wherein the identity is at least 81%, 82%, 83%, 84%, 85%, 86%, 87%, 88%, 89%, 90%, 91%, 92%, 93%, 94%, 95%, 96%, 97%, 98%, or 99%.

a) Protein Variants

As discussed herein there are numerous variants of the protein and polypeptides set forth in SEQ ID NOs: 19-36, 38, 40, and 42 that are known and herein contemplated. In addition, to the naturally occurring fuictional variants in SEQ ID NOs: 38, 40, and 42 that are homolog variants (varying species for example) there are non-naturally occurring variant of the in SEQ ID NOs: 19-36, 38, 40, and 42 proteins which also finction in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions can generally be made as conservative substitutions which generally are made in accordance with the following Tables 1 and 2.

TABLE 1

Amino Acid Abbreviations

| Amino Acid | Abbreviations | |
| --- | --- | --- |
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | K |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 2

Amino Acid Substitutions

| Original Residue | Exemplary Conservative Substitutions, others are known in the art. |
| --- | --- |
| Ala | ser |
| Arg | lys, gln |
| Asn | gln; his |
| Asp | glu |
| Cys | ser |
| Gln | asn, lys |
| Glu | asp |
| Gly | pro |
| His | asn; gln |
| Ile | leu; val |
| Leu | ile; val |
| Lys | arg; gln; |
| Met | Leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:23 sets forth a particular sequence of clone 5 and SEQ ID NO:38 sets forth a particular sequence of a GPC4 protein. Specifically disclosed are variants of these and other proteins herein disclosed which have at least 40 or 50 or 60 or 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 40% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:23 is set forth in SEQ ID NO:5. Another nucleic acid sequence that encodes the same protein sequence set forth in SEQ ID NO:23 is set forth in SEQ ID NO:43. In addition, for example, a disclosed conservative derivative of SEQ ID NO:23 is shown in SEQ ID NO: 44, where the valine (V) at position 12 is changed to a isoleucine (I). It is understood that for this mutation all of the nucleic acid sequences that encode this particular derivative of SEQ ID NO:23 are also disclosed including for example SEQ ID NO:45 and SEQ ID NO:46 which set forth two of the degenerate nucleic acid sequences that encode the particular polypeptide set forth in SEQ ID NO:44. For example, one of the many nucleic acid sequences that can encode the protein sequence set forth in SEQ ID NO:38 is set forth in SEQ ID NO:37. Another nucleic acid sequence that encodes the same protein sequence set forth in SEQ ID NO:38 is set forth in SEQ ID NO:47. In addition, for example, a disclosed conservative derivative of SEQ ID NO:38 is shown in SEQ ID NO: 48, where the G at position 5 is changed to an A. It is understood that for this mutation all of the nucleic acid sequences that encode this particular derivative of SEQ ID NO:48 are also disclosed including for example SEQ ID NO:49 and SEQ ID NO:50 which set forth two of the degenerate nucleic acid sequences that encode the particular polypeptide set forth in SEQ ID NO:48. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

b) GPC4

Glypican 4 is one member of a close family of heparan sulfate proteoglycan-containing plasma membrane receptors found on fibroblasts, periodontal ligament cells and mesenchymal and marrow stem cells (Worapamom W, Li H, Haas H R, Pujic Z, Ghrjes A A, Bartold P M (2000) Cell surface proteoglycan expression in human periodontal cells. Connective Tiss. Res. 41: 57-68 and Siebertz B, Stocker G, Drzeniek Z, Handt S, Just U, Haubeck H D (1999) Expression of glypican-4 in haematopoietic-progenitor and bone marrow stromal cells. Biochemical. J. 344:937-43). These receptors have been implicated in BMP signaling in Drosophila and as cytokine presenting receptors in bone marrow cells. Mutations in the glypican family lead to a syndrome known at Simpson-Golabi-Behmel syndrome (24.Pilia G, Huges-Benzi R M, MacKenzie A, Baybayan P, Chen E Y, Huber R, Neri G, Cao A, Forabosco A, Schlessinger D (1996) Mutatations in GPC, a glypican gene, cause the Simpson-Golabi-Behmel overgrowth syndrome. Nature Genetics 12:241-247). Mice with this syndrome demonstrate a varied phenotype, however, the one common feature is skeletal abnormalities. The phenotype is shortened limbs, malformed trabecular architecture and a compressed rib cage. Tooth development may also be affectes.

c) TRAP

TRAP is a lysomsomal protein that is expressed in osteoclast cells. TRAP is exported from the osteoclast cell and resides between the membrane of the osteoclast cell and the bone surface which is undergoing resorption.

There are upward of 20 characterized active lysosomal enzymes that participate in osteoclastic bone resorption which are discussed in Kremer M, Judd J, Rifkin B, Auszmann J, Oursler M J (1995) Estrogen modulation of osteoclast lysosomal enzyme secretion. Journal of Cellular Biochemistry. 57:271-9; Vaes G, Delaisse J M, Eeckhout Y (1992) Relative roles of collagenase and lysosomal cysteine-proteinases in bone resorption. Matrix Supplement. 1:383-8; Sasaki T, Ueno-Matsuda E (1993) Cysteine-proteinase localization in osteoclasts: an immunocytochemical study. Cell & Tissue Research. 27:177-9; Ohsawa Y, Nitatori T, Higuchi S, Kominami E, Uchiyama Y (1993) Lysosomal cysteine and aspartic proteinases, acid phosphatase, and an endogenous cysteine proteinase inhibitor, cystatin-beta, in rat osteoclasts. Journal of Histochemistry & Cytochemistry. 41:1075-83; Baron R(1989) Molecular mechanisms of bone resorption by the osteoclast. Anatomical Record. 224:317-24; Karhukorpi E K, Vihko P, Vaananen K (1992) A difference in the enzyme contents of resorption lacunae and secondary lysosomes of osteoclasts. Acta Histochemica. 92:1-11; Delaisse J M, Eeckhout Y, Vaes G (1985) Bisphosphonates and bone resorption: effects on collagenase and lysosomal enzyme excretion. Life Sciences. 37:2291-6; Baron R, Neff L, Tran Van P, Nefussi J R, Vignery A (1986) Kinetic and cytochemical identification of osteoclast precursors and their differentiation into multinucleated osteoclasts. American Journal of Pathology. 122:363-78; Ash P, Loutit J F, Townsend K M (1980) Giant lysosomes, a cytoplasmic marker in osteoclasts of beige mice. Journal of Pathology. 130:237-45; Lorenzo J A, Holtrop M E, Raisz L G (1984) Effects of phosphate on calcium release, lysosomal enzyme activity in the medium, and osteoclast morphometry in cultured fetal rat bones. Metabolic Bone Disease & Related Research. 5:187-90 which are herein incorporated by reference at least for material related to their cognate lysozymes.

Type V tartrate resistant acid phosphatase (TRAP) is present in a number of cell types, the most abundant of which may be active osteoclasts. In fact, TRAP is the acid hydrolase that has become a standardized marker for identification of this cell type (Hayman A R, et al., J. of Anatomy. 196:433-41 (2000); Tiffee J C, Aufdemorte T B,. Journal of Oral & Maxillofacial Surgery. 55:1108-12 (1997)). Moreover, we have known for many years that there is a polarized secretion of TRAP and other lysosomal enzymes by the osteoclast toward the bone surface (Baron R, et al., et al., Journal of Cell Biology. 106:1863-72.) and that these enzymes can be detected deep within bone matrix and at sites of resorption after the osteoclast has left the lacuna (Wergedal J E, Baylink D J, Journal of Histochemistry & Cytochemistry. 17:799-806 (1969); Yamamoto T, Nagai H Journal of Bone & Mineral Research. 7:1267-73 (1992)).

Maintenance of trabecular bone architecture is necessary to withstand mechanical forces and stresses and to resist skeletal fractures. Mechanical properties of bone (reviewed in Bikle D D, Halloran B P, Journal of Bone & Mineral Metabolism. 17:233-44 (1999), micro-cracks (Hirano T. et al., Bone. 27(1):13-20, 2000.), endocrine regulators (reviewed in Seeman E. Delmas P D., Trends in Endocrinology & Metabolism. 12(7):281-3, 2001) and remodeling events are all likely factors involved in controlling the amount of bone at any particular skeletal site. TRAP appears to participate in the spatial orientation of where bone is formed during skeletal remodeling.

The experiments reported herein were performed with two sources of TRAP. One was from a purified protein extraction. This molecule would presumably be modified by post translational reactions. The second source of TRAP was material created as a GST fusion protein. Both sources of TRAP behaved similarly in the binding and activity assays. This finding argues that it is likely to be a specific amino acid sequence in the TRAP molecule that binds to TRIP-1 rather than a post-translationally added carbohydrate moiety.

A recombinant GST-TRAP fusion protein was made and shown to function like glycosylated TRAP. This recombinant protein is a non-glycosyl protein because prokaryotic cells don't have this post translation modification system. The purified TRAP proteins from mammalian source usually are highly glycosylated. Most of the polysaccharide moiety is mannose, mannose-6-phosphate and sialic acid.

TRAP is the molecule to induce ROS 17/2.8 and D14 osteoblast cells apoptosis but not from impurities, and the post-translation modification of TRAP is not required for the apoptosis effect.

d) TRIP

TRIP-1 has been characterized as a modulator of the TGFβ response (Choy, L. and Derynck, R., J. Biol. Chem. 273: 31455-31462 (1998)). It is a WD40 repeat-containing protein that is a phosphorylation substrate for the type II TGFβ receptor. TRIP-1, when phosphorylated, represses TGFβ-driven reporter activity from the plasminogen activator inhibitor-1 (PAI-1) promoter but has no effect on the TGFβ-driven cyclin A promoter (Choy, L. and Derynck, R., J. Biol. Chem. 273: 31455-31462 (1998)). The disclosed data indicate that when TRAP associates with TRIP-1, there is an activation of TGFβ signaling, which is consistent with the TRAP/TRIP-1 association blocking phosphorylation and allowing a full expression of the TGFβ signaling pathway. TRIP-1 homologs have also been identified in plants. Their function in these systems is not known, however, speculation that they may be involved in cell cycle activity is supported by their similarity to a translation initiation factor (Jiang, J. and Clouse, S. D., The Plant Journal 26:, 35-45 (2001)).

Mice deficient in osteoclast TRAP demonstrate skeletal abnormalities (Hayman A R. et al., Development. 122(10): 3151-62, (1996)). As expected, TRAP-null mice have a compromised ability to resorb bone through defective osteoclast activity. This is manifested as a mild osteopetrosis, i.e. skeletal density is slightly increased. However, a closer examination of the bone reveals a haphazard and disorganized micro-architecture. Additional evidence that removal of TRAP and other site-directing signals leads to inappropriate bone formation has been found at sites of inflammation and infection in bone, such as in periodontal disease (33). Bacterial and inflammatory cell activity at alveolar bone sites could very well destroy site-directing signals and prevent normal osteoblast function.

TRIP-1 has been cloned and characterized. TRIP-I is a negative regulator in the TGF-β signaling pathway. Disclosed herein TRIP-I function was tested in the chick sternal chondrocyte and osteoblast. TRIP-1 has the opposite effect for the TGF-β signaling pathway between these two cells. In check sternal chondrocyte, TRIP-1 is a negative TGF-β signaling regulator. It can diminish almost 60% of TGF-β effect with P3TP-luc as a reporter. However, in the osteoblast cell lines (SaOS2 and MG63), TRIP-I can potentate around two folds the TGF-β signaling pathway. TRAP protein can turn on the TGF-β signaling pathway by interacting with TRIP-1.

TRIP-1 protein has several WD40 domains in its C-terminal region (Choy L, Derynck R: *J Biol Chem* 273:31455-62, 1998), Chen R H, et al., *Nature* 377:548-52, (1995)). This WD 40 domain has been show to interact with Ras and then turn on the downstream signaling. Plasmid constructs of TRIP-1 having varied and deleted WD40 regions exist and can be used herein (Chen R H, et al., *Nature* 377:548-52, (1995)). Thus, the data indicate that TRIP-1 turns on Ras or MEKK pathway through interaction with the WD40 region, and this interaction affects the apoptotic signaling through the ras/raf pathway.

6. Delivery of the Compositions to Cells

Both nucleic acid and non-nucleic acid compositions can be delivered to cells either in vitro or in vivo. If a nucleic acid specific delivery system, is not used, then typically the delivery must at least be in a pharmaceutically acceptable carrier, which are discussed herein.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as SEQ ID NO:23 or SEQ ID NO: 37 (exogenous gene) into the cell without degradation and include a promoter yielding expression of the exogenous gene in the cells into which it is delivered. In some embodiments the delivery molecules are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families, which share the properties of these viruses, which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector, which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or trophisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules, which are needed in cis, for the replication, and packaging of the replicated virus. Typically a retroviral genome, contains the gag, pol, and env genes which are involved in the making of the protein coat. It is the gag, pol, and env genes, which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291(1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules, which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson,. Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. Those of skill in the art understand how to use these deliver systems both for nucleic acid and for non-nucleic acid compositions. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed peptides or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.)* 4:3-9, (1993); Battelli, et al., *Cancer Immunol. Immunother.*, 35:421-425, (1992); Pietersz and McKenzie, *Inmunolog. Reviews*, 129:57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subjects cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

d) Bone Specific Delivery Systems

It is preferred that the disclosed compositions are either specifically delivered to bone cells, such as osteoblasts or osteoblasts or that the delivered compositions are specifically expressed or activated in bone cells, such as osteoblasts.

Specific delivery can occur, by for example, isolation of the target cell, such as an osteoblast, with delivery of the composition to the isolated osteoblast.

7. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Tiers et al., Nature) 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers f unction to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovimus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puramycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410--413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

c) Bone Specific Expression Systems

It is preferred that the disclosed compositions are either specifically delivered to bone cells, such as osteoblasts or osteoblasts or that the delivered compositions are specifically expressed or activated in bone cells, such as osteoblasts.

Specific expression can occur in bone cells, by using a bone specific promoter such as type I collagen, alkaline phosphatase, osteonectin, osteocalcin, and the cbfa1 promoter.

8. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Other compositions which do not have a specific pharmaceutical function, but which may be used for tracking changes within cellular chromosomes or for the delivery of diagnositc tools for example can be delivered in ways similar to those described for the pharmaceutical products.

The compositions can also be used for example as tools to isolate and test new drug candidates for a variety of diseases. They can also be used for the continued isolation and study, osteoblast/osteoclast lacuna interactions and functions. There use as exogenous DNA delivery devices can be expanded for nearly any reason desired by those of skill in the art.

9. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

10. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understands what computer readable mediums. Thus, computer readable mediums on which the nucleic acids or protein sequences are recorded, stored, or saved.

Disclosed are computer readable mediums comprising the sequences and information regarding the sequences set forth herein. Also disclosed are computer readable mediums comprising the sequences and information regarding the sequences set forth herein wherein the sequences do not include SEQ ID Nos: 37, 38, 39, 40, 41, and 42.

11. Compositions Identified by Screening With Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. The nucleic acids, peptides, and related molecules disclosed herein can be used as targets in any molecular modeling program or approach. Also disclosed are the compositions that are identified through combinatorial techniques or screening techniques in which the compositions disclosed in SEQ ID NOS:1-50, for example, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation of the target molecule's function. The molecules identified and isolated when using the disclosed compositions, such as, GPC4 or TRAP or TRIP or SEQ ID NO:5 or SEQ ID NO23, are also disclosed. Thus, the products produced using the combinatorial or screening approaches that involve the disclosed compositions are also considered herein disclosed.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puramycin molecule is covalently attached to the 3'-end of the RNA molecule. An in vitro translation of this modified RNA molecule causes the correct protein, encoded by the RNA to be translated. In addition, because of the attachment of the puramycin, a peptidyl acceptor which cannot be extended, the growing peptide chain is attached to the puramycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puramycin at the 3'-end, new peptide is translated and another functional round of selection is performed. Thus, protein selection can be performed in an iterative manner just like nucleic acid selection techniques. The peptide which is translated is controlled by the sequence of the RNA attached to the puramycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostalck J. W. Proc. Natl. Acad. Sci. USA, 94(23)12997-302 (1997)).

Another preferred method for combinatorial methods designed to isolate peptides is described in Cohen et al. (Cohen B. A., et al., Proc. Natl. Acad. Sci. USA 95(24): 14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example an extracellular portion of GPC4 is attached to a DNA binding domain of a transcriptional activation protein, such as Gal 4. By performing the Two-hybrid technique on this type of system, molecules that bind the extracellular portion of GPC4 can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polypeptides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

Screening peptides similar to the peptide set forth in SEQ ID NO:23 for binding to TRAP or osteoclast lacuna, for example, is a method of isolating desired compounds.

Molecules isolated which bind TRAP can either be competitive inhibitors or non-competitive inhibitors or osteoblast or GPC4 or TRIP interactions. In certain embodiments the inhibitors of osteoblast binding to osteoclast lacuna are non-competitive inhibitors and in other embodiments the compositions can be competitive inhibitors. One type of non-competitive inhibitor will cause allosteric rearrangements which prevent osteoblasts from binding to osteoclast lacuna.

As used herein combinatorial methods and libraries included traditional screening methods and libraries as well as methods and libraries used in interative processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, SEQ ID NOs: 1-50, are also disclosed. Thus, the products produced using the molecular modeling approaches that involve the disclosed compositions, such as, SEQ ID NOs: 1-50 are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

12. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for acquiring osteoporosis, comprising the probes or primers related to sequences set forth in SEQ ID Nos:38 (GPC4), 40(TRIP), and 42(TRAP).

13. Functional Equivalents

It is understood that the compositions disclosed herein have certain functions, such as binding TRAP or binding TRIP or GPC4 or osteoblast cells, osteoclast cells, or osteoclast lacuna. Disclosed herein are certain structural requirements for performing the disclosed functions, and it is understood that there are a variety of structures which can perform the same function which are related to the disclosed structures, and that these structures will ultimately achieve the same result, for example stimulation or inhibition of osteoblast binding to osteoclast lacuna.

D. Methods

1. Methods of Making the Compositions

The compositions disclosed herein and the compositions necessary to perform the disclosed methods can be made using any method known to those of skill in the art for that particular reagent or compound unless otherwise specifically noted. Methods for protein synthesis or production a) Nucleic Acid Synthesis For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.,* 65:610-620 (1980), (phosphotriester method). Protein nucleic acid molecules can be made using known methods such as those described by Nielsen et al., *Bioconjug. Chem.* 5:3-7 (1994).

Nucleic acids can also be produced and replicated and manufactured using any known recombinant molecular biology protocol. These methods can be found for example in Sambrook et al., Molecular Cloning: A Laboratory Manual, 3rd Ed., Cold Spring Harbor Laboratory, Cold Spring Harbor, N.Y., 2001 which is herein incorporated by reference specifically at least for material related to the manipulation, such as production, of biological macromolecules such as nucleic acids and proteins.

b) Peptide Synthesis

One method of producing the disclosed proteins, such as SEQ ID NO:23, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

c) Processes for Making the Compositions

Disclosed are processes for making the compositions as well as making the intermediates leading to the compositions. For example, disclosed are nucleic acids in SEQ ID NOs:1-19, 37, 39, 41. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO: 39, or SEQ ID NO:41 and a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO: 39, or SEQ ID NO:41, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, SEQ ID NO: 39, or SEQ ID NO:41 and a sequence controlling the expression of the nucleic acid.

Disclosed are nucleic acid molecules produced by the process comprising linking in an operative way a nucleic acid molecule comprising a sequence encoding a peptide set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:38, SEQ ID NO: 40, or SEQ ID NO:42 and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID NO:19, SEQ ED NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:38, SEQ ID NO: 40, or SEQ ID NO:42 and a sequence controlling an expression of the nucleic acid molecule.

Disclosed are nucleic acids produced by the process comprising linking in an operative way a nucleic acid molecule comprising a sequence encoding a peptide having 80% identity to apeptide set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:18, SEQ ID NO:38, SEQ ID NO: 40, or SEQ ID NO:42, wherein any change from the SEQ ID Nos:19-36, SEQ ID NO:37, SEQ ID NO: 39, and SEQ ID NO:41 are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

2. Methods of Using the Compositions

Disclosed are methods of regulating bone formation which comprise administering to a patient in need of such regulation a peptide comprising an amino acid sequence set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:38, or SEQ ID NO:40 for a time and under conditions sufficient to regulate bone formation.

Also disclosed are methods of regulating bone formation which comprise administering to a patient in need of such regulation a peptide comprising an amino acid sequence having at least 80% identity to the peptides set forth in SEQ ID NO:19, SEQ ID NO:20, SEQ ID NO:21, SEQ ID NO:22, SEQ ED NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:38, or SEQ ID NO:40 for a time and under conditions sufficient to regulate bone formation.

Disclosed are methods, wherein the peptide is administered by systemic means or wherein the systemic means is intravenous or intra-arterial infusion or wherein the peptide is administered by implanting on bone.

Disclosed are methods of stimulating bone formation in a bone cell culture which comprise adding a peptide having an amino acid sequence set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:38, or SEQ ID NO:40 to a bone cell culture.

Disclosed are methods, wherein the bone cell culture comprises osteoblast cells or wherein the bone cell culture comprises osteoclast cells.

Disclosed are methods of regulating bone formation which comprise administering to a patient in need of such regulation a nucleotide molecule comprising a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, or SEQ ID NO:39 or the peptide produced from these nucleic acid molecules for a time and under conditions sufficient to regulate bone formation.

Disclosed are methods of regulating bone formation which comprise administering to a patient in need of such regulation a nucleotide molecule comprising a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, or SEQ ID NO:39 for a time and under conditions sufficient to regulate bone formation.

Disclosed are methods, wherein the nucleotide molecule transfects a bone cell or wherein the bone cell is an osteoblast cell. Methods to deliver specific proteins would include viruses that would infect all cells in the area and produce the protein of interest. Constructs that would be bone specific can be utilized, as well as ex vivo transfection in the laboratory and return of the patients cells to the site of interest, i.e. a fracture site or implant site. Also, manipulation of embryonic stem cells to produce the protein of interest and then differentiate it into osteoblasts can be performed.

Disclosed are methods of regulating bone formation which comprise administering to a patient in need of such regulation a cell which has been transformed with a nucleotide molecule having a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:37, or SEQ ID NO:39 for a time and under conditions sufficient to regulate bone formation.

Disclosed are methods, wherein the cell is a fibroblast cell, a cartilage cell, a bone marrow cell, a stem cell, or an adipocyte cell or wherein the nucleotide sequence is under the control of a promoter which functions in the cells.

Disclosed are methods of stimulating bone formation in a bone cell culture which comprise adding any one of the cells disclosed herein to the bone cell culture.

Disclosed are methods of promoting bone growth comprising contacting an area where bone growth is desired with a composition comprising tartrate resistant acid phosphatase Also disclosed are methods, wherein the composition further comprises an implant or methods wherein the implant is a dental implant.

Disclosed are methods of regulating bone growth comprising regulating the expression of GPC4 or TRIP in osteoblast cells.

Disclosed are methods, wherein the expression of GPC4 or TRIP is increased or methods wherein the expression of GPC4 or TRIP is decreased or methods wherein the expression of GPC4 or TRIP is regulated by an antisense molecule hybridizing to the mRNA of GPC4 or TRIP.

Disclosed are methods of producing an animal comprising introducing into the animal a cell containing a nucleic acid molecule set forth in SEQ ID NOS:1-18, 37, 39, 41, or any variants herein disclosed, such that the nucleic acid will be expressed in the animal.

Creation of a transgenic animal that would produce large amounts of a specific protein under the control of switchable promoter is disclosed. This has been done with the "tet" promoter. Genetic constructs placed down stream of a tetracycline inducible promoter can be "turned on" in an animal at any time by administering tetracycline. Knock-out of a given protein can be achieved by replacing the natural gene with a gene that has the initiation site ablated. No functional protein is then synthesized. Disclosed are the knockins and knockouts of the disclosed nucleic acids disclosed herein, including SEQ ID NOS:1-18, 37, 39, and 41. Also disclosed are animals that are expressing the nucleic acids or peptides disclosed herein.

Over-expression of either GFC4 or TRIP in osteoblasts (or other cell types) would allow control of the site and amount of bone formation. Delivery of these agents by gene therapeutic techniques or pharmacologic agents that upregulate GPC4 and TRIP would be two ways to induce cell to produce the molecules. Moreover, identification of the substrates that bind to GPC4 and TRIP can provide a synthetic stimulatory environment for the formation of new bone. This could be used around orthopaedic and dental implants to more securely anchor the prostheses in bone.

Another use for these molecules may be as a diagnostic tool. Assays for the level of either or both of GPC4 and TRIP can be used to predict metabolic bone diseases such as osteoporosis and/or osteopetrosis.

a) Methods of Using the Compositions as Research and Diagnostic Tools

The disclosed compositions can be used in a variety of ways as research tools. For example, the disclosed compositions, such as SEQ ID NOs:19-36 can be used to study the interactions between osteoblasts and osteoclast lacuna, by for example acting as inhibitors of binding.

The compositions can be used for example as targets in combinatorial chemistry protocols or other screening protocols to isolate molecules that possess desired functional properties related to osteoblasts and osteoclasts.

The disclosed compositions can also be used diagnostic tools related to diseases of the bone, such as osteoporosis or other bone maladies. A partial list of bone maladies is shown in Table 3.

TABLE 3

| | |
|---|---|
| type I postmenopausal osteoporosis | sarcoidosis |
| type II age-related osteoporosis | diabetes |
| male osteoporosis | osteomalacia |
| secondary osteoporosis due to steroid or pharmaceutical use | VDRR, VDDR, and nutritional rickets hypervitaminosis A and D |
| renal osteodystrophy | Paget's Disease |
| renal stones | osteopetrosis |
| juvenile idiopathic osteoporosis | skeletal tumors |
| hyperparathyroidism | rheumatoid and osteo arthritis |
| hyperthyroidism | osteogensis imperfecta |
| hypercalcemia's | chondrodystrophies |
| Fanconi syndrome | sclerosing bone dysplasias |

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any method for determining allelic analysis of for example, GPC4, TRIP, or TRAP, particularly allelic analysis as it relates to osteoblast and osteoclast lacuna interactions and functions. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

b) Pharmaceutical Methods

The disclosed compositions can in certain embodiments be delivered as pharmaceutical reagents, based on their ability to inhibit binding of osteoblasts to osteoclasts. Many bone disease states are related to inappropriate osteoblast/osteoclast interactions. For example, compositions that bind TRAP and inhibit osteoblast binding to osteoclast lacuna can be used for example to modulate processes such as heterotopic bone formation, osteophyte formation, diffuse idiopathic skeletal hyperostosis (DISH), and myositis ossificans progressiva (MOP), etc.

E. EXAMPLES

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Phage Display and Isolation of Molecules That Bind TRAP a) Osteoblasts Bind and Differentiate in Resorption Lacunae Resorption lacunae formed on the surface of cortical bone wafers (by a modification of the methods published by Dempster and Chambers, 33-35) were used as substrate surfaces on which to study osteoblast behavior. By all criteria, these lacunae represent the result of authentic osteoclast activity. Moreover, they resemble in vivo lacunae by virtue of their surface characteristics (SEM) and lysosomal content (immunocytochemistry). For example, it was shown that: i) that there is a high concentration of mannosylated carbohydrate side chains on resident lysosomal enzymes in lacunae, ii) that TRAP is prevalent along resorbed surfaces and iii) that osteoblasts can adhere within the lacunae. (Data showed FITC conjugated lectin (Pisum sativum) with specificity for mannose carbohydrate structures binds only within osteoclast lacunae (dotted lines) on cortical bone wafers. Data also showed that FITC conjugated lectin (concanavalin A) with specificity for mannose and glucose structures binds only within osteoclast lacunae (dotted lines) on cortical bone wafers. In addition data showed cross sections of an osteoclast pit in a cortical bone wafer demonstrated that the presence of TRAP in the pit area by immunocytochemistry and data also showed an osteoblast binding within a resorption lacunae on a cortical bone wafer.)

Bone wafers have been used to demonstrate that osteoblasts bind with much higher affinity to resorption surfaces than unresorbed surfaces and that when they bind they alter their phenotype toward a more differentiated state.

Figure 3:
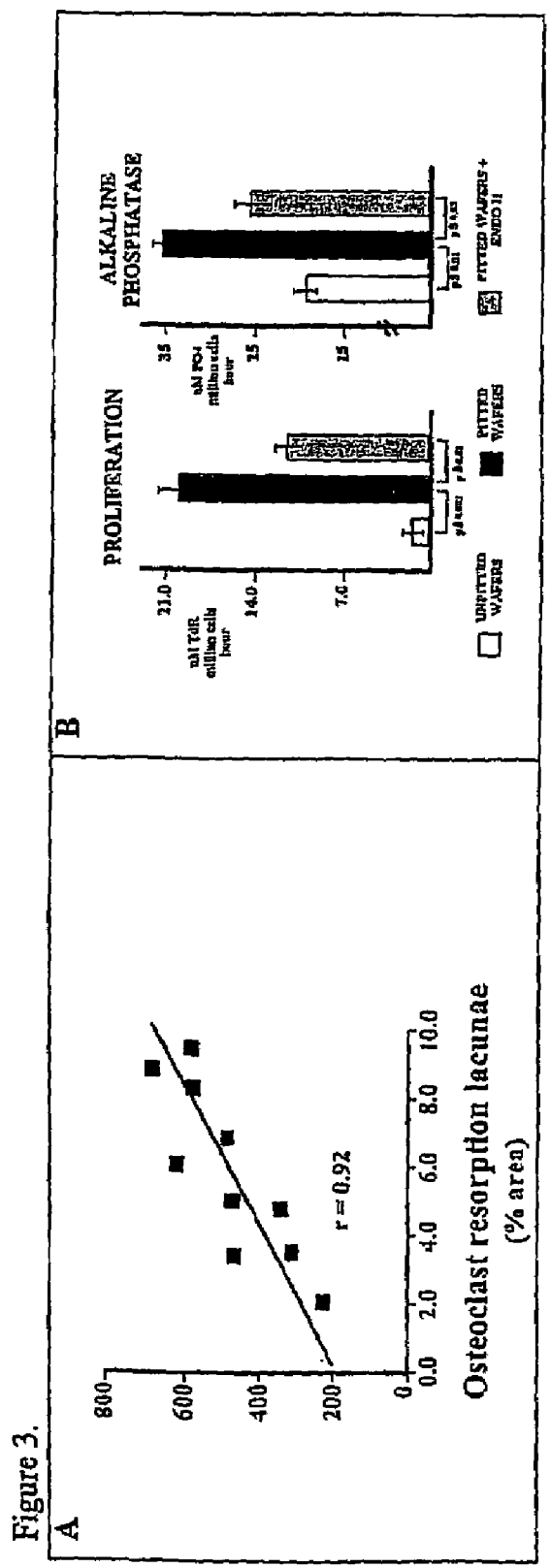

FIG. 3a shows that there is a positive correlation between the extent of osteoclast pitting on a wafer and the affinity of the osteoblasts to bind. FIG. 3b demonstrates that osteoblasts residing on pitted wafers produce more alkaline phosphatase per cell and proliferate at a greater rate. Data also showed a visual demonstration of alkaline phosphatase activity only in osteoblasts residing in resorption pits. Data showed that osteoblast cultured on pitted bone wafers, and that only cells visibly producing alkaline phosphatase (staining) reside within osteoclast lacunae. In control experiments the wafers have been treated with glycosidases and boiling and have been able to eliminate the binding and differentiation effects. Thus, these data document that osteoblasts can use specific site-directing signals for attachment and differentiation and that the signals can be removed with enzymatic treatments and boiling.

Exposing osteoblasts in culture directly to soluble lysosomal enzymes validated these results. These data have been published and document that soluble TRAP has many of the differentiation and proliferation characteristics of TRAP bound to resorption surfaces. A compilation of these data is presented in FIG. 4.

These results show that 1) Osteoblasts bind and differentiate in resorption lacunae, 2) Removal of soluble factors from the lacunae eliminates the effect, and 3) Soluble TRAP can mimic some of the differentiative and proliferative effects of osteoblasts binding to lacunae.

b) Phage Display

Figure 2:
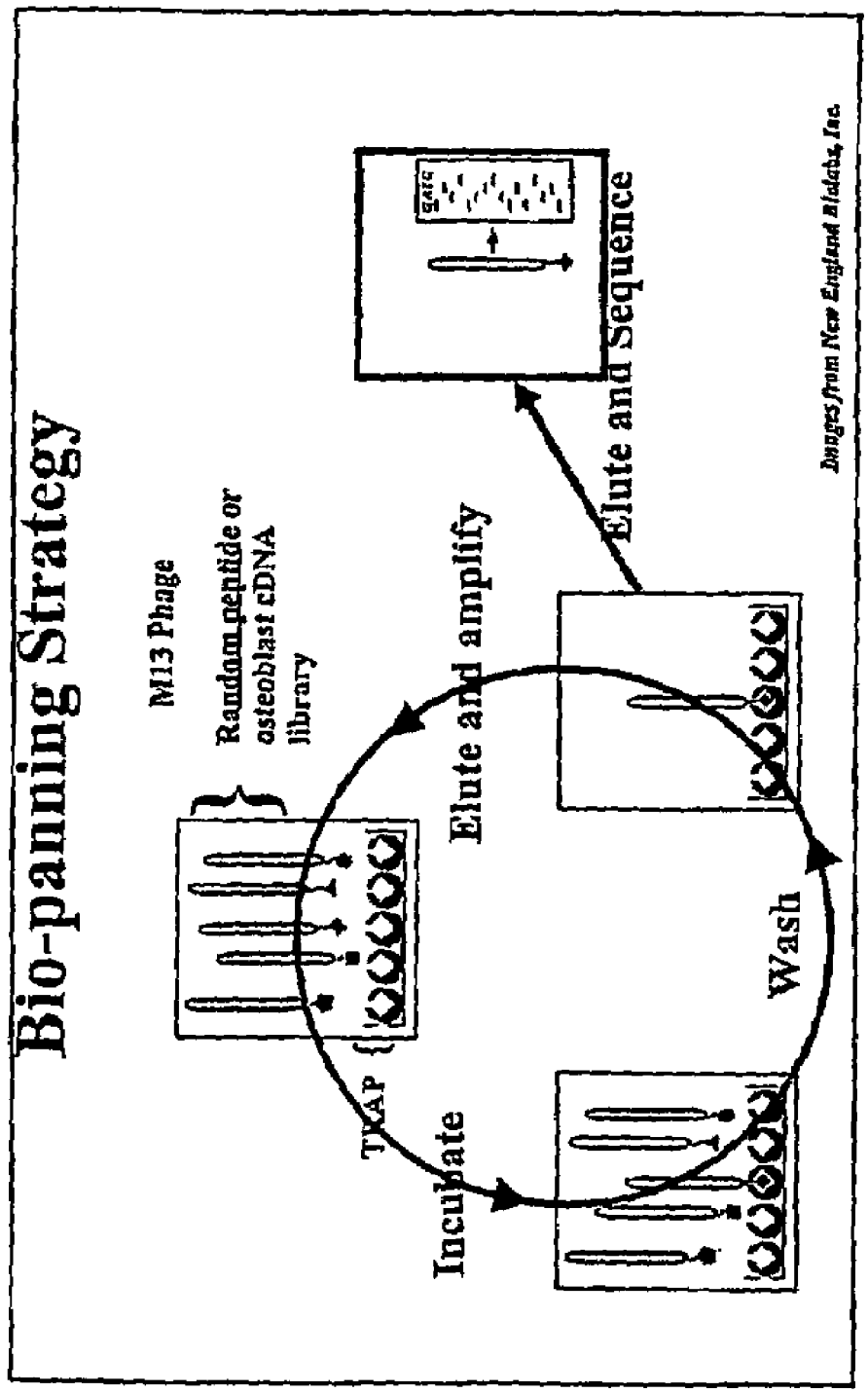

In phage display either random peptide libraries or cell specific cDNA libraries can be used. Both have been used to target the interactions that take place in bone resporbtion and formation. Generally, the peptides or proteins are expressed on the surface coat of M13 or T7 phage and then these phage are used in a biopanning technique to identify which phage have affinity for a particular substrate (the "bait"). The adherent phage are eluted, amplified and used in another round of panning. After at least three rounds, phage clones are sequenced. This process is diagrammatically shown in FIG. 2.

(1) Random Phage Library

The type V tartrate resistant acid phosphatase (TRAP) was used as bait with a random peptide phage display library. TRAP was selected because of its association with osteoclast bone resorptive activity and because it has been demonstrated that it remains bound to lacunae (Chambers T J. et al., ournal of Cellular Physiology. 132(1):90-6, 1987 July 87250990; Murrills R J. et al., Endocrinology. 127(6): 2648-53, 1990; Wergedal J E. Baylink D J., Journal of Histochemnistry & Cytochemistry. 17(12):799-806, 1969; Murrills R J. et al., Journal of Bone & Mineral Research. 4(2):259-68, 1989). The TRAP used in these experiments was purified to homogeneity and was generously provided by Dr. M. Roberts.

A random 12 amino acid oligopeptide expression library in M13 phage was used to probe TRAP that was immobilized on a tissue culture dish. After three rounds of biopanning, elution and amplification 44 phage clones were selected at random and sequenced. Nine different sequences were identified. They are listed in Table 4 along with their consensus frequency. The most frequent phage sequenced was represented 15 times and the least frequent only a single time.

TABLE 4

Results of Phage Display Bio-Panning with TRAP

| SEQ, ID No. | Table 1: DNA and Peptide Sequence | Fre |
|---|---|---|
| SEQ. ID No. I | CACTCTACTATGGGTTTTACGGCTCCGCCGCATTAT | 1144 |
| SEQ. ID No. 19 | HSTMGFrAPPHY | |
| SEQ. ID No. 2 | ACTATGGGTTTTACGGCTCCGCGGTTTCCGCATTAT | 6/44 |

TABLE 4-continued
Results of Phage Display Bio-Panning with TRAP

| SEQ, ID No. | Table 1: DNA and Peptide Sequence | Fre |
|---|---|---|
| SEQ. ID No. 20 | TMGFrAPRFPHY | |
| SEQ. ID No. 3 | TCTCAGTGGCATCCGCGGTCTGCGTCGTATCCGATG | 4/44 |
| SEQ. ID No. 21 | SQWHPRSASYPM | |
| SEQ. ID No. 4 | ACGCCGTCTCTTCCTCCGACTATGTTTCGGTTGACT | 4/44 |
| SEQ. ID No. 22 | TPSLPPTMFRLT | |
| SEQ. ID No. 5 | ACGCCGCTTTCGTATCTGAAGGGTCTGGTGACGGTG | 15144 |
| SEQ. ID No. 23 | TPLSYLKGLVTV | |
| SEQ. ID No. 6 | CGGCCACGGAACACCAGTAGACGTCCCATGCGCAGA | 2/44 |
| SEQ. ID No. 24 | SAHGTSTGVPWP | |
| SEQ. ID No. 7 | ATAATGCGGAAACCGCGGAGCCGTAAAACCCATAGT | 5/44 |
| SEQ. ID No. 25 | TMGFrAPRFPHY | |
| SEQ. ID No. 8 | CGGCCAACGGAACACCAGTAGACGTCCCATGCGCAG | 2/44 |
| SEQ. ID No. 26 | LRMGRLLVFRWP | |
| SEQ. ID No. 9 | ACCAAGCCCCGAATCACGCGAATAAAGCGGCCAAGA | 2/44 |
| SEQ. ID No. 27 | SWPLYSRDSGLG | |
| SEQ. ID No. 10 | CAGAGCCTCCTTCGTCCAATTTCACACACTAAGCCC | n.d. |
| SEQ. ID No. 28 | GLSVEIGRRRL | |
| SEQ. ID No. 11 | CCGATCATACATAACCGAAATCAGATGAAACGGCAG | n.d. |
| SEQ. ID No. 29 | LPFHLISVMYDR | |
| SEQ. ID No. 12 | CATCTTGCGCCGATGCCTCGGGCGTTGCATACGGGT | n.d. |
| SEQ. ID No. 30 | HLAPMPRALHTG | |
| SEQ. ID No. 13 | GGGCTTAGTGTGTGAAATTGGACGAAGGAGGCTCTG | n.d. |
| SEQ. ID No. 31 | GLSV-NWTKEAL | |
| SEQ. ID No. 14 | CATCTTGCGCCGATGCCTCGGGCGTTGCATACGGGT | n.d. |
| SEQ. ID No. 32 | HLAPMPRALHTG | |
| SEQ. ID No. 15 | TTTGTGAAGCCTAAGGCGCTGTCTCTGCAGGCTGTG | n.d. |
| SEQ. ID No. 33 | FVKPKALSLQAV | |
| SEQ. ID No. 16 | TTTCATGTGAATCCGACGTCTCCGACGCATCCGTTG | n.d. |
| SEQ. ID No. 34 | FHVNPTSPTHPL | |
| SEQ. ID No. 17 | CAGCATGCGAATCATCAGGCTTGGAATAATCTTCGT | n.d. |
| SEQ. ID No. 35 | QHANHQAWNNLR | |
| SEQ. ID No. 18 | TTTCATGTGAATCCGACGTCTCCGACGCATCCGTTG | n.d. |
| SEQ. ID No. 36 | FHVNPTSPTHPL | |

The five most frequently occurring phage were then individually tested for their affinity to TRAP using a modified ELISA method. In this assay, immobilized TRAP was probed with complete phage that were then visualized with a secondary antibody to the phage coat. The binding was compared to wild type phage containing no expressed oligopeptides. These data are presented in FIG. 4. The five phage with the highest consensus frequency demonstrated at least a 40 fold increase in affinity for TRAP over wild type phage with Clone 5 phage showing a greater than 55 fold increase in affinity (although not statistically significantly different from the other phage). Clone 5 phage also possessed the highest consensus frequency.

Figure 6:
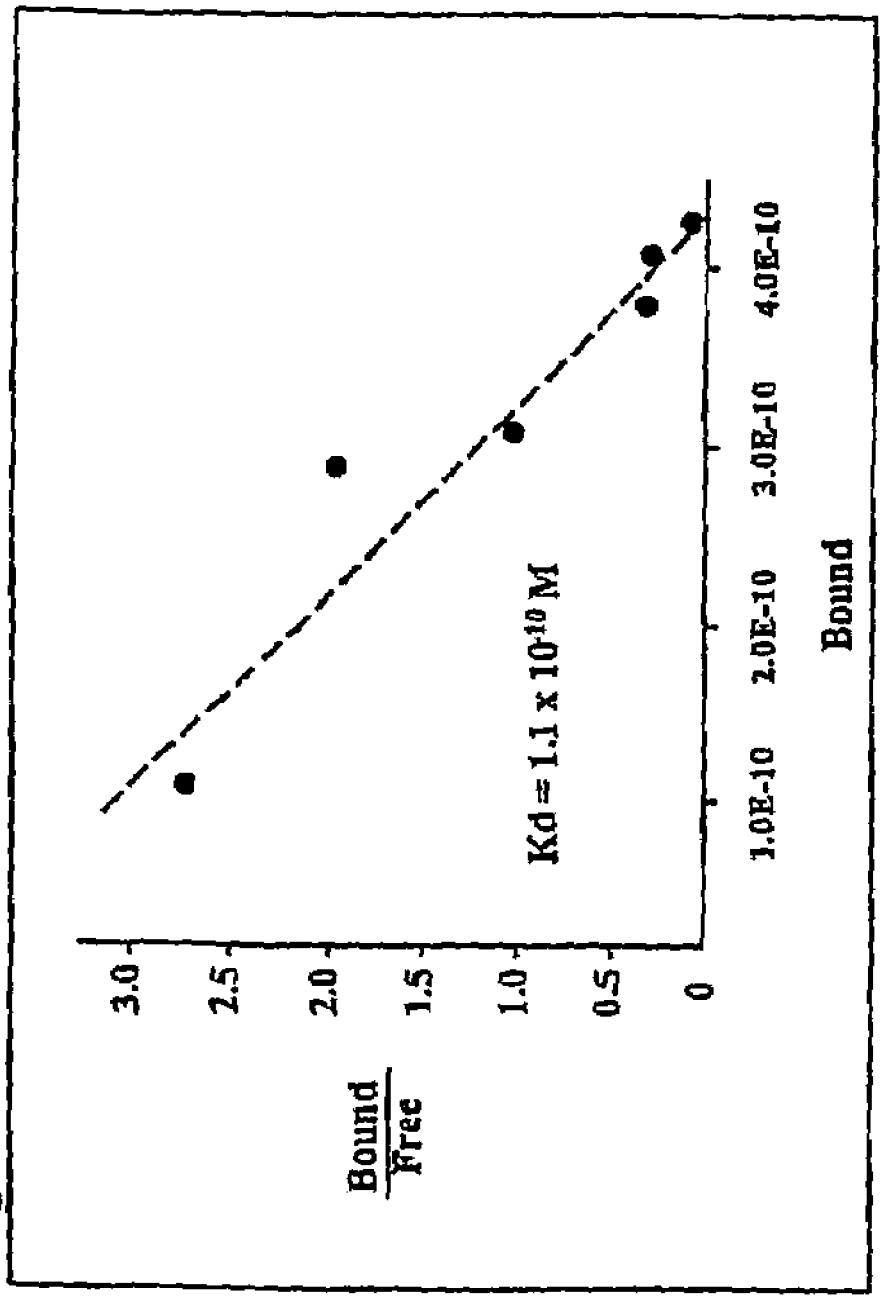

The actual affinity of Clone 5 phage for TRAP was determined in an a Scatchard-type experiment utilizing immobilized TRAP and increasing concentrations of phage particles. These data are presented in FIG. 6. They show that Clone 5 phage have an extremely high affinity for the TRAP substrate with a Kd of 1.1×10-10M.

Figure 7:
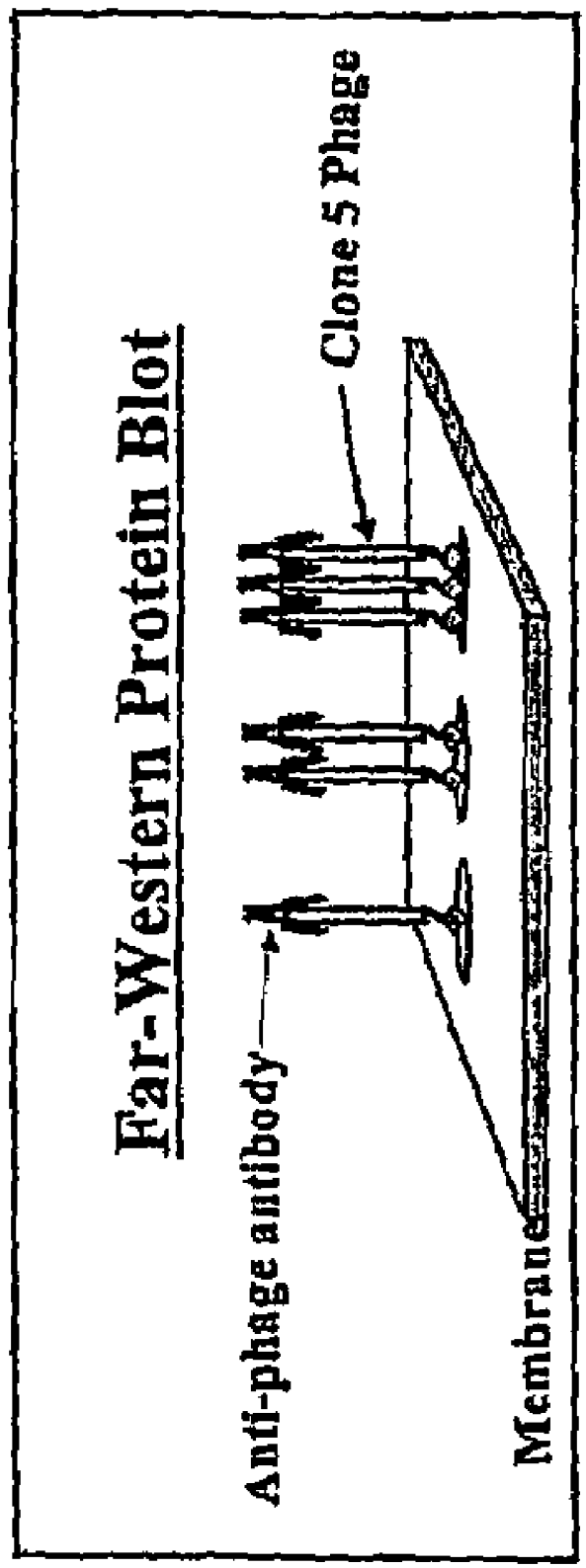

Confirmation that Clone 5 phage were actually binding to TRAP was obtained with Far-Western technology (FIG. 7). In these experiments, the target molecule, TRAP, as well as control proteins, bovine serum albumin (BSA) and RNase A, were separated with polyacrylamide gel electrophoresis, transferred to a membrane and then probed with intact Clone 5 phage. The only proteins in gels that were visualized appeared at the molecular weight for TRAP.

As TRAP is known to be present in resorption lacunae we sought to demonstrate that Clone 5 phage could recognize it on a resorbed bone surface. Osteoclast lacunae (i.e. pits) were prepared on cortical bone wafers as described herein. These pits are a hallmark of authentic osteoclast activity and are frequently used to quantify bone resorptive activity. Osteoclasts were removed by gently scraping and washing the surface of the bone wafers. The wafers were then probed with Clone 5 phage. Visualization of the phage was with a secondary antibody conjugated to HRP. Data showed that the localization of Clone 5 phage was in resorption lacunae. Data showed that Clone 5 phage only bound to the surfaces of resorption lacunae. These phage were visualized with a HRP-conjugated antibody directed against the phage (as in FIG. 7). Control experiments demonstrating no binding in unpitted wafers, with wild type phage and with the secondary antibody alone. Data showed that TRAP can be removed from the lacuna by boiling and that phage will no longer bind to these sites. Clone 5 phage localized only to prior resorbed osteoclast pits. There was no staining on adjacent surfaces. Moreover, there was no staining i) on un-pitted bone wafers, ii) with wild type phage, iii) when only the secondary antibody was used or iv) if the pitted bone wafers were boiled to extract all proteins not covalently associated with the resorption surface. The staining in the pits was punctate in nature.

Data demonstrated that TRAP in osteoclast lacunae can be extracted and visualized in a Far-Western with Clone 5 phage. In this experiment pitted and un-pitted wafers were extracted by boiling and the recovered proteins separated on polyacrylamide gels. Typically far-Western proteins were extracted from bone wafers. The only protein extracted from pitted bone wafers that could be visualized by Clone 5 phage was TRAP. No material from unpitted wafers was visualized by Clone 5 phage. In gels, a 37 kDa protein was present in the 5 microgram lane, and more was present in the 10 microgram lane, of pitted bone wafers. No band was visible in the 10 microgram lane of the unpitted bone wafers. A dose dependence for TRAP was also demonstrated as increasing its concentration led to more intense staining. No bands anywhere through the gel were visualized withS BSA or RNaseA. These data support the conclusion that Clone 5 phage were selected based on their affinity TRAP. After transfer to membranes protein bands were visualized as described in FIG. 7. The only protein visualized was at the molecular weight for TRAP. This analysis was dose dependent since adding more of the protein extract increased the intensity of staining. Proteins extracted from un-pitted wafers on which there was no osteoclast activity were negative for staining with Clone 5 phage. Not only does this experiment demonstrate the specificity of Clone 5 phage for TRAP, it also demonstrates the feasibility of extracting detectable bait proteins from lacunae. This indicates that proteins can be recognized in the lacunae.

Figure 8:
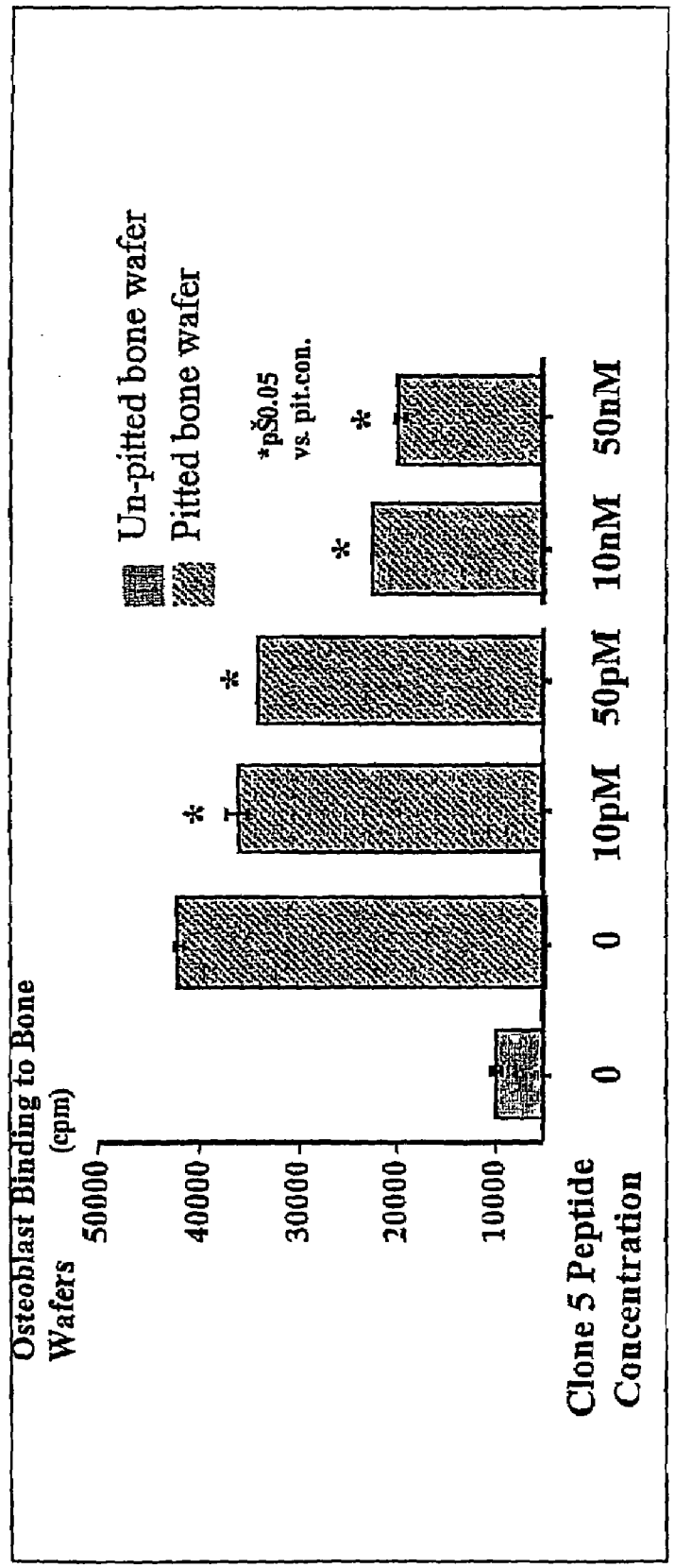

The 12 amino acid oligopeptide corresponding to the sequence from Clone 5 can inhibit osteoblast binding to osteoclast lacunae. FIG. 8 shows that a synthetic peptide with the same sequence as in Clone 5 phage can, in a dose dependent manner, block osteoblast binding to pitted bone wafers. In these data we demonstrate that osteoblasts bind at an approximately five fold higher level on bone wafers containing osteoclast pits as compared to un-pitted wafers. (For these experiments, approximately 20% of the area of the wafers was pitted.) A concentration of 50 nM for the oligopeptide blocked osteoblast binding by approximately 66%. A statistically significant inhibition for binding occurred down to a concentration of 10 pM of the oligopeptide. In data not shown, we found that control proteins did not compete with osteoblast binding.

A FASTA protein data base search was performed using sequence TPLSYLKGLVTV (SEQ ID NO:23) and identified four candidates with high homology to this sequence. They are listed in Table 5. It is unlikely that Rac1 (RAS-related C3 botulinum substrate) and Grin1 (glutamate receptor) would have relevance to osteoblasts, however, Wnt7a (wingless differentiation receptor) and Gpc4 (glypican 4) may. Wnt7A is known to play a key role in cell differentiation and has been associated with skeletal development but perhaps most importantly, Gpc4 is a member of a family of attachment receptors expressed on the surface of cells. It does not have a cytosolic domain and is believed to function solely in cell attachment (reviewed in David, G., FASEB J. 7:1023-1030, 1993.).

TABLE 5

FASTA Search for Clone 5 Homology

| Rac1 | Ras-related C3 botulinum substrate | T | P | I | T | Y | P | Q | G | L | A | M | A |
|---|---|---|---|---|---|---|---|---|---|---|---|---|---|
|  |  | : | : | . | . | : | . | . | : | : | . | . | . |
|  |  | T | P | L | S | Y | L | K | G | L | V | T | V |
| Grin1 | Glutamate receptor | T | P | V | S | Y | T | A | G | F | Y | R | I |
|  |  | : | : | . | : | : | . | . | : | . | . | . | . |
|  |  | T | P | L | S | Y | L | K | G | L | V | T | V |
| Wnt7a | Wingless-related MMTV integration protein | K | P | L | S | Y | R | K | P | M | D | T | D |
|  |  | . | : | : | : | : | . | : | . | . | . | : | . |
|  |  | T | P | L | S | Y | L | K | G | L | V | T | V |
| GPC4 | Glypican 4 | I | Y | C | S | H | C | R | G | L | V | T | V |
|  |  | . | . | . | : | . | . | . | : | : | : | : | : |
|  |  | T | P | L | S | Y | L | K | G | L | V | T | V |

":" indicates a perfect amino acid homology.
"." indicates an amino acid similarity Glypican 4 (Gpc4) is one member of a close family of heparan sulfate proteoglycan-containing plasma membrane receptors found on fibroblasts, periodontal ligament cells and mesenchymal and marrow stem cells (Worapamorm, W., et al., Connective Tiss. Res. 41: 57-68, 2000; Siebertz, B., et al., Biochemical. J. 344: Pt3: 937-43, 1999.). These receptors have been implicated in BMP signaling in Drosophila and as cytokine presenting receptors in bone marrow cells. Furthermore, mutations in the glypican family lead to a disease known as Simpson-Golabi-Behmel syndrome (Pilia, G., et al., Nature Genetics 12: 241-247, 1996). Mice with this syndrome demonstrate a varied phenotype, however, the one common feature in all forms is skeletal abnormalities.

All of the analysis done for the clone 5, discussed herein, can be performed on each and every molecule identified herein as having TRAP and/or osteoclast lacunae binding properties. Thus, the i) specificity for TRAP with Far Western technology (as in FIG. 7); ii) determination of a Kd for TRAP (as in FIG. 6); iii) examination of their localization within resorption lacunae(as in FIG. 9); iv) examination of the effect of a synthetic peptide for interfering with osteoblast binding and differentiation (as in FIG. 8); v) identification of any differentiation effects of these peptides; a FASTA search for their homology with proteins known to exist in nature; evaluation of positive homologous candidates will be evaluated in a manner similar to glypican 4 (see herein).

Figure 12:
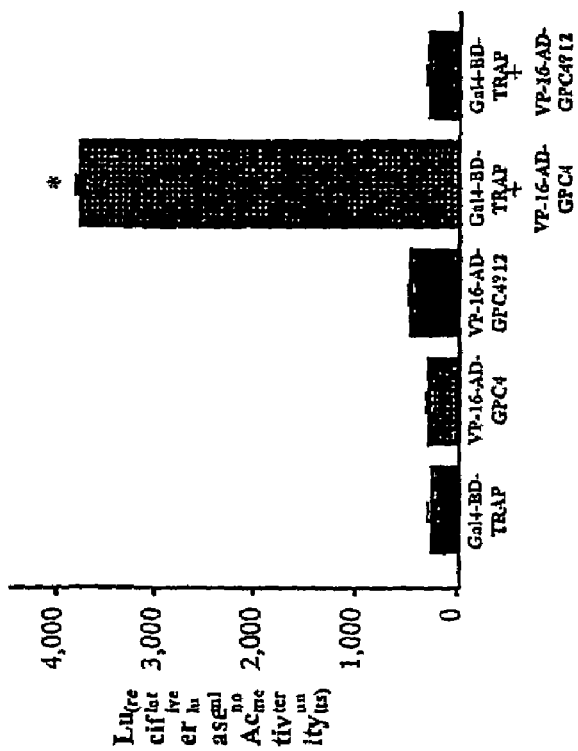

In order to demonstrate that GPC4 exists in osteoblasts and that its full length sequence also has affinity for TRAP, we performed a mammalian two-hybrid study with a human TRAP cDNA and GPC4 obtained from a human osteoblast-like library (MG-63 cells). Individual transfection of GAL-4-BD-TRAP, VP-16-AD-GPC4 or VP-16-AD-GPC412 into SaOS$_2$ cells did not activate luciferase activity. However, co-transfection of GAL-4-BD-TRAP and VP-16-AD-GPC4 into SaOS$_2$ cells demonstrated a 10-20 fold increase in luciferase activity. Co-transfection of GAL-4-BD-TRAP with a 12 amino acid deficient version of GPC4 (VP-16-AD-GPC412) also showed no difference from control levels (FIG. 12). These data demonstrate that a full length fusion protein for GPC4 can interact with a fusion protein for TRAP and that the interaction depends on the same 12 amino acids identified in the Clone 5 sequence. Moreover, these data also demonstrate that the osteoblast-like cell line, MG-63, contains transcripts for GPC4.

Figure 13:
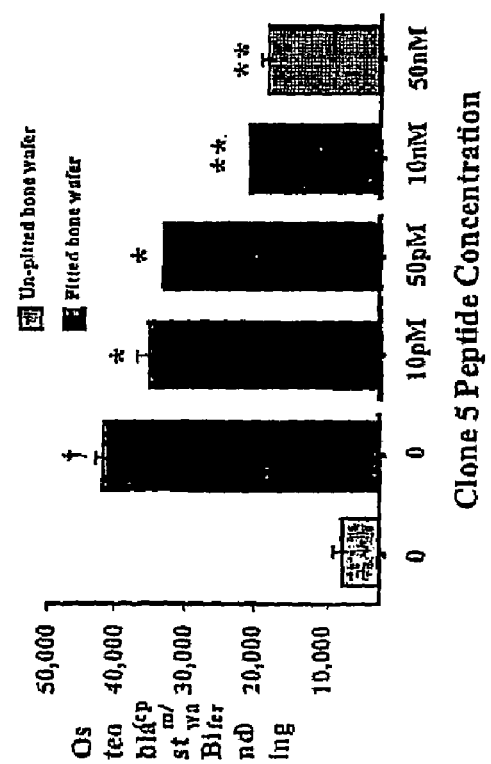

The 12 amino acid oligopeptide corresponding to the sequence from Clone 5 can inhibit osteoblast binding to osteoclast lacunae. FIG. 13 shows that a synthetic peptide with the same sequence as in Clone 5 phage can, in a dose dependent manner, block osteoblast binding to pitted bone wafers. In these data we demonstrate that osteoblasts bind at an approximately five fold higher level on bone wafers containing osteoclast pits as compared to un-pitted wafers. For these experiments, approximately 20% of the area of the wafers was pitted. A concentration of 50 nM for the oligopeptide blocked osteoblast binding by approximately 66%. A statistically significant inhibition for binding occurred down to a concentration of 10 pM of the oligopeptide. In data not shown, we found that control proteins did not compete with osteoblast binding.

c) Osteoblast cDNA Phage Display Library

A phage display library in M13 phage that expressed all the proteins produced by osteoblasts was made. The cDNA library was created from a rat calvarial preparation containing 99.5% osteoblasts as judged by alkaline phosphatase histochemistry and osteocalcin immunocytochemistry (see Detailed Methods of Procedure). M13 phage were selected because of their larger capacity for expression constructs.

After three rounds of bio-panning, elution and amplification using TRAP as the bait we sequenced 25 clones. Of the clones with the highest consensus sequence one of the sequences corresponded to TRIP, the TGFβ receptor interacting protein (Choy L. and Derynck, R., J. Biol. Chem. 273: 31455-31462 (1998); Griswold-Prenner, I., et al., Molec. Cell. Biology 18: 6595-6604 (1998)). The true function of this protein is unknown, however, from reports in the literature it appears that ligand binding to TRIP can either enhance or inhibit the effect of TGFβ.

In order to document that TRIP was, indeed, present in osteoblasts primers from the known human/rat homologous sequences were synthesized and osteoblast mRNA was PCR-probed. A prominent band representing the expected 1 kB of sequence was obtained (Data showed that no band was present in the control lane, a small band was present in the 1 ug RNA lane and a heavy band was present in the 5 ug RNA laneS).

Figure 9:
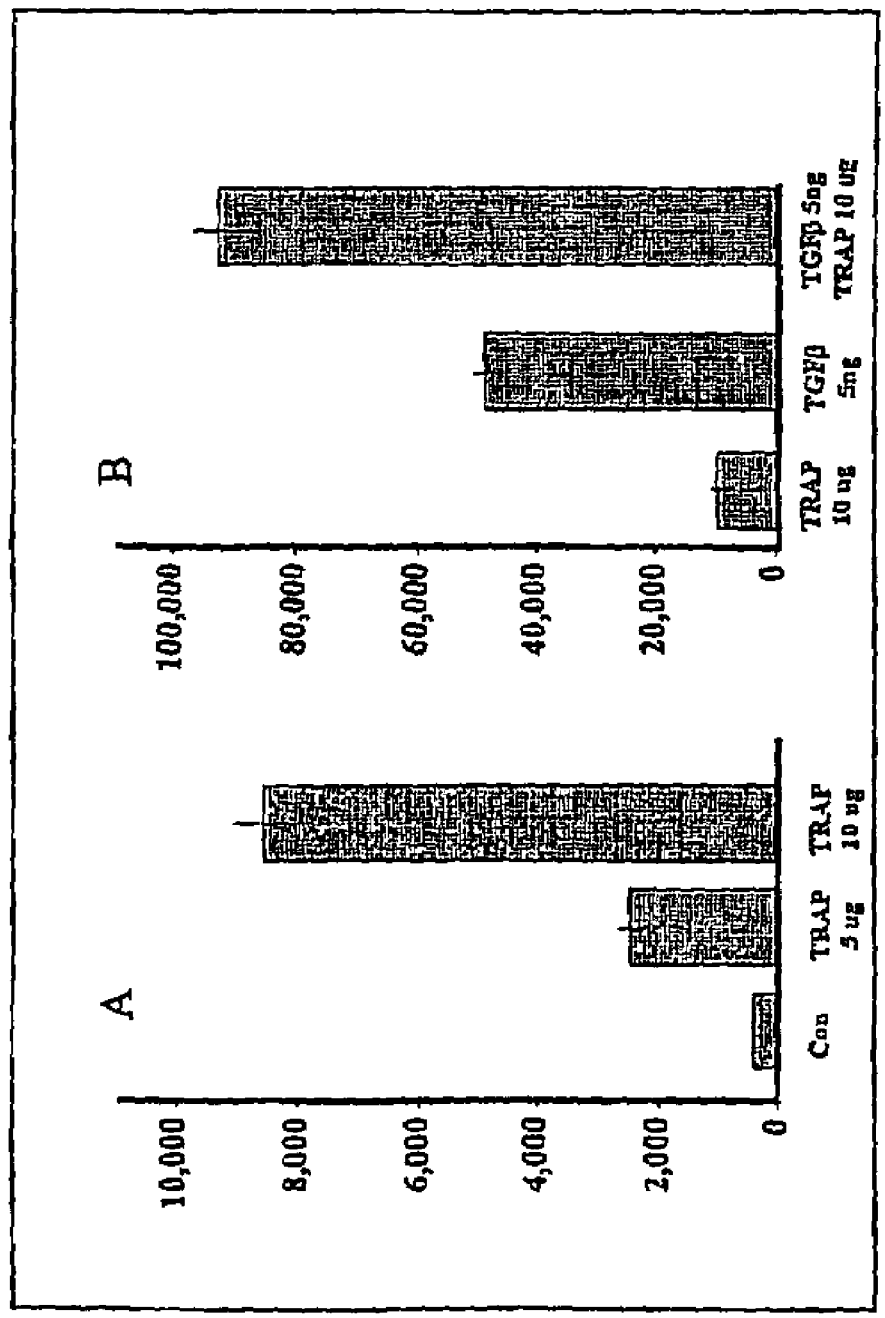

Functionality of TRIP for TGFβ signaling was determined by measuring the activation of a TGFβ promoter/reporter construct, P3TP Lux (see Experimental Design for a complete description of this construct). These data indicate that TRAP binding to osteoblasts (presumably through TRIP) activates P3TP Lux (FIG. 9).

Thus, 1) An osteoblast cDNA phage display library identifies TRIP as a protein with high affinity for TRAP, 2) TRIP is present in osteoblasts, and 3) TRAP activates TGFβ signaling pathways (presumably mediated by TRIP).

Figure 10:
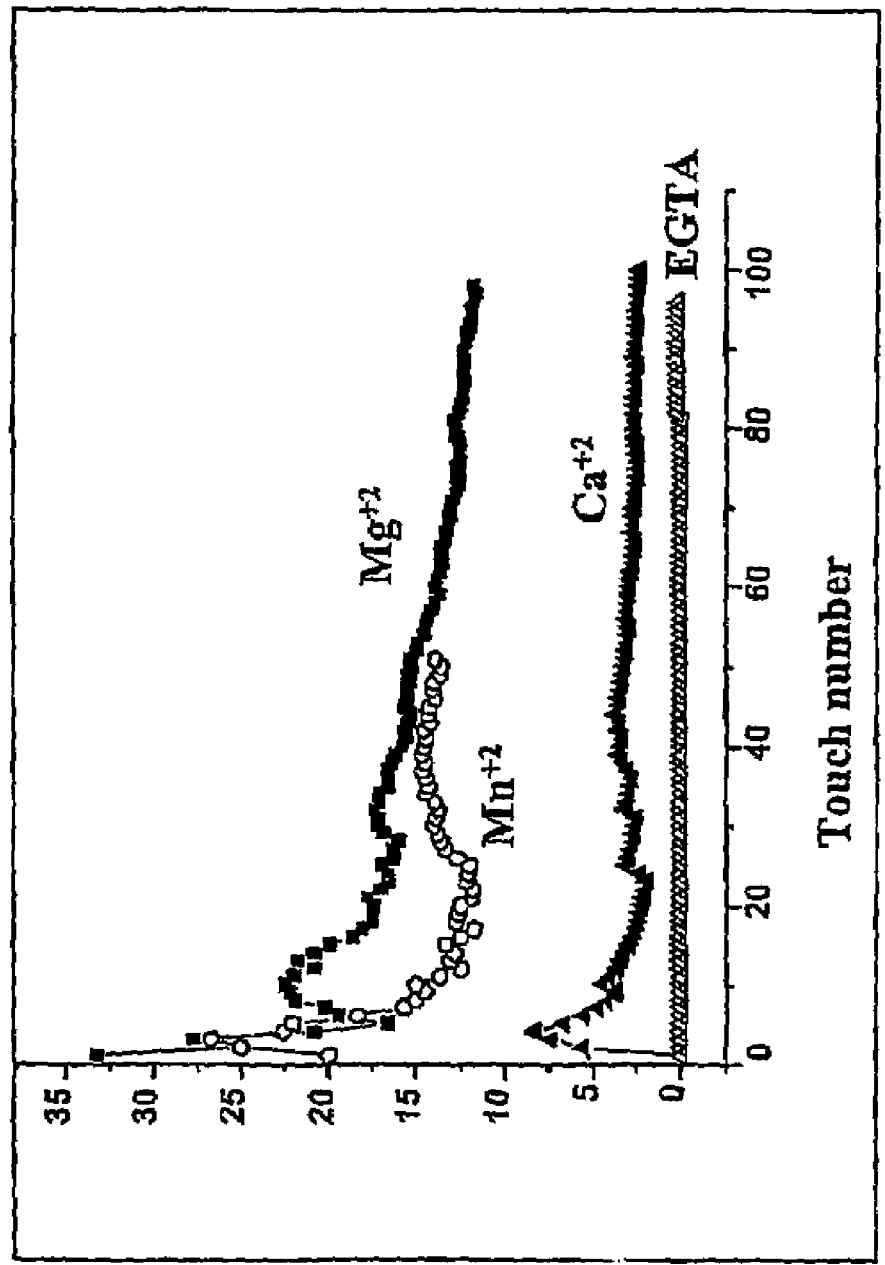

For our osteoblast binding and affinity assays single cell attachment has been measured. A single cell is captured by gentle suction on the end of a specially pulled glass pipette. It is then brought into contact with a surface (that can be either organic or inorganic in nature) or a monolayer of cells (Typically a PC-3 cell was brought into contact with a bone wafer (i.e. the dark material on the left of each frame) for 120 seconds. The cell was then pulled away from the wafer surface. The cells deformed during the pull-away, and the cell springing back toward the wafer after release of the suction in the pipette occurred. This series would represent "one" adhesive event. See FIG. 10 for quantitation of this effect.). Single cell-to-cell contact can also be performed by capturing two individual cells and bringing them into contact with each other. After defining two key variables that affect the adhesion, namely the length of time of contact and the contact pressure (i.e. impingement force), the occurrence of an adhesive event can be determined by pulling the cell away from the surface. An adhesive event occurs when, under phase contrast microscopy, it is evident that the plasma membrane of the cell is deformed by its adhesion. For the purposes of this assay the action of bringing a cell into contact with a surface for a specific time and at a specific pressure as a "touch". The adhesion characteristics of a cell for a surface was then determined by relating the number of "touches" to the number of adhesive events. (FIG. 10). The effect of different divalent cations on neutrophil attachment wasb measured. Both Mg+2 and Mn+2 created a conformational change in the integrin receptor profile. Activation of these receptors leads to increased affinity. Ca+2 had a minor effect on altering integrin conformation and the absence of divalent cations (EGTA) prevents any neutrophil binding.

A second measure of cell affinity for a surface or a cell layer can be determined by measuring the force needed to remove the cell from the substrate. This is done by constructing a pipette that matches the approximate diameter of the cell and manometrically measuring the force necessary to pull the cell away. Forces for this type of interaction are in the pico Newton range and can be determined Methods such as these have been exploited by scientists for a number of years in the study of hematopoietic cell-cell interactions, cell-capillary wall interactions, cell-implant interactions, etc. (Artmann, G. M., et al., Biophysical Journal. 72(3):1434-41, 1997; Sung, K. L,. et al., Journal of Immunology. 158(2):919-27, 1997; Kwon, S. Y., et al., Journal of Orthopaedic Research. 18(2):203-11, 2000; Olbrich, K., et al., Biophysical Journal. 79(1):321-7, 2000). The affinity of osteoblasts for a bony surface and a resorption lacunae was disclosed herein as very "sticky" relative to control cells (i.e. lymphocytes, neutrophils, etc.).

It has been demonstrated that a number of lysosomal enzymes are used by the osteoclast during bone resorption. Some of the more well studied are: i) cathepsin B, ii) cathepsin G, iii) cathepsin L, iv) cathepsin K v) lysozyme, vi) -galactosidase, and vii)-glucuronidase.

Examination of these enzymes as a "bait" for the phage libraries will allow us to determine if there is a common moiety on the enzymes for binding (such as mannose-6-phosphate containing oligosaccharides) or if any of the clones with high affinity for TRAP cross react with any of the other lysosomal enzymes. These experiments will be performed using both the random phage display library and the osteoblast cDNA phage display library. The methods we will employ are those used to generate the data in the Preliminary Studies section. Molecules other than lysosomal enzymes may remain (or become exposed) on the resorption surface.

d) Identification of Phase Clones With High Affinity Binding to Authentic Resorption Lacunae The phage display technique can be used to identify molecules that interact with authentic resorption lacunae. The unique nature of this technique makes these experiments feasible even though both the library and the "bait" are unknown variables. That is, with either a random phage display library or an osteoblast cDNA phage display library it is not required to know which phage clones will show an affinity for a particular substrate. Moreover, one does not need to know what the substrate will be. Nevertheless, phage with high affinity for resorption lacunae are easily characterized and the corresponding binding substrate can be easily identified.

Specificity for the resorption lacunae was enhanced by removing the majority of library phage that demonstrate an affinity for bony surfaces that are not covered with lacunae. This was achieved by first subtracting the phage in the disclosed libraries that have affinity for bone by exposing the libraries to un-pitted bone wafers. The phage titer for the libraries used herein has been shown herein to be decreased by approximately 25% when unpitted bone wafers are used as a subtraction substrate. Subtraction of phage library molecules that bind un-pitted bone wafers was obtained by three rounds of biopanning. Thus, minimal non-specific binding will occur when pitted wafers are used as bait. To optimize selection, bone wafers with 40-60% of the area covered with osteoclast lacunae. Control experiments to be performed for these studies include: i) measuring the affinity of phage for resorption lacunae after boiling or extraction of the bone wafer, ii) using wild type phage to measure non-specific interactions, iii) demonstrating localization of phage within the lacunae as in FIG. 9

Upon identification of a phage clone with high affinity for a resorption lacuna the nucleic acid from the enriched phage can be cloned and sequenced to identify the structure of the molecules recognizing resorption lacunae and pitted bone wafers. All of the characterization disclosed herein of identified molecules can be performed on the molecules identified in these selection activities.

The "bait" protein can be identified by a co-precipitation technique. Precipitation of a phage clone carrying its bait protein is accomplished with polyethelene glycol precipitation (PEG) (50). A protein extract from pitted bone wafers can be prepared by either boiling (as in FIGS. 9 and 10) or gentle detergent treatment. The selected phage can then be added to the extract, allowed to incubate and cleared from the solution by stepwise addition of PEG. Recovery of the phage by centrifugation and elution of the bait protein can be followed by electrophoretic separation (Schmaljohn C. et al., Virology. 258(1):189-200, 1999). If there is more than one protein band that is eluted from the phage the major substrate can be identified with Far Western technology as shown in FIGS. 8 and 10. The protein band can then be sequenced. This will give information about which molecule in the resorption lacuna was acting as bait for the particular phage.

e) Manipulation of TRIP and GPC-4 Expression—"Gain of Function/Loss of Function"

The levels of GPC-4 and TRIP gene products can be manipulated. This can show that the gene products to demonstrate that they influence osteoblast differentiation (using reporter systems) and binding to resorption surfaces (using a high resolution imaging and micromanipulator system).

(1) TGFβ Signaling Pathways

TGFβ signaling evokes a number of complex and sometimes qualitatively different responses in cells from the skeleton. TGFβ can be a differentiating agent in growth plate chondrocytes and conversely it can stimulate proliferation and prevent differentiation in sternal and proliferating chondrocytes. In osteoblasts TGFβ has been shown to both increase and decrease alkaline phosphatase levels depending on the cofactors present, the cell line used, the substrate on which the cells are grown and the number of passages for the cells (Kassem M., et al., European Journal of Clinical Investigation. 30(5):429-37, 2000; Yamada T., et al., Histochemical Journal. 31(10):687-94, 1999; Chung C Y., et al., Biochemical & Biophysical Research Communications. 265 (1):246-51, 1999; Cheifetz S. et al., Connective Tissue Research. 35(1-4):71-8, 1996; Harris S E., et al., Journal of Bone & Mineral Research. 9(6):855-63, 1994; Bonewald L F., et al., Bone & Mineral. 17(2):139-44, 1992). Disclosed herein, TGFβ stimulates alkaline phosphatase activity from freshly isolated osteoblasts. This observation supports the following analysis.

Figure 4:
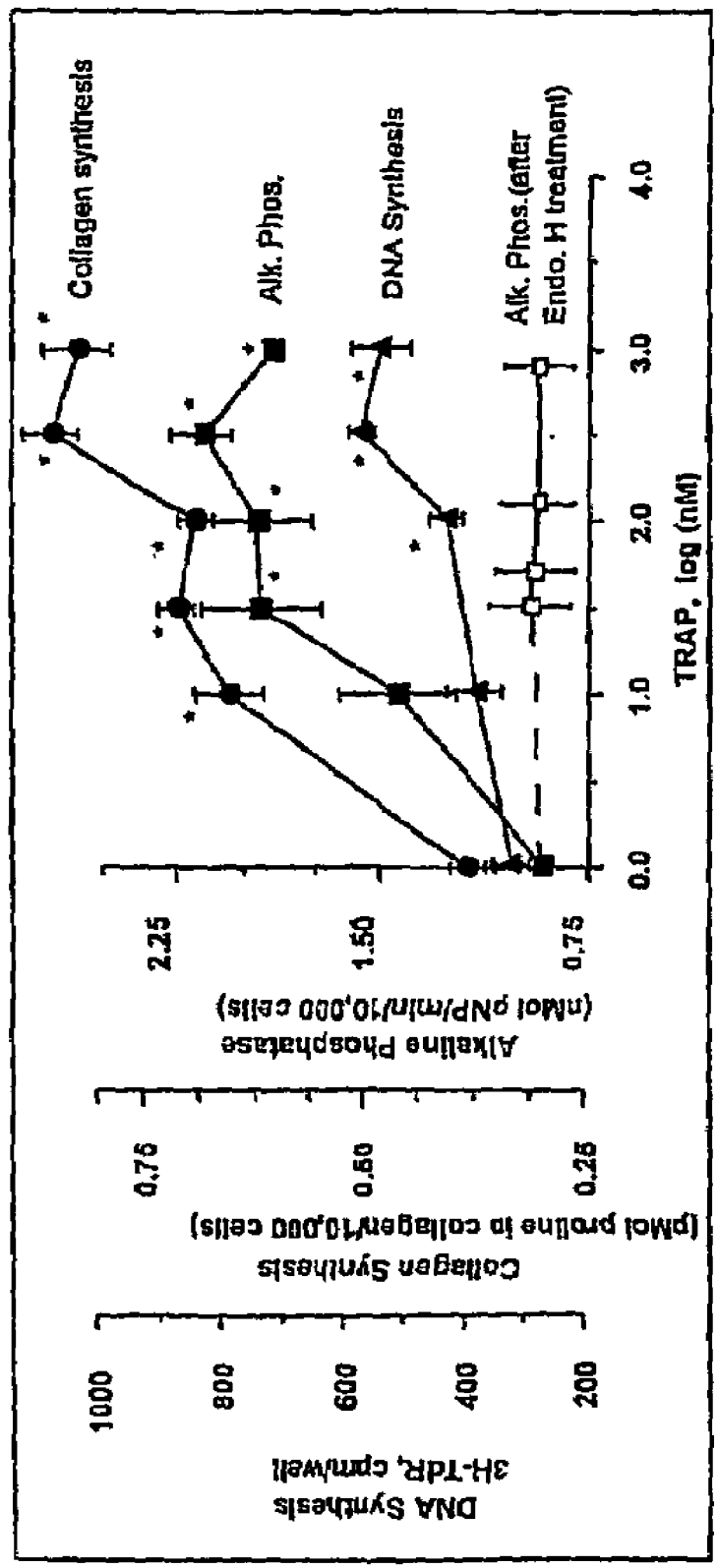
Figure 5:
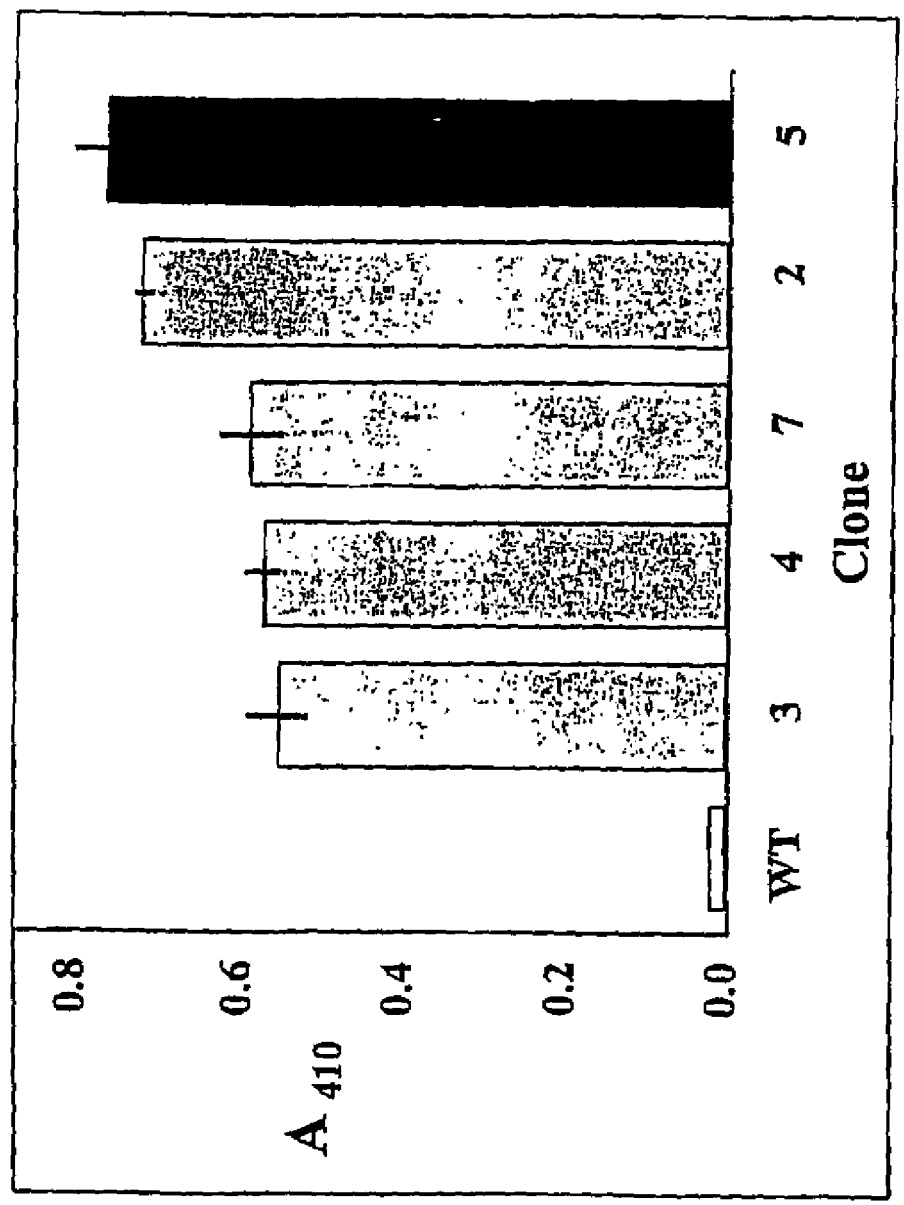

Disclosed herein, TRAP can activate TGFβ signaling (FIG. 9). This was demonstrated with a TGFβ promoter/reporter construct that is specifically sensitive to the Smad3/Smad4 transcription factor complex. It was also shown that TRAP can stimulate osteoblast differentiation as measured by a stimulation in alkaline phosphatase activity (FIG. 4). This is consistent with TRAP stimulation being mediated by TRIP and the Smad3/Smad4 transcription factor complex.

Figure 11:
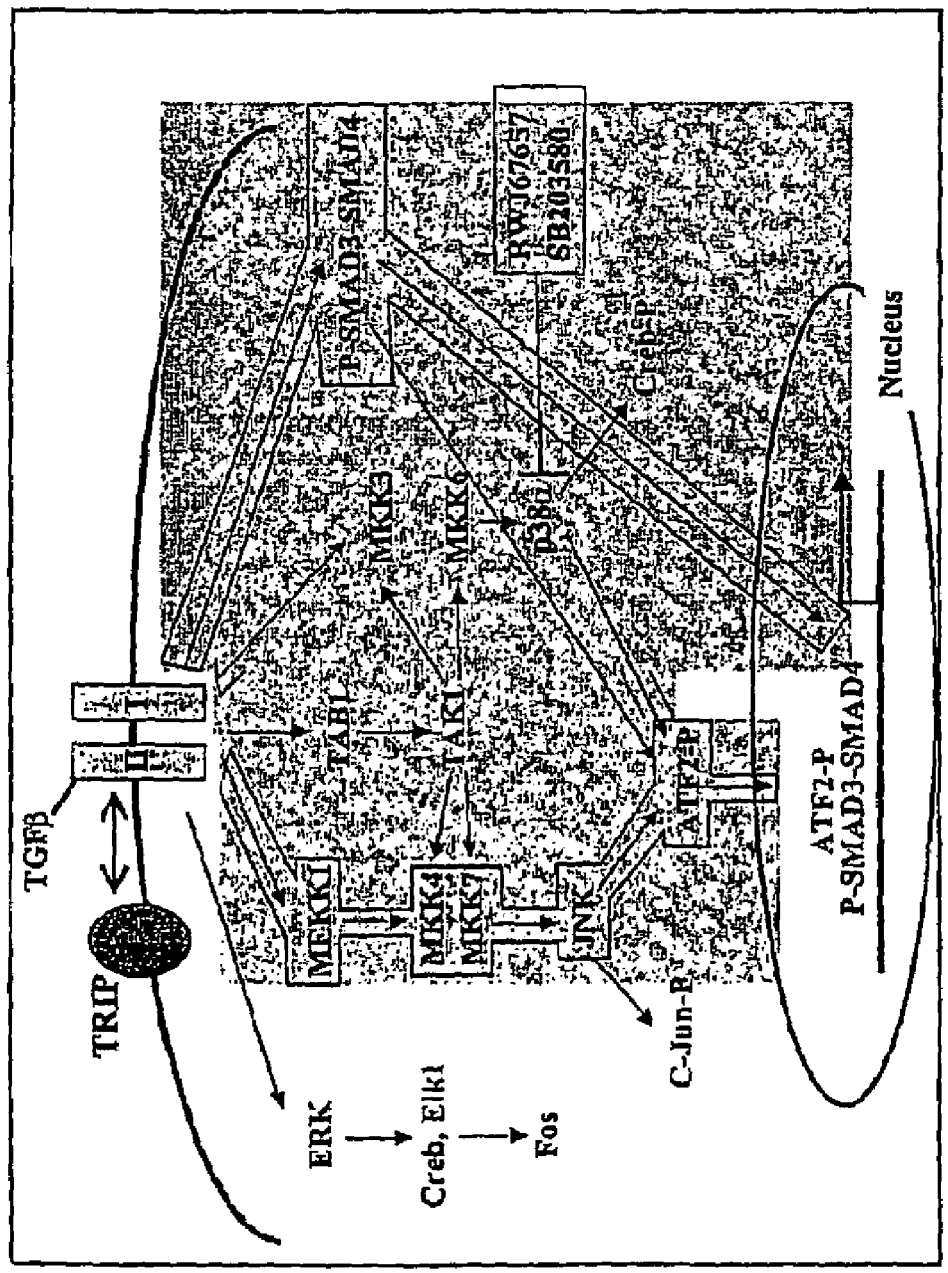

TGFβ activation pathways have been elucidated and are presented in FIG. 11. Three main pathways arrive at two transactivating transcription factor complexes: the JNK pathway, p38 pathway and Smad pathway. These three routes of signaling have been highlighted in the figure.

Two potent inhibitors of the p38 pathway exist. They are RWJ65657 and SM203580 and can be used to identify this pathway.

Binding of TGFβ to its type II receptor recruits and phosphorylates the type I receptor. The activated type I receptor then phosphorylates Smad3 which can, in its activated state, bind to Smad 4. This complex translocates into the nucleus where it interacts with other co-factors to elicit gene transcription. The other two pathways rely on MEKK/JNK and p38 phosphorylation steps to activate ATF-2, another TGFβ transcription factor. It is shown herein that the Smad pathway (P3TPlux) can be activated by TRAP (FIG. 9) and it can be determined whether TRAP can utilize either (or both) the JNK and p38 pathway. This can be accomplished with a ATF-2 reporter construct (see Detailed Methods of Procedure) and two specific inhibitors of the p38 pathway, namely, RWJ67657 and SB 203580. Both of these compounds have been gifted to us (by Johnson & Johnson and Smith Kline Beecham, respectively). They act as potent inhibitors of the p38 kinase (Barancik M., et al., Journal of Cardiovascular Pharmacology. 35(3):474-83, 2000; Tindberg N., et al., Neurochemical Research. 25(4):527-31, 2000).

Osteoblasts can be transfected with the ATF-2 reporter and examine the effect of both TGFβ signaling (positive control) and TRAP signaling. Dose response experiments with both TGFβ and TRAP will be performed to determine the maximum effective concentration. Subsequently, this can be repeated in the presence of either RWJ67657 or SB203580, again over a range of doses. Toxicity of the compounds will be monitored with a MTT assay. The sub-toxic dose response curves, when compared to control curves, will reveal to what extent the JNK pathway is utilized by TGFβ and TRAP in osteoblasts. That is, if complete inhibition of ATF-2 signaling occurs with either of the inhibitory compounds then it can be assumed that little or no regulation occurs through the JNK pathway. If incomplete inhibition occurs then the fraction of signaling utilized the JNK pathway can be determined.

A dominant negative Smad3 construct (see herein) can be used to determine to what extent the JNK/p38 pathway or the Smad pathway plays in the actual alteration of the osteoblast phenotype. The Smad pathway can be completely blocked using these techniques. A normal stimulation of alkaline phosphatase under these conditions would argue for the JNK/p38 pathway as being the dominant mechanism for changing the phenotype. The signaling experiments with the ATF-2 reporter (described herein) indicate which pathway (i.e. JNK or p38) was dominant.

The first approach has been utilized in the literature to investigate the interaction of TRIP with the type II TGFβ receptor (Choy L. and Derynck, R., J. Biol. Chem. 273: 31455-31462 (1998)). The strategy for these experiments is to transfect TRIP-negative cell lines with the construct and examine the effect of TRAP on TGFβ signaling. Three TRIP-negative cell lines have been used in the past. They are HaCaT, a keratinocyte cell line, COS-1 cells and Mv1Lu (mink lung cells). (It is of interest that the mink lung cell line used for so many years to assay TGFβ levels is TRIP-negative). In principle co-transfection assays will be performed (see Detailed Methods of Procedure) for both TRIP and either the ATF-2 reporter or P3TPlux (the Smad reporter). The resulting cells will be exposed to TGFβ as a positive control to determine responsiveness and gauge the level of reporter activity. They will then be exposed to TRAP as in FIG. 9. The effect of TRAP (both alone and in combination with TGFβ) will then be used to draw a conclusion about whether TRAP activation of the cells is mediated through TRIP.

A mammalian two hybrid system can be used to show the interaction of TRAP with TRIP (Sugawara T., et al., Endocrinology. 141(8):2895-903, 2000; Shioda T., et al., Proceedings of the National Academy of Sciences of the United States of America. 97(10):5220-4, 2000;Tagami T., et al., Biochemical & Biophysical Research Communications. 253 (2):358-63, 1998), as it was described herein for GPC-4. Much of the material is available in kit form. In principle, GB133 cells containing a green fluorescence protein (GFP) gene under the control of a galactosidase promoter can be purchased and used as the starting cell type. This cell is easily stably transfected with a GAL4-fusion protein construct. GAL4 binds to the galactosidase promoter and the fusion protein is the "bait" protein of interest. The cells are then transiently transfected with a protein of interest in a construct containing the EBNA-1 transactivating domain. If the two target proteins interact, transcription of GFP proceeds and the product can be easily detected by fluorescence microscopy or UV spectroscopy. All of the materials needed to produce the constructs and effect the transfection are available from CLONETECH and Stratagene.

f) Up Regulation of GPC4 and TRIP

Constructs containing GPC4 exist for transient transfection (Kleeff J., et al., Pancreas. 19(3):281-8,1999; Song H H., et al., Journal of Biological Chemistry. 272(12):7574-7, 1997; Steinfeld R., et al. Journal of Cell Biology. 133(2): 405-16, 1996. which are herein incorporated by reference at least for the material related to GPC 4 constructs). These constructs can be engineered to contain the enhanced green fluorescent protein gene (GFP) (typically upstream). The eGFP plasmid is available from CLONETECH in the form of a CMV driven internal ribosomal entry site construct (P-CMV-IRES-eGFP). Cloning of the glypican gene into this plasmid will allow for the expression of glypican-4 as well as eGFP from the same DNA. The internal ribosome entry site (IRES) allows the cells to translate both the inserted gene (glypican-4) and eGFP simultaneously. Thus, any cell glowing green under UV light should also be transfected with glypican-4. GFP-positive cells can be selected, one-by-one, for examination in the single cell attachment system. Data generated as in FIG. 10 will be used to demonstrate an effect of glypican-4 on attachment.

In addition to osteoblasts, glypican-negative cells can also be transfected. For example, neutrophils and two prostate cancer cell lines (DU-145 and LnCap) have previously been shown not to have affinity for bone or resorption surfaces (Lewis, G. D., et al., Trans. Orth. Res. Soc. 23:161, 1998). Positive results with these experiments would document the independence of glypican-4 in attachment to bone.

Controls include transfection with only eGFP, extraction of resorption surfaces (see FIGS. 9 and 10) and addition of heparan sulfate to the binding medium. (Glypican-4 is a heparan sulfate proteoglycan and heparan sulfate will compete for binding sites.)

For "loss of function" experiments for glypicans there does exist an effective antisense construct (Kleeff J. et al., Pancreas. 19(3):281-8,1999; Kleeff J. et al., Journal of Clinical Investigation. 102(9):1662-73, 1998) and anti-sera. This construct can be used upstream of an IRES for eGFP (as described above for expression of glypican-4). Glypican protein levels will be assayed with ELISA's and correlated with the extent of GFP production. Cells can be selected on a one-by-one basis with fluorescence microscopy for use in the attachment studies. Direct experiments with anti-sera to glypican-4 can also be performed.

After expressing GPC-4 and TRIP on exogenous vectors in cells including osteoblasts, upregulation of cellular binding to osteoclast lacunae occurs in GPC4 transfected cells and TGHβ signaling pathways are upregulated in TRIP transfected cells. These transfected cells would be suitable for ex vivo therapies which involve placing the transfected cells into contact with bone. This could occur for example during surgery to repair a break in the bone.

A commercially available cloning system from Life Technologies (a division of Invitrogen corp. www.lifetech.com) was used to clone both the GPC4 and TRIP sequences into multiple different vectors. These vectors can be found in the Clonetech vector catalog, which is incorporated by reference herein for vector material. The system uses a phage recombination reaction rather than restriction endonucleases and ligase. Recombination by phage occurs during the lytic phase of phage growth at specific DNA recombination sequences (ATT). Specific proteins that mediate the phage recombination are provided by Life Technologies. One series of reagents is used to move a particular sequence into an "expression clone". A second series of reactions moves the sequence from the "expression clone" to an "entry clone". The recombination reactions are equivalent to highly specific cutting and ligation reactions but they are improved because they are perfectly conserved and there is no need for the synthesis or loss of nucleotides. Although, general recombinant biotechnologies involving for example cutting and ligation could also be used, which are known to those of skill in the art.

Expression plasmids containing a strong promoter (CMV promoter) upstream of either GPC4 or TRIP sequence which was upstream of an IRES sequence and green florescent protein were constructed. The IRES sequence stands for internal ribosomal entry site and the green flourescent protein fluoreces under UV light. The reason for this construct was to produce both the GPC4 or TRIP along with the green fluorescent protein on the same gene in cells. Thus, cells glowing green under UV light indicate that the GPC4 or TRIP had also been expressed. This is because these sequences were upstream of the green fluorescent protein. These experiments gave "transfection efficiency" of the system. The efficiency approached 50%.

Under the influence of the CMV promoter high levels of GPC4 and TRIP can be produced. Tissue specific promoters to over-express and under-express the genes can also be used and are known in the art. This will allow control of the molecules selectively in osteoblasts. Tissue specific promoters used in the literature for these types of experiments are the osteocalcin promoter and the cbfa1 promoter. Both of these genes are only expressed in osteoblasts.

In the next series of experiments the same cloning techniques were used without the green fluorescent protein. In these experiments it was shown that expression of GPC4 or TRIP would alter the behavior of our cells as expected. That is, expression of GPC4 in GPC4-deficient cells would enhance their binding to bone and expression of TRIP in TRIP-deficient cells would activate the TGF beta signaling pathway. A number of different cell types have been tested, such as fibroblasts, prostate cancer cells, fibroblast cell lines, osteoblast cell lines and freshly isolated osteoblasts Transfection of bone cells ex vivo and then re-implantation of the cells into humans has been performed. Evans C H. Ghivizzani S C. Oligino T A. Robbins P D. Future of adenoviruses in the gene therapy of arthritis. Arthritis Research. 3(3):142-6, 2001 and Ghivizzani S C. Oligino T J. Glorioso J C. Robbins P D. Evans C H. Gene therapy approaches for treating rheumatoid arthritis. Clinical Orthopaedics & Related Research. (379 Suppl):S288-99, 2000 have shown that ex vivo gene therapy for specific molecules may be an effective way to treat musculoskeletal diseases such as rheumatoid arthritis. The same strategy for transfecting human osteoblasts with either GPC4 or TRIP can be used to augment bone formation at fracture sites, around implants, at bone grafting sites and systemically in osteoporosis patients. Technology exists to achieve a high efficiency transfection and to re-implant cells at specific sites.

g) Osteoblast Gene Expression Profile Assay

Both GPC4 and TRIP have been used in the creation of an osteoblast gene expression profile assay. This assay utilizes cDNA primer pairs that can be used to amplify a number of osteoblast gene products with real-time PCR. In addition to GPC4 and TRIP the following are assayed; osteocalcin (a bone specific protein), alkaline phosphatase (an enzyme present in large amounts in osteoblasts, cbfa1 (a transcription factor that induces osteoblast differentiation), PTH receptor 1 (the receptor responsible for PTH action), PTH receptor 2 (a secondary receptor that may be responsible for PTHrP action).

Results from these assays demonstrated that lead, which is known to have an adverse effect on bone formation, depresses all of the above gene products including GPC4 and TRIP.

The data are interpreted by analyzing an increase in PCR cycle number, i.e. the number of PCR cycles necessary to obtain product. The higher the cylce number the smaller amount of starting mRNA. Table 6 displays representative data.

TABLE 6

|  | Control PCR cycle number | Lead PCR cycle number |
| --- | --- | --- |
| GPC4 | 19 | 24 |
| TRIP | 21 | 26 |
| osteocalcin | 23 | 26 |
| alkaline phosphatase | 23 | 27 |
| cbfa1 | 24 | 28 |
| PTH receptor 1 | 28 | 33 |
| PTH receptor 2 | 31 | 32 |

These data demonstrate that the heavy metal ion, lead, can alter osteoblast gene expression. It also suggests that other regulatory agents will also be able to modify these genes. Most importantly, the data validate the importance of GPC4 and TRIP as participants in defining the osteoblast phenotype.

2. Example 2

Detailed Methods of Procedure for Example 1 a) Formation of Osteoclastic Resorption Pits

Bovine diaphyseal cortical bone wafers (4×4×0.3 mm) cut with a low speed diamond saw (Buehler, Evanston, Ill.) are used as a substrate for osteoclastic resorption. Wafers are placed into 70% ethanol and cleaned by ultrasonication for 15 min followed by multiple rinses in sterile PBS and sterile water. Bone wafers are dried and stored at −20° C.

Osteoclast containing cell preparations are obtained from 4-6 day-old euthanized rat pups. Long bones (femurs and tibias) are removed, freed of adherent soft tissues, and curretted with a scalpel blade in 1.0 ml/animal isolation media, pH 7.2.(Minimal Essential Medium+Earles salts (Gibco, #51200), buffered with 20 mM HEPES containing Nonessential Amino Acids, L-Glutamine, heat-inactivated Fetal Bovine Serum-10%, and Penicillin/Streptomycin). The cell suspension is triturated with a pipette (10-20×) followed by a 10 s settling period for larger pieces to sediment. Supernatant cell suspension is then removed and aliquoted into 100 ul portions to be added to a 96 well culture dishes containing the wafers (one wafer/well). Bone wafers are pre-wetted with the above isolation medium. The cell suspension is allowed to incubate with the bone wafers for exactly 20 min at 37° C. Wafers are then washed in warm, sterile PBS for 4-6 seconds, and placed in incubation medium (isolation medium minus HEPES) containing 1×10-8 M PTH, pH 7.25, (150 ul/slice). Scanning electron micrographs of one of these osteoclasts resorbing a cortical bone wafer were performed. Since there is no immune system in these cultures, we have found no problem with rat osteoclasts resorbing bovine bone. Typically the cell created two osteoclast lacunae (pits) in a cortical bone wafer.

b) Quantification of Number and Extent of Resorption Lacunae:

The entire bone wafer was digitally photographed at 200× magnification using a JVC TK-1070U video camera and Olympus BH-2 microscope attached to a Macintosh IIci computer with a Colorsnap frame-grabber board. The number and area of osteoclast lacunae are quantified with Osteometrics® software (Osteoclast lacunae were stained. The outlines of the lacunae are traced (dotted lines). The number of pits, total area resorbed and the area per pit are calculated.). A minimum of six wafers is used to analyze each concentration of factor or cell culture.

c) Osteoblast and Osteoprogenitor Cell Isolation

Thin plates of bone from the parietal segments of the neo-natal rat calvaria are dissected by first removing the entire calvarium from the rat pups and then trimming away the unwanted tissue. The procedure is performed aseptically.

The enzymatic digestion of these fragments is performed by the following method: During dissection the parietal fragments (2/calvarium) are stored in a shallow pool of isolation buffer (see below) in a plastic culture dish. The fragments are then incubated in a buffer (2.5 calvaria/ml) containing bacterial collagenase (Sigma, 0.5 mg/ml) for a total of 100 minutes. The incubation vessel is a polypropylene 50 ml beaker in a 37° C. oscillating water bath (1 Hz). Cells are collected at each of five 20 minute intervals (Fractions 1-5) by decanting the enzyme containing solution into tubes and centrifuging for 3.0 minutes at 500×g. Digestion for longer periods of time does not release any more cells. During the centrifugations the calvarial fragments are returned to the 37° C. water bath (without shaking) to keep them at constant temperature. The supernatant enzyme solution is then returned to the calvarial fragments for the next 20 minute digestion. The cell pellet is washed by resuspension and centrifugation in the isolation buffer. Cell counts in each period are performed with a hemocytometer. Cells recovered from the early periods are stored in isolation buffer at 37° C. until the digestion of the calvarial fragments is complete.

Isolation buffer is composed of: 25 mM HEPES, 10 mM NaHCO3, 100 mM NaCl, 3 mM K2HPO4, 12 mM mannitol, 24 mM KCl, 1 mM CaCl2, 5 mg/ml glucose, 2 mg/ml bovine serum albumin, 100 units/ml penicillin, 100 ug/ml streptomycin, pH 7.4.

The collagenase enzyme is obtained by screening a number of preparations from Sigma. The criteria for selection is 1) minimal cell damage (assessed microscopically), 2) maximum yield of cells per calvarium and 3) greatest viability after plating. The chosen lot of enzyme is then purchased in quantity and further treated with N-tosyl-L-lysine chloromethyl ketone (TLCK), a clostripain inhibitor. The treatment consisted of a 20 minute incubation of the enzyme with the TLCK with subsequent extensive dialysis against water at 4° C. The enzyme preparation is then lyophilized and stored at −20° C. in 500 ug aliquots.

Culture of the cells is by standard cell culture techniques. Usually the cells from each of the five fractions are diluted to 25,000 cells/ml in culture medium and plated at 125 cells/mm2 in 16 mm tissue culture multiwells.

The culture medium consists of a balanced salt solution containing MEM amino acids (Gibco), and BGJ vitamins (Gibco). Penicillin (100 units/ml) and streptomycin (100 ug/ml) are also added to the medium. For most experiments the culture medium is supplemented with dialyzed fetal bovine serum protein at 2.0 mg/ml. The serum protein is prepared by dialyzing (10-12,000 MW cut-off) commercially available fetal bovine serum (Gibco) against many changes of water at 4° C. followed by lyophilization.

d) Cell Adhesion to Bone Matrix Surfaces

Transverse slices of bovine femoral diaphyseal cortical bone (4×4×0.3 mm), cut with a low speed diamond saw (Buehler, Evanston, Ill.) and sterilized by ultrasonication, served as the substrate for cell attachment studies. Confluent cells were radiolabeled with 3H-thymidine (5 Ci/ml) for 24 hours followed by a cold thymidine chase (0.1 mM) for 30 min. The cells were removed from the culture dish with trypsin/EDTA (5 min. incubation), centrifuged at 1500 rpm for 5 min. and the pellet resuspended in 4.0 ml of their respective media's+Penicillin/Streptomycin. The cells were then counted, diluted to 20,000-100,000 cells/ml, and the specific activity was determined (i.e. CPM/cell). 4000-20,000 cells (200l) were subsequently added to each wafer and allowed to incubate (37° C., 5% CO2) for exactly 10 min. The wafers and cells were then washed with gentle agitation. The extent of 3H-thymidine label remaining on the wafers was measured in a scintillation counter. The number of cells attached to the wafer surface was calculated from the specific activity.

e) DNA Constructs

Wild-type and dominant negative mutant cDNA (C-terminal truncation, c) of human Smad 1-3 were a gift from Dr. Rik Derynck, and subcloned into the mammalian expression vector pCMX and into the replication competent avian sarcoma retrovimis RCASBP(A). Wild-type Smad1-3 and dominant negative Smad1-3c sequences were verified following subcloning using automated sequencing. The TGF-responsive p3TP-Lux reporter construct and the dominant negative type II TGF receptor was a gift from Dr. Joan Massagué.

f) Transient Transfection and Luciferase Assay

Osteoblasts, cultured at 30-40% confluence in 6-well plates, are transfected on day 2 after plating using the transfection reagent Superfect (Qiagen Santa Clarita, Calif.) according to the manufacturer's guidelines. Individual experiments are internally controlled for amount of total plasmid DNA, with equal amounts of p3TP-Lux reporter, control SV40-renilla plasmid for normalization of transfection efficiency, and target construct and/or vector control DNA for all co-transfection experiments. Following transfection, the cells are placed in media containing DMEM, Penicillin/Streptomycin, and 10% NuSerum IV. After 12 hours, they are incubated for 6 hours in serum-free media (containing DMEM, hyaluronidase 4 U/ml, Penicillin/Streptomycin, and supplemented with 10 pM triiodothyronine (Sigma, St. Louis, Mo.), 60 ng/ml insulin, and 1 mM cysteine (Sigma, St. Louis, Mo.)) plus the factor or cytokine of interest. Eighteen hours later, the cells are harvested and assayed for luciferase activity using the Promega dual luciferase assay system. Renilla luciferase values were used to normalize each sample for transfection efficiency.

g) Western Blot Analysis

Proteins will be separated by SDS-PAGE and transferred to nitrocellulose. The blot will be stained with Ponceau S and the positions of the molecular weight standards marked. The blot will be blocked sequentially with solution 1 (1×PBS, 3% BSA, 0.05% Tween-20) and solution 1/10% normal goat serum (NGS). Primary antibody in solution 1/10% NGS will be incubated for 3 hrs with rocking at room temperature. The blot will be washed and secondary HRP-goat anti-rabbit in solution 1/10% NGS added for 45 min. The blot will be developed with 6% 4-chloronapthol in 20% methanol, 1×PBS, 0.036% hydrogen peroxide.

h) Screening of Phage Binding to TRAP by Phase ELISA, Far-Western and Scatchard Analyses Small-scale phage preparations, obtained from single colonies of the third round of affinity bio-panning were analyzed for binding to TRAP by phage ELISA. Briefly, in this method, selected phage at increasing concentrations were incubated for 2 hr at room temperature in TRAP or BSA-coated wells. Phage that bound to immobilized TRAP were detected by incubation with HRP-conjugated anti-M13 antibody (Pharmacia #27-9411-01), followed by incubation with HRP substrate (ABTS Sigma #A1888) and read at an OD of 410 nm.

A Far-Western technique was used to document that the selected phage were indeed binding to TRAP. In this procedure, increasing concentrations of TRAP (1-4 ug) and control proteins (BSA and RNase, 5 ug) were loaded in a 10% SDS-PAGE gel and electrophoresed. They were then transferred to PVDF membranes (NEN) and incubated with $10^{10}$ phage particles from selected clones at 4° C. for overnight. The membrane was washed in PBS with 0.5% [v/v] Tween 20 four times. An anti-M13 phage peroxidase-conjugated antibody at a dilution of 1:15000 was added and gently swirled at room temperature for an hour. In the last washing procedure, the membrane was incubated in PBS without Tween 20. Detection of the phage/antibody complex was accomplished using ECL-plus (Amersham) with the membrane being exposed to Kodak Biomax MR film for 30 seconds.

Phage affinity for TRAP was determined with a modified Scatchard analysis. In this analysis 96 well plates coated with a fixed amount of TRAP (10 ng/ml) were incubated with a serial dilution of phage (titer from $10^{12}$/ml~$10^9$/ml). After a one hour room temperature incubation, each well was washed with PBS with 0.5% [v/v] Tween 20 four times. The bound phage where then amplified directly in the wells by the addition of 100 ul of log-phase ER2537 (M13 bacteria host). The number of phage in each well was then determined with a standard plaque assay. For the non-specific binding estimation, the experiment was repeated in the presence of a 100 fold excess of TRAP. The bound and free fraction of phage were then determined.

i) Mammalian Two-Hybrid Assay

A mammalian two-hybrid assay was performed utilizing materials obtained from Clonetech (catalog #K1602-1). In this procedure we created two fusion proteins; a GAL4-BD-TRAP and a VP16-AD-GPC4. That is, TRAP was inserted into a plasmid containing a GAL-4 BD (binding domain) and glypican 4 (GPC4) was inserted into a plasmid containing the VP-16-AD (activation domain). The TRAP sequence was obtained from Dr. James Bixley, University of Missouri, Columbia, Mo. GPC4 was obtained from a human osteoblast cDNA library from MG-63 cells.

GAL-4-BD-TRAP binds to the promoter of a luciferase reporter gene and the VP-16-AD-GPC4 activates RNA polymerase II activity. If the two target proteins interact with each other they will bring the binding domain protein into the vicinity of the activation domain and luciferase transcription will occur. The presence of luciferase activity in co-transfected cells is evidence for a physical association between the proteins.

In a control experiment, a second VP-16-AD protein was constructed using a GPC4 sequence deficient in the 12 amino acids identified from Clone 5 phage biopanning. This construct is termed VP-16-AD-GPC412. Deletion of the 12 amino acids from the GPC4 gene was accomplished with linker scanning mutagenesis Pairs of plasmids were co-transfected into $SaOS_2$ osteoblast-like cells using Lipofectamine®.

j) In Situ Staining

To confirm that the phage recognized TRAP in a bone resorption lacunae we performed a binding assay in osteoclast pits prepared on cortical bone wafers in vitro. In this assay, osteoclast lacunae were formed by culturing neo-natal rat bone marrow cell isolates on cortical bone wafers in the presence of PTH ($1×10^{-8}$ M) for 10-14 days. The osteoclasts were removed by gentle scraping and washing. $10^{10}$ phage were then added to each wafer and incubated for 2 hours at room temperature. The wafers were washed four times in PBS and visualized with a primary anti-phage HRP conjugated antibody as described in the Far-Western technology presented above. For control experiments we removed TRAP from the lacunae by boiling the wafers for 2 minutes.

k) Competition Cell Binding Assay

To measure the effect of selected phage peptides on osteoblast binding in osteoclast lacunae we performed a cell binding assay in the presence of increasing concentrations of the phage peptide. Osteoblasts were prelabeled with L-[4, 5-$^3$H]Leucine (250 µCi TRK636-250 µCi, Amersham ) for 24 hrs. The osteoblasts were then added to pitted bone wafers in the presence of increasing concentrations of a synthetic 12 amino acid peptide that was identical to the phage sequence. After a two hour incubation at 37° C. the wafers were washed and the amount of radiolabel associated on each wafer determined by scintillation spectrometry. The specific activity of the cells (i.e. cpm/cell) was used to determine the number of cells adhering to the wafers.

l) Statistics

All data are presented as the mean±one standard error of the mean. Statistical significance was determined by ANOVA.

m) MTT Cell Viability Assay

MTT (3-(4,5-dimethylthiazol-2yl)-2,5-diphenyl tetrazolium bromide) conversion to formazan is used as a test for cell viability. To make the measurement, MTT is added to the cultures for 30 min and then the medium is aspirated from the wells. The insoluble formazan reaction product remains intracellular in the viable cells. To solubilize the formazan, 0.2 ml of isopropanol containing 0.04 N HCl was added to each well, and the plate was spectrophotometrically analyzed in an ELISA plate reader at an absorbence wavelength of 570 nm. Cell number is determined from sets of standard wells containing known numbers of cells.

n) DNA Assay and Thymidine Incorporation

Total DNA is measured with an assay specifically designed for quantification of small numbers of cells in culture. In this assay the culture medium is removed and the cells rinsed with 1 ml of 0.15 M NaCl. The cells are removed from the dishes by the addition of trypsin (0.05%) and EDTA (0.4 mg/ml) in a balanced salt solution containing 15 mM HEPES and no calcium or magnesium. The dishes are rinsed with an additional 0.25 ml of the HEPES buffer and pooled with the first extract. One milliliter of culture medium containing 2 mg/ml BSA is then added and the DNA precipitated by the addition of 0.5 ml of 50% trichloroacetic acid (TCA). The samples are chilled to 4° C. and centrifuged at 14,000×g for 30 minutes. The supernatant is re-moved and the pellet rinsed with 0.2 ml of 0.01 N potassium acetate in absolute ethanol at 4° C. The samples are then recentrifuged at 14,000×g for 10 minutes and the ethanol aspirated. The samples are then dried at 50° C. Standards are prepared from calf thymus DNA and also dried. A solution of 2.0 M diaminobenzoic acid is pre-pared in double distilled water to which is added 100 mg/ml activated charcoal. After stirring for 30 minutes, the suspension is filtered through a 0.65 mM filter to remove the charcoal. 0.1 ml of the resultant solution is added to each sample. After incubation for an additional 30 minutes at 50° C., 3 ml of 0.6 M perchloric acid is added to the samples. The DNA is quantitated by fluorescence spec-trophotometry of the samples with an excitation at 408 nm and emission at 500 nm. The sample values are calculated from a linear regression analysis of the DNA standards.

De novo DNA synthesis is measured with radiolabelled thymidine incorporation. In this assay the cells are exposed to 2.0 Ci of radiolabelled thymidine (methyl-3H-thymidine, Amersham) at a final concentration of 5.0 M for two hours. Following the exposure, the radioactive medium is discarded, the cells removed, and the DNA acid precipitated by the addition of perchloric acid. Following centrifugation the supernatant is discarded and the pellet is redissolved in NaOH. Acid-insoluble radioactivity is determined by liquid scintillation spectrometry. Standards of the radiolabelled medium are prepared for the direct estimation of the incorporation of femtomoles of thymidine into DNA.

Detailed methods have been previously published for: ELISA (Blaine T A, et al., J Bone Joint Surg 78(A):1181-92, 1996; Blaine T A, et al., J Bone Joint Surg 79(A):1519-28, 1997; Pollice P, et al., J Orthop Res 16:607-704, 1999), Northern blot (Blaine T A, et al., J Bone Joint Surg 78(A): 1181-92, 1996; Schwarz E M, et al., Proc Natl Acad Sci USA 90:7734-8, 1993), RNAse protection assay (Grimsrud C, et al., J Orthop Res 16:247-55, 1998), Western blot (Schwarz E M, et al., Genes Dev 11:187-97, 1997), EMSA (Schwarz E M, et al., Proc Natl Acad Sci USA 90:7734-8,. 1993; 78, 79), Luciferase reporter construct assays (Schwarz E M, et al., Proc Natl Acad Sci USA 90:7734-8, 1993), Immunohistochemistry and semiquantitative analysis (Schwarz E M, et al., J. Orthop. Res. In Press 1999; Hicks D G, et al., J Bone Joint Surg 78:482-96, 1996), Spleen cell osteoclast bone resorption cultures (Franzoso G, et al., Genes Dev 11:3482-96, 1997), Osteoclastogenesis assays (Franzoso G, et al., Genes Dev 11:3482-96, 1997; Takahashi N, et al., Endocrinology 122:1373-82, 1988), and Generation of stable cell lines (Schwarz E M, et al., J Virol 72:5654-60, 1998) which are herein incorporated by reference at least for the material related to the methods for which each was cited.

o) Vertebrate Animals

Sprague-Dawley derived white laboratory rats can be used. 5 timed pregnant female rats per week are preferred. The animals will be allowed to deliver their pups and can the 2-3 day old pups can be transported the to the laboratory for sacrifice and tissue preparation. The calvarial tissue of the pups will be the source from which we will isolated and culture cells from the osteoblast lineage. The long bone of the pups will be used for the isolation of osteoclasts.

Sacrifice of the 2-3 day old rat pups can be by any rapid decapitation after sedation by exposure to a 100% atmosphere of carbon dioxide. The level of sedation can be assessed by a pedal touch reflex prior to sacrifice.

3. Example 3

A Phage Display Technique Identifies a Regulator of Cell Differentiation a) Abstract 40 phage clones with very high affinity for TRAP were sequenced and of the clones with multiple consensus sequences we identified a regulatory protein that modulates osteoblast differentiation. This protein is the "TGFbeta receptor interacting protein" (TRIP-1). The data demonstrate that TRAP activation of TRIP-1 evokes a TGFβ-like differentiation process. Specifically, TRIP-1 activation increases the activity and expression of osteoblast alkaline phosphatase, osteoprotegerin, collagen and Runx2. Moreover, it was shown that TRAP interacts with TRIP intracellularly, that activation of the TGFβ type II receptor by TRIP-1 occurs in the presence of TRAP and that the differentiation process is mediated through the Smad 2,3 pathway. It is also demonstrated that osteoblasts, when cultured in osteoclast lacunae containing TRAP, rapidly and specifically differentiate into a mature bone forming phenotype.

b) Introduction

The formation of new bone during the process of bone remodeling occurs almost exclusively at sites of prior bone resorption. As there are one to two million active remodeling sites in an adult skeleton at any point in time (Parfitt A. M., The physiologic and clinical significance of bone histomorphometric data, in *Bone Histomorphometry: Techniques and Interpretation*. Robert R. Recker, ed., CRC Press, Boca raton, Fla., 1983, pp. 143-223), this spatial localization of formation plays a key role in maintaining skeletal architecture. Aberrant or disorganized formation could lead to architectural changes that would weaken skeletal structure.

Disclosed herein an osteoblast protein (TGFβ receptor interacting protein, TRIP-1) possesses very high affinity for TRAP and is poised for activating the TGFβ differentiation pathway in osteoblasts. TRIP-1 has been previously described in other cell types and has been shown to modulate TGFβ signaling in both a stimulatory and inhibitory fashion (Choy, L. and Derynck, R., J. Biol. Chem. 273: 31455-31462 (1998); Chen, R H., et al., Nature 377: 548-552 (1995)). In osteoblast systems TGFβ signaling pathways control osteoblast differentiation (Kassem M., et al., European Journal of Clinical Investigation. 30(5):429-37, (2000); Yamada T. et al., Histochemical Journal. 31(10):687-94, (1999); Chung C Y. Et al., Biochemical & Biophysical Research Communications. 265(1):246-51, (1999); Cheifetz S., et al., Connective Tissue Research. 35(1-4):71-8, (1996); Harris S E., et al., Journal of Bone & Mineral Research. 9(6):855-63, (1994); Bonewald L F. Et al., Bone & Mineral. 17(2): 139-44, 1992). This effect is modulated by the interaction of TRAP with TRIP-1.

c) Methods

Purified type V TRAP was obtained as a generous gift from Dr. R. M. Roberts, University of Missouri, Columbia, Mo. This enzyme, also known as uteroferrin, shares identity with osteoclast TRAP (Ling P, Roberts R M, Journal of Biological Chemistry. 268:6896-902 (1993)).

Cortical bone wafers were obtained by cutting 4.0×4.0× 0.3 mm sections from bovine femoral cortical bone obtained from a local abattoir.

Isolated osteoblasts were prepared from neo-natal rat calvaria as previously described (Martinez D A, et al., J.

Cellular Biochemistry 59: 246-257 (1995)). Alkaline phosphatase assays and standard Western analyses were performed as previously described (Ionescu A M. ET AL., Journal of Biological Chemistry. 276:11639-47 (2001)).

(1) Construction of a T7 Primary Rat Osteoblast cDNA Library

A T7 phage display library of rat osteoblast cDNAs was constructed from an existing primary rat osteoblast day 8 cDNA plasmid library generated from primary isolated rat osteoblasts. The cDNA inserts of the plasmid library were excised by digestion with EcoRI and NotI and inserted between the corresponding sites of an equimolar mixture of T7Select 1-1 vector arms (T7Select System Manual, Novagen). The resulting phage library contained $5.6 \times 10^7$ independent clones/mL, as determined by plaque assays. The library was amplified once by infecting a mid-log-phase Escherichia coli (BLT 5615 bacterial strain) culture (250 ml, $OD_{600}$ 0.6) with the phage library at a multiplicity of infection of 0.001. After cell lysis, the phage lysate was made in 0.5M NaCl, clarified by centrifugation, and stored at minus 80° C. The insert sizes of 24 individual clones as well as of the complete library were analyzed by PCR with the forward primer 5'-GGAGCTGTCGTATTCCAGTC-3' and the reverse primer 5'-AACCCCTCAAGACCCGTTTA-3'.

(2) T7 Phase Clone Biopanning Procedure

An aliquot of the amplified phages ($10^9$ pfu) were allowed to bind to TRAP which was immobilized on an ELISA plate for 2 h while rotating gently. Unbound phages were removed by washing ten times with 0.2 ml 1 M NaCl, 0.1% Tween-20 in PBS, pH 7.2, and further washed twice in 0.2 ml PBS and finally resuspended in 100 µl elution buffer (Novagen).

Ten microliters of the supernatant was used to determine the amount of detached phage in each round of selection. The remaining 90 ul of the supernatant was added to a 10 ml culture (OD 0.6) of E. Coli (BLT5615). The bacteria had been induced with 100 µl of 100 mM IPTG 30 min before phage addition, to ensure production of the phage capsid protein. Approximately two hours after phage addition the bacteria were lysed and the phage sublibrary was added to the ELISA plate (Nune, Rochester, N.Y.) coated with TRAP. After binding and washing the sublibrary, a new round of selection was started. Following two rounds of selection, 40 plaques were arbitrarily isolated from LB plates and each dissolved in phage extraction buffer (100 mM NaCl, 20 mM Tris-HCl pH 8.0 and 6 mM $MgSO_4$). In order to disrupt the phages, the dissolved material was mixed 1:1 with 10 mM EDTA pH 8.0 and heated at 65° C. for 10 minutes. The phage DNA was then amplified by PCR, using T7 SelectUP and T7 SelectDOWN primers (T7Select Cloning kit, Novagen). After amplification, the PCR fragments were purified by adding 1 ml 100% ETOH to precipitate the PCR product. The purified PCR fragments were then sequenced using ABI 377 Big Dye autosequence kit (Applied bioscience). Based on the sequence results, the predicted amino acid sequence displayed on the T7 phage capsid can be determined. The candidate clones were amplified and used to check the affinity to TRAP with an ELISA method.

(3) Phage ELISA and Far-Western

Small-scale phage preparations, obtained from single colonies of the third round of affinity bio-panning were analyzed for binding to TRAP by phage ELISA. Briefly, in this method, selected phage at increasing titers were incubated for 2 hr at room temperature in TRAP or BSA-coated wells. Phage that bound to immobilized TRAP were detected by incubation with HRP-conjugated anti-T7 antibody (Novagen), followed by incubation with HRP substrate (ABTS Sigma A1888). The absorbance was read at an OD of 410 nm.

A Far-Western technique was used to document that the selected phage were indeed binding to TRAP. In this procedure, two concentrations of TRAP and control proteins (BSA, 5 ug) were loaded in a 10% SDS-PAGE gel and electrophoresed. They were then transferred to PVDF membranes (NEN) and incubated with $10^{10}$ M13 phage particles from a GPC4 phage (Clone 5) which have been shown to have high affinity and high specificity for TRAP. The membrane was washed in PBS with 0.5% [v/v] Tween 20 four times. An anti-M13 phage peroxidase-conjugated antibody (Amersham Pharmacia) at a dilution of 1:15000 was added and gently swirled at room temperature for an hour. In the last washing procedure, the membrane was incubated in PBS without Tween 20. Detection of the phage/antibody complex was accomplished using ECL-plus (Amersham) with the membrane being exposed to Kodak Biomax MR film for 30 seconds.

(4) OPG Sandwich ELISA

ELISA plates were coated by overnight incubation with 0.1 ml of carbonate buffer (15 mM $Na_2CO_3$, 35 mM $NaHCO_3$, 0.02% $NaN_3$, pH 9.6) containing 1 µg/mL of anti-OPG antibody at 4° C. per well. The plates were blocked with 0.2 ml of 5% dry milk in PBS per well for 1 hr at 37° C. 200 µl of medium prepared from different treatment cells as described above were added and incubated for 1 h at 37° C. Samples and serial dilution of OPG standards were loaded in triplicate to the plates (0.2 ml/well). After washing with PBS-Tween (0.1%), the bound OPG was quantified by successive incubation with another detection antibody conjugated with biotin (1 hr each at 37 C). After incubation, the plate was washed with PBS-Tween for ten times and incubated with 100 ul Streptavidin with HRP-conjugated (1/10000 dilution from stock) for 30 min at room temperature. After incubation, the plates were washed with PBS-Tween. 0.2 ml of 2,2'-azinobis (3-ethylbenzthiazolinesulfonic acid) solution (ABTS Sigma #A1888) per well was added for reaction with horseradish peroxidase. The plate was then measured at 405 nm in an ELISA reader.

(5) Glutathione S-Transferase (GST) Fusion Protein Preparation and Pull-Down Assay GST-TRAP and GST-TRIP fusion proteins, and GST control protein were purified as instructed by the manufacturer (Amersham Pharmacia). Briefly, plasmids containing GST-fusion protein expressing cDNA were transformed into a BL21DE3)pLysS bacteria strain and selected for ampicillin and chloramphenicol resistant colonies. Selected colonies were grown in LB medium at 30° C. until $OD_{600}$ reached 0.6 to 1. Then 0.1 mM IPTG was added to medium for 3 hours. Bacteria were lysed by B-PER (Pierce) with 1 mM PMSF. Lysed bacteria were spun down and the supernatants were collected. The GST fusion proteins were pulled down by glutathione coated beads (Amersham) in 4° C. for 1 h then washed three times with NETN buffer (20 mM Tris/pH 8.0, 100 mM NaCl, 6 mM $MgCl_2$, 1 mM EDTA, 0.5% NP-40, 1 mM DTT, 8% glycerol, and 1 mM PMSF). The purified GST fusion proteins and beads were suspended in 100 µl NETN buffer. Resuspended GST-proteins and beads were incubated with 5 µg purified TRAP or RIPA lysed transfected cell lysate. After incubating for 1 h at 4° C. with agitation, the glutathione-coated beads were washed with NETN buffer four times then the protein complexes were loaded in SDS-PAGE and visualized by using the ECL-plus method.

(6) Mammalian Two-Hybrid Assay

Transfections were performed using the Panver LT-1 reagent method (Panvera) as described in the product sheet. Briefly, 1.5-3×10$^5$ cells were plated on 35-mm dishes for 24 h, and the medium was changed to DMEM containing 10% FBS 2 h before transfection. Cells were transfected with 0.5 µg of plasmids expressing a Gal4-DBD (DNA binding domain) fused with a full-length TRIP-1 cDNA or an anti-sense TRIP-1 cDNA and a VP-16AD (activation domain) fused with a TRAP cDNA as indicated. A Gal4 response element controlled firefly luciferase expression plasmid, pG5-Luc, was used as reporter gene. *A Renilla* luciferase expression plasmid pRL-SV40 was used as an internal control for transfection efficiency. The total amount of DNA was adjusted to 5 µg with pCMX vectors.

(7) Statistics

All data are presented as the mean±one standard error of the mean. Statistical significance was determined by ANOVA.

d) Results

Figure 14:
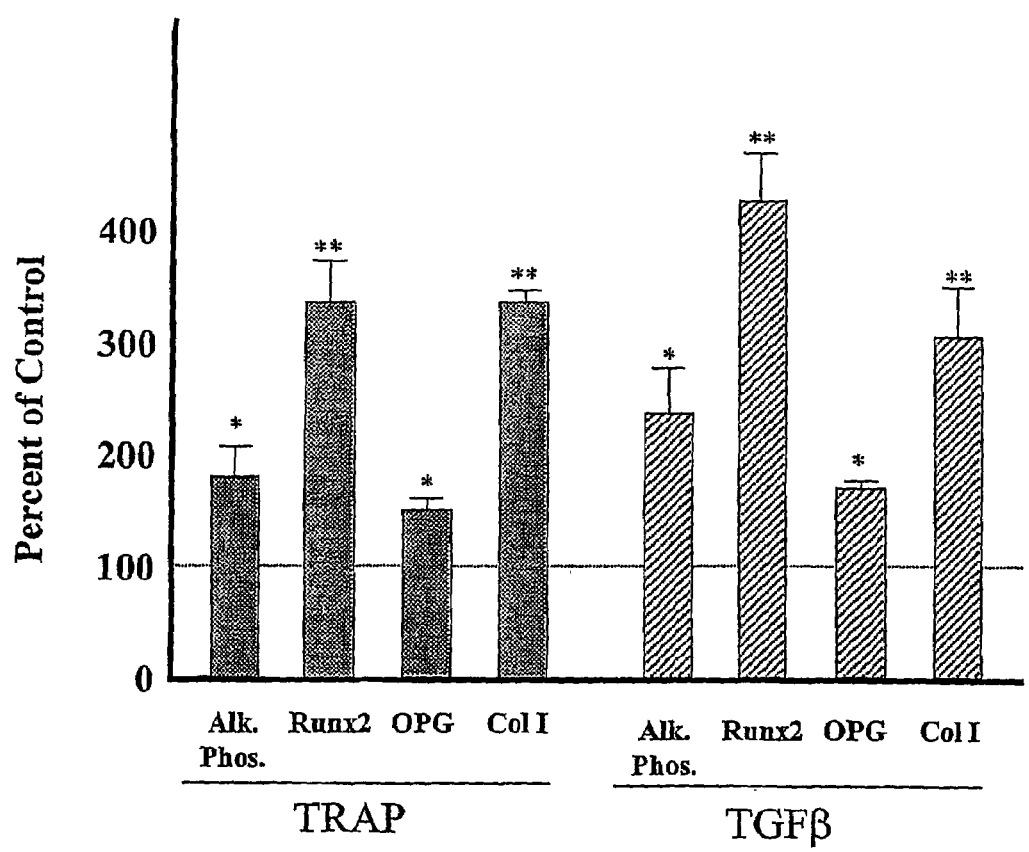

Osteoblast differentiation at sites of bone remodeling is mediated by a number of regulatory factors. One of the key factors is TGFβ. In most systems, including the typically the disclosed system, TGFβ is known to be a potent enhancer of the osteoblast phenotype. FIG. 14 shows that in the presence of TGFβ isolated osteoblasts show an increase in alkaline phosphatase activity, and an increase in Runx 2, osteoprotegerin (OPG) and collagen protein synthesis. In an exactly analogous fashion, TRAP demonstrates the same effect. Control phosphatases such as myokinase and ATPase have no effect on the cells.

The effect of TRAP on osteoblasts may be one mechanism by which the cells are induced to differentiate only at sites of prior bone resorption. In order to define what osteoblast proteins may be involved in this mechanism immobilized TRAP was probed with T7 phage that were expressing proteins from an osteoblast cDNA library. After three rounds of bio-panning 40 phage clones with very high affinity for TRAP were sequenced and analyzed. Three of the clones contained sequences that may be involved in osteoblast differentiation. They were type I collagen, Sox9, and TRIP-1. However, the sequences for type I collagen and Sox9 were from the 3' untranslated region of the messages. The TRIP-1 sequence, however, was from the coding region of the protein.

Figure 15:
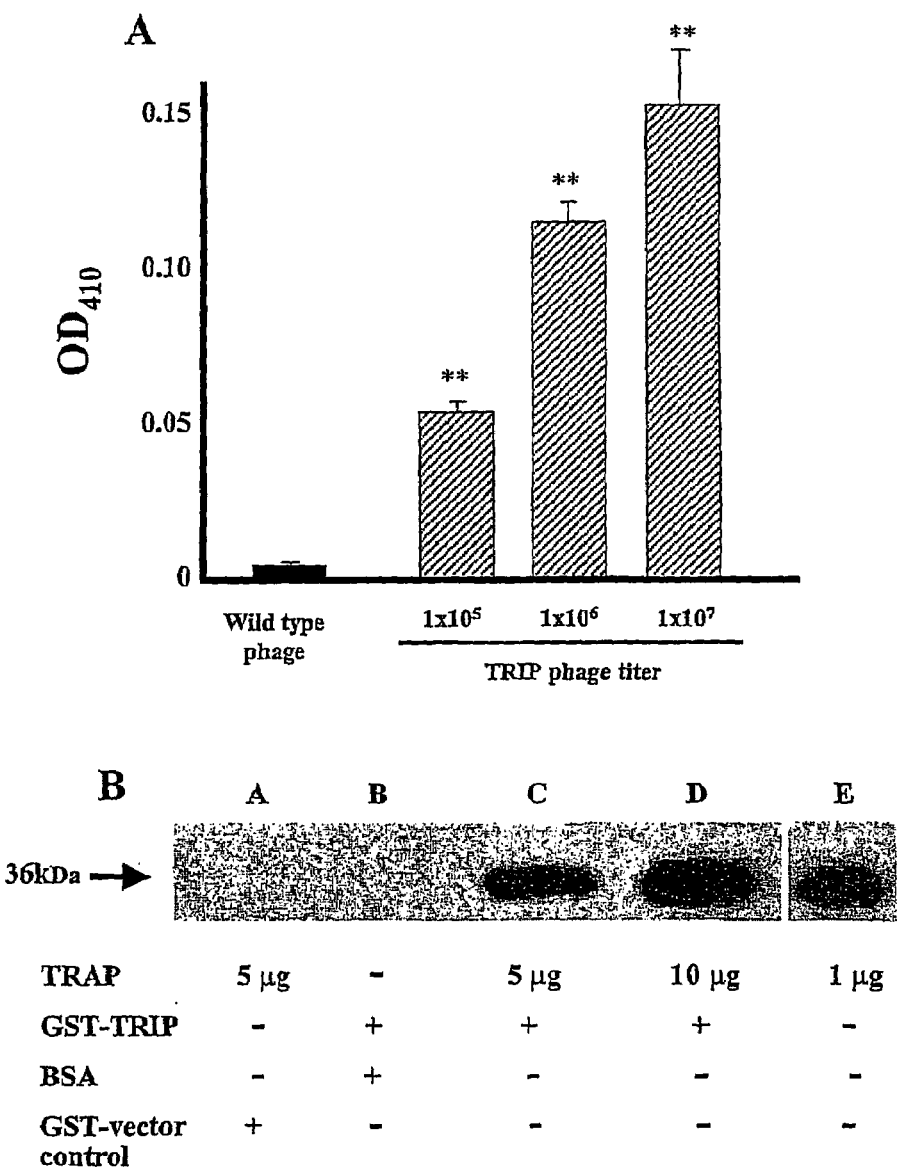

FIG. 15*a* demonstrates that the TRIP-1-expressing phage show a dose-dependent affinity for TRAP. FIG. 15*b* is a compilation of data that indicate the binding of TRIP-1 to TRAP is specific and of high affinity. For these experiments we prepared a plasmid construct with human TRIP-1 cDNA fused to glutathione-S transferase (GST-TRIP). As a control protein we utilized the GST vector alone. GST-TRIP and TRAP were incubated for 1 hour and any proteins associated with the GST-TRIP were extracted from the reaction mixture by incubation with glutathione coated beads. The proteins were analyzed by Far-Western analysis utilizing a phage clone with high affinity for TRAP. In lane A of FIG. 15*b* the control fusion protein does not have any affinity for TRAP as no TRAP protein can be detected. Lane B demonstrates that the GST-TRIP fusion protein has no affinity for any of the components of bovine serum albumin (BSA) and is not recognized in the Far-Western. Lanes C and D show that GST-TRIP has a dose dependent affinity for TRAP. Lane E is a positive control without glutathione bead extraction, demonstrating that TRAP can be detected in this Far-Western. These data document the affinity of TRIP-1 for TRAP and prove that the association does not depend on post-translational modifications of TRIP-1 as the protein was produced in bacteria and that the human sequence of TRIP has affinity for TRAP in the same way as the molecule from the rat cDNA library.

Figure 16:
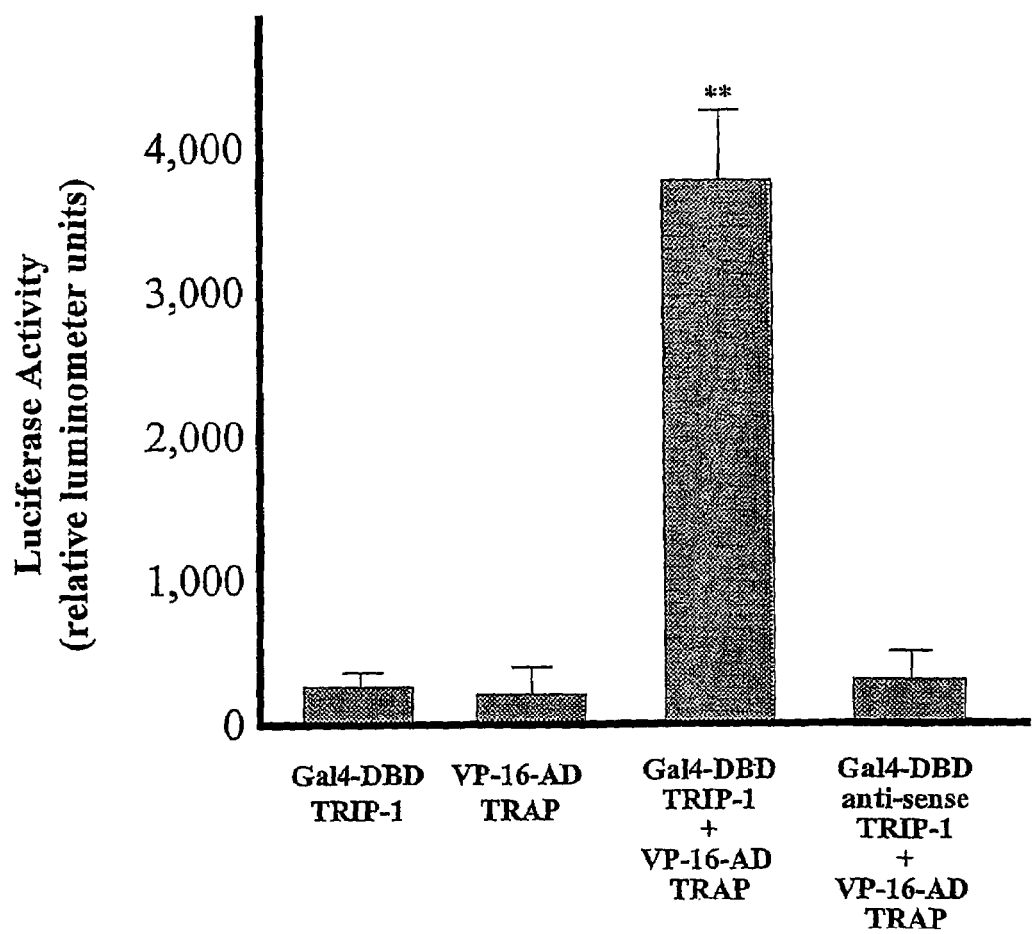

In order to demonstrate that TRIP-1 and TRAP can interact inside of cells we utilized a mammalian two hybrid system. In these experiments 293T cells were transfected with fusion proteins composed of TRIP-1 with a Gal4-DNA binding domain (DBD) and TRAP with a VP-16-activation domain along with a luciferase reporter gene. Single transfections with either fusion protein showed no increase in reporter activity, however, co-transfection with both fusion proteins showed a 20 fold increase in reporter activity (FIG. 16). Moreover, in a control experiment where anti-sense TRIP-1 was substituted in the Gal4-DNA binding domain, there was also no stimulation of the reporter gene. These data demonstrate that TRIP-1 and TRAP can interact with each other in a highly specific manner in the cytosol of cells. As a further confirmation that TRAP and TRIP-1 interact in the same cell compartment we performed fluorescent labeling co-localization studies. 293T cells were transfected with TRIP-1 tagged with red fluorescent protein (TRIP-RFP) and TRAP tagged with a green fluorescent protein (TRAP-GFP). The cells were examined for TRAP-GFP and TRIP-RFP under fluorescence confocal microscopy. The images from the two wavelengths were digitally superimposed and where red and green pixels overlapped we created a merged pseudo-color image. This image demonstrated that at the resolution of the microscope and digital image, TRAP and TRIP-1 co-localize inside of cells.

Figure 17:
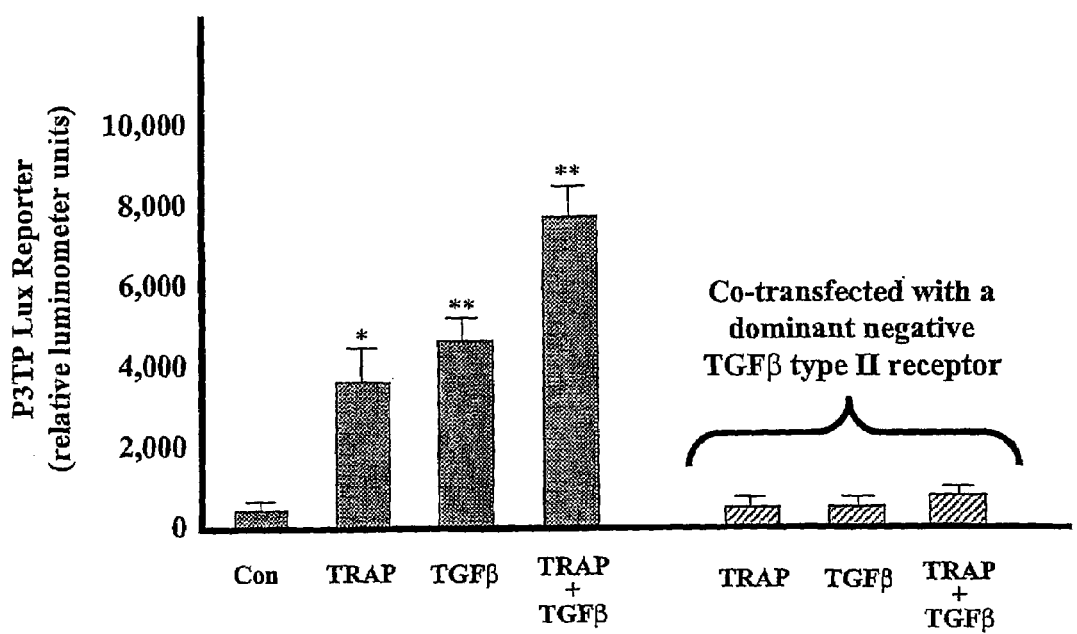

The data in FIG. 17 show that both TGFβ and TRAP can strongly upregulate a reporter gene (P3TP-Lux) that is sensitive to the TGFβ regulatory Smads 2 and 3. The effects of TGFβ and TRAP are additive. As TRIP-1 is known to interact with the type II TGFβ receptor we investigated whether TRAP activation of this pathway could be blocked in the presence of a dominant negative type II TGFβ receptor expression vector. FIG. 17 also demonstrates that in cells that have been co-transfected with a dominant negative type II TGFβ receptor we can block both TGFβ and TRAP activation of the pathway. These results were obtained with both osteoblast cell lines, MG-63 and SaOS2. The data with the MG-63 cell is what is shown.

Figure 18:
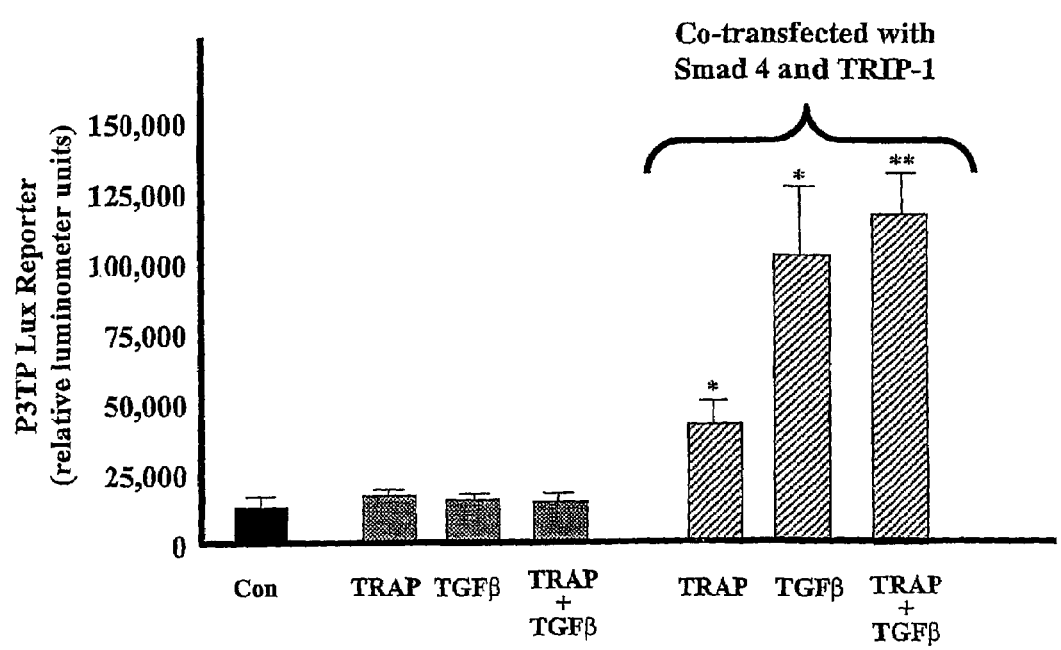

When these experiments were repeated in a Smad4 deficient cell type (SW408 cells), neither TGFβ nor TRAP could activate the reporter gene (FIG. 18). As Smad 4 is a requisite co-factor for Smad 2 and 3 signaling, these results are consistent with TRAP working through the Smad pathway. Restoration of Smad4 and TRIP-1 protein in these cells, restores TGFβ and TRAP signaling (FIG. 18). Thus, all of these pieces of evidence point to the activation of the TGFβ/Smad pathway through the association of TRAP with TRIP-1.

Figure 19:
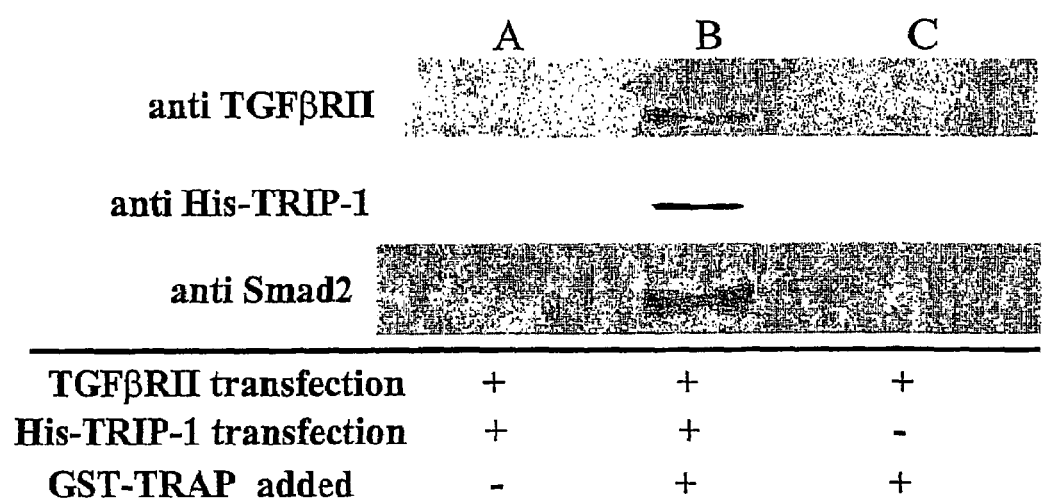

TRIP-1 interacted with the type II TGFβ receptor (TGFβRII) when TRAP is present in the cytosol. These data are presented in FIG. 19. These experiments utilized a "HIS" tagged TRIP-1 (HIS-TRIP) and a "GST" tagged TRAP (GST-TRAP). Detection of HIS-TRIP was performed with anti-HIS antibodies and detection of the TGFβRII and Smad 2 were performed with a commercially available antibodies. For these studies, all cells were transfected with the TGFβRII. In the first experiment these cells were co-transfected with HIS-TRIP for 18 hours and then exposed them to exogenously added GST-TRAP for 12 hours. The cells were lysed and the lysate incubated with glutathione beads. The beads were extensively washed and the proteins interacting with the beads were analyzed with Western analysis. FIG. 19 demonstrates that if the cells are not exposed to GST-TRAP (column A) or they are not co-transfected with HIS-TRIP (column C) neither TRIP, TGFβRII nor Smad 2 can be detected. However, when both HIS-TRIP and GST-TRAP are present the complex of the TGFβRII, HIS-TRIP and Smad 2 can be extracted and detected (column B). These data provide evidence that in osteoblasts exogenously added TRAP can interact with cytosolic TRIP and that this complex associates with the type II TGFβ receptor and Smad 2.

As a final test for the ability of osteoblasts to differentiate within osteoclast lacunae containing TRAP, osteoblasts were cultured on cortical bovine bone wafers on which we had previously created resorption lacunae with authentic osteoclasts. The lacunae contain substantial amounts of TRAP. After 7-10 days of culture, only osteoblasts residing within the lacunae had differentiated to the point of producing histochemically detectable alkaline phosphatase (Osteoclast lacunae were created by culturing osteoclasts on cortical bone wafers in the presence of parathyroid hormone and vitamin D. The osteoclasts were removed by gentle scraping. The margin of the lacunae were visible. Osteoblasts were then cultured on these wafers for 10 days and alkaline phosphatase positive cells were identified with histochemical methods. Only the osteoblasts residing within the lacunae demonstrated high levels of alkaline phosphatase.). This model effectively recapitulates the bone remodeling process in vitro and verifies that osteoblasts can express a more differentiated phenotype when exposed to molecules within osteoclast lacunae.

4. Example 4

Tartrate-Resistant Acid Phosphatase Can Induce Apoptosis in Mature Osteoblasts a) Abstract Tartrate-resistant acid phosphatase (TRAP) is an acid hydrolase found at high concentrations in osteoclasts. TRAP can be recognized by osteoblast-specific genes and that it is one of the anchoring molecules by which osteoblasts attach to resorption lacunae. TRAP also can induce osteoprogenitor differentiation. In this present paper we describe yet another function for the enzyme. We show data that indicate that TRAP can induce apoptosis in aging or scenescent osteoblasts. Morphological evidence, DNA fragmentation, biochemical assays for caspases and their substrates and a possible mechanisitic pathway are all consistent with the conclusion that TRAP can cause cell death and disintegration.

Osteoclast resorption can only occur on a cell-free mineral surface and osteoclast TRAP can be one mechanism by which a the surface may be cleaned of lining cells.

b) Materials and Method (1) Cytochemical Staining for Scenescence-Activated β-galactosidase Cells were washed in PBS, fixed for 3-5 min (room temperature) in 2% formaldehyde:0.2% glutaraldehyde. The cells were incubated at 37oC with fresh β-galactosidase stain solution (1 mg of 5-bromo-4-chloro-3-indolyl b-D-galactoside per ml, 40 mM citric acid:sodium phosphate, pH 6.0, 5 mM potas-sium ferrocyanide, 5 mM potassium ferricyanide, 150 mM NaCl, and 2 mM MgCl2). Staining was evident in 24 h and was maximal in 12-16 h.

(2) In Vitro Cell Senescence

Rat primary calvaria cells were serially passaged by trypsinisation at a split ratio of 1:2 or 1:4 once they reached confluence. At each subculturing, the number of cells was counted using a Coulter counter (Coulter Electronics, UK) and the number of population doublings (PDs) was calculated as log N/log 2, where N is the number of cells in a confluent layer divided by the initial number of cells seeded. Subculturing continued until the cells reached the end of their lifespan, which was evident when they failed to become confluent within four weeks of culturing. The osteoblastic cells were studied at different time points covering their entire lifespan, and we refer to cells with less than 50% lifespan completed as early-passage young cells, cells between 60% and 70% lifespan completed are considered to be intermediate-passage middle-aged cells, and cells with more than 90% lifespan completed are considered late-passage senescent cells.

(3) Assays for Apoptosis (a) DNA Fragmentation Assay

After the cultivation of cells in the presence of 5 ug/ml of purified TRAP for 36 hrs, cells ($5\times10^5$) were lysed in a buffer containing 0.5% Triton X-100, 10 mM Tris, pH 7.4,and 10 mM EDTA. After treatment with RNase A and proteinase K, the size of DNA was analyzed by 1.2% agarose gel electrophoresis.

(b) TUNEL Assay

Osteoblastic cells were seeded on chamber slides at a density of $1\times10^3$ cells per slide and cultured for 24 hours in the presence of TRAP or cells treated with Etoposide (Sigma, St Louis, Mich.) for 10 min followed by 24 h growth was used as positive controls. Apoptosis-induced DNA strand breaks were detected using the TUNEL (terminal deoxynucleotidyl transferase-mediated dUTP nick end labeling) technique (Promega, Madsion, Wis.) as described by the manufacturer and analyzed under a microscope.

(4) RNA Preparation and Quantitative Real-Time Polymerase Chain Reaction (RT-PCR)

Confluent ROS 17/2.8, MC3T3-E1, and primary rat calvaria osteoblastic cultures were grown in standard culture medium. For RNA isolation, cells were trypsinized, collected in PBS solution and total RNA was extracted by a RNAeasy Mini Kits (Qiagen, Valencia Calif. USA).

cDNA was synthesized from 1 ug of total RNA in a 10-uL reaction mixture containing 1 unit reverse transcriptase buffer (5 u=50 mM $MgCl_2$, 250 mM KCl, 250 mM Tris-HCl (pH 8.3), 50 mM dithiothreitol (DTT), 2.5 mM spermidine), dCTP, dGTP, dATP, and dTTP each at 2 mM, 20 U of RNase inhibitor, 8-10 U of Superscript II reverse transcriptase 50 pmol of poly-$dT_{15}$ primer (all from Invitrogen, Carlsbad, Calif.). Reaction times were at least 1 h at 42° C. After the reverse transcription all the samples were diluted 1:8 with sterile water and 4 µl of these dilutions were used for each SYBR.

(5) SYBER Green Real Time PCR Assay

Each SYBR Green reaction (20 ul total volume) contained 1 ul of diluted cDNA as template. The final concentration of the reagents were: 1 uM SYBR Green Reaction Buffer, 3 mM MgCl, 1 mM dATP, 1 mM dUTP, 1 mM dCTP, 1 mM dGTP, 0.3 uM of each primer, 0.01 U/ml UNG-Enzyme and 0.025 U/ml Taq Gold DNA Polymerase (SYBR Green PCR Core Reagents, PE Biosystems). For all the primer sets, two PCR reactions were carried out with our standard SYBR Green protocol with cDNA as template.

The reactions were incubated at 50° C. for 2 min to activate the uracil N-glycosylase (UNG) and then for 5 min at 95° C. to inactivate this enzyme and activate the Amplitaq Gold polymerase followed by 45 cycles at 95° C. for 15 sec (denaturation) and at 45° C. for 20 seconds (annealing) and 75° C. for 10 seconds (extension and detection).

c) Results

ROS 17/2.8 cells are a transformed cell line demonstrating many features of mature, end stage osteoblasts. Their gene expression profile matches the phenotype associated with a fully differentiated bone forming cell. ROS 17/2.8 cells, when exposed, to the osteoclast type V TRAP undergo apoptosis. Moreover, when the cells are stained for alkaline phosphatase, the normally highly expressing control cells shed their alkaline phosphatase and take on a crenated appearance. The TRAP has no phosphatase activity at the pH tested (7.4) and control phosphatases (ATPase and myokinase) do not show the same effect.

Figure 20:
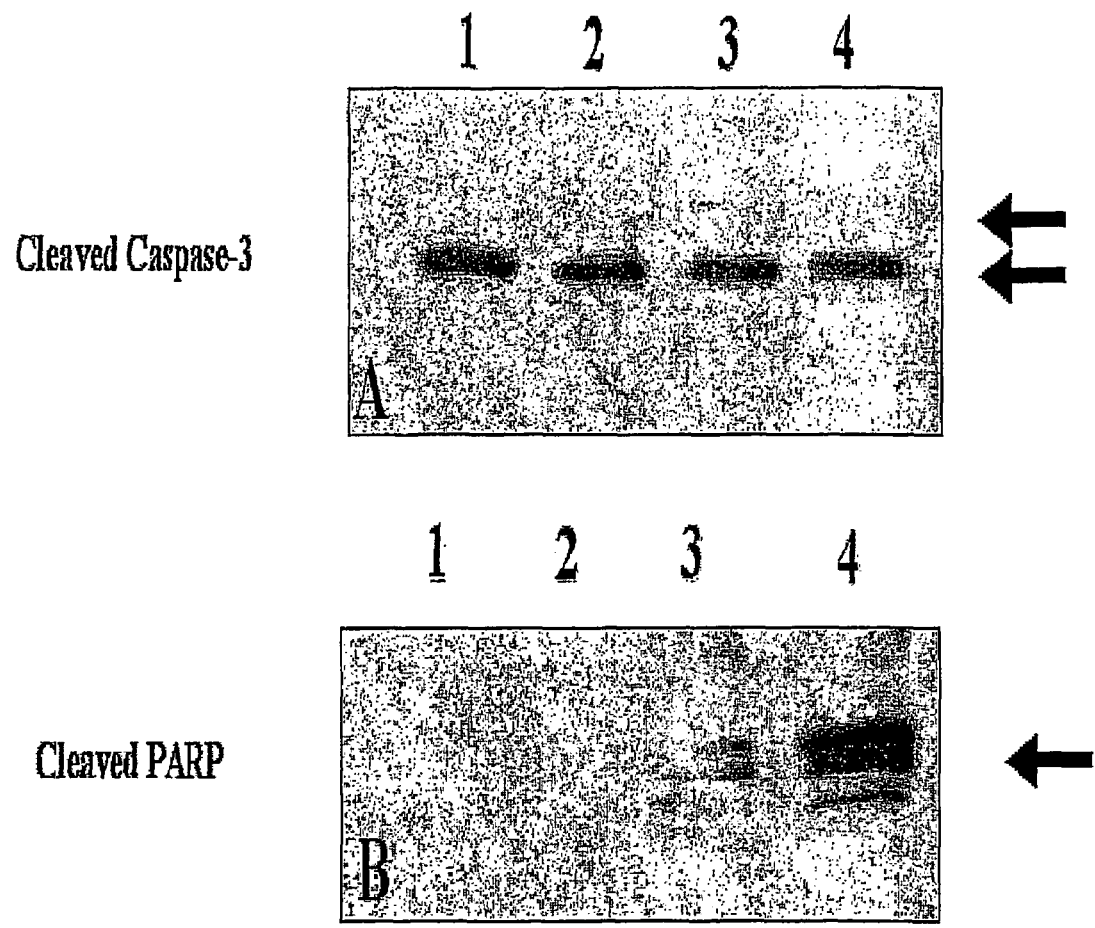

DNA laddering, another hallmark of apoptosis, also occurs in the ROS17/2.8 cell line after exposure to TRAP. FIG. 20 demonstrates a dose-dependent and time dependent effect of TRAP on DNA. FIG. 20A shows that after 36 hours a concentration of 5 µg/ml TRAP will induce laddering resulting in fragmentation of the DNA into 180-200 base pair nucleotides. FIG. 20B shows that the laddering will occur at lower concentrations (i.e. 0.5 and 1.0 µg/ml) if the cells are exposed to the TRAP for 60 hours.

Figure 21:
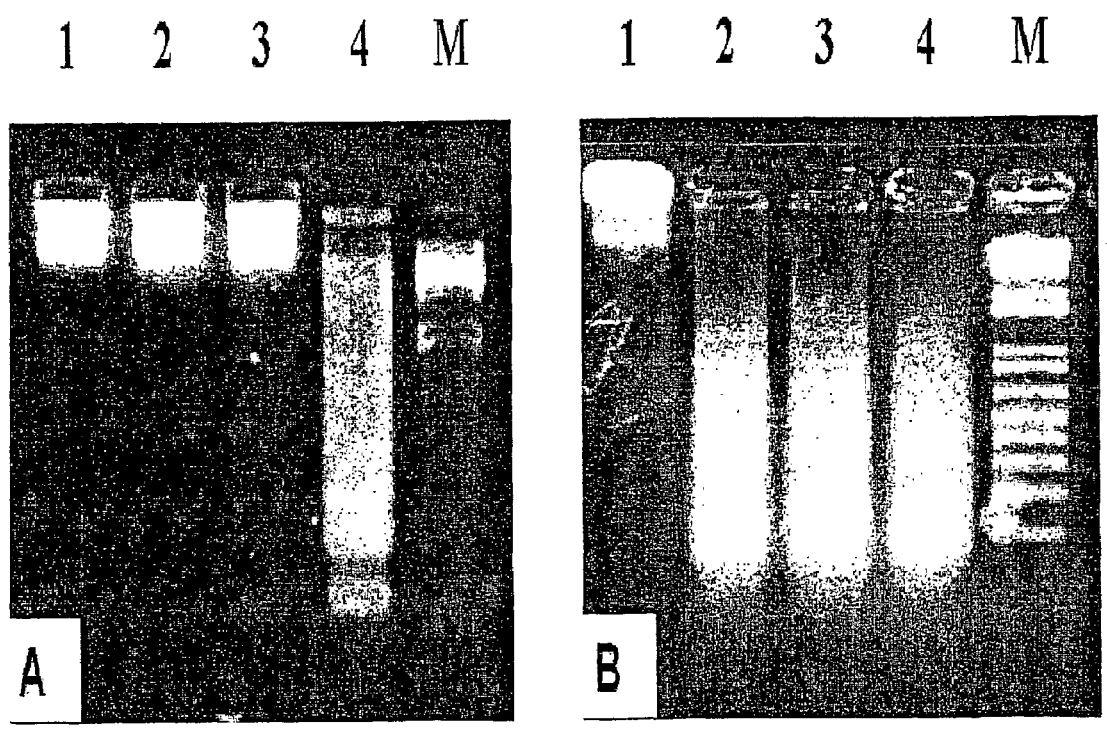
Figure 21C:
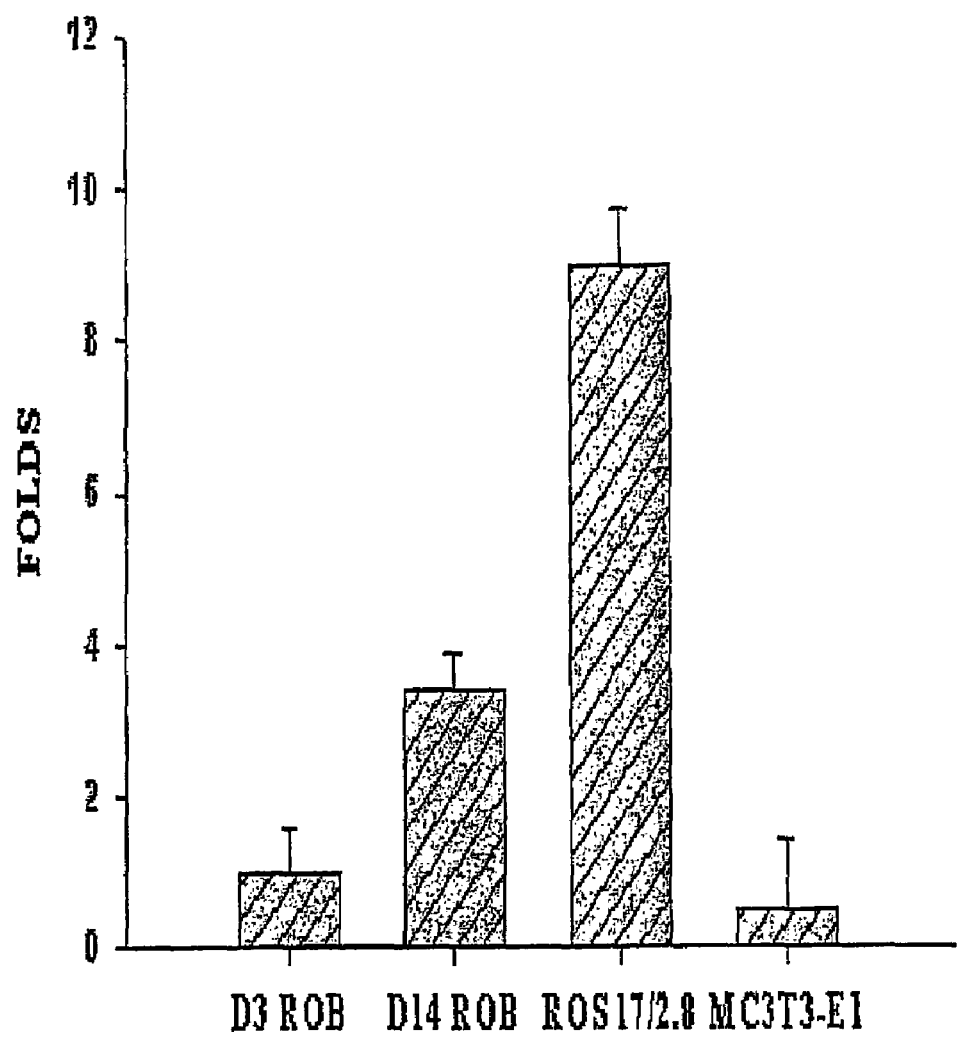
Figure 22:
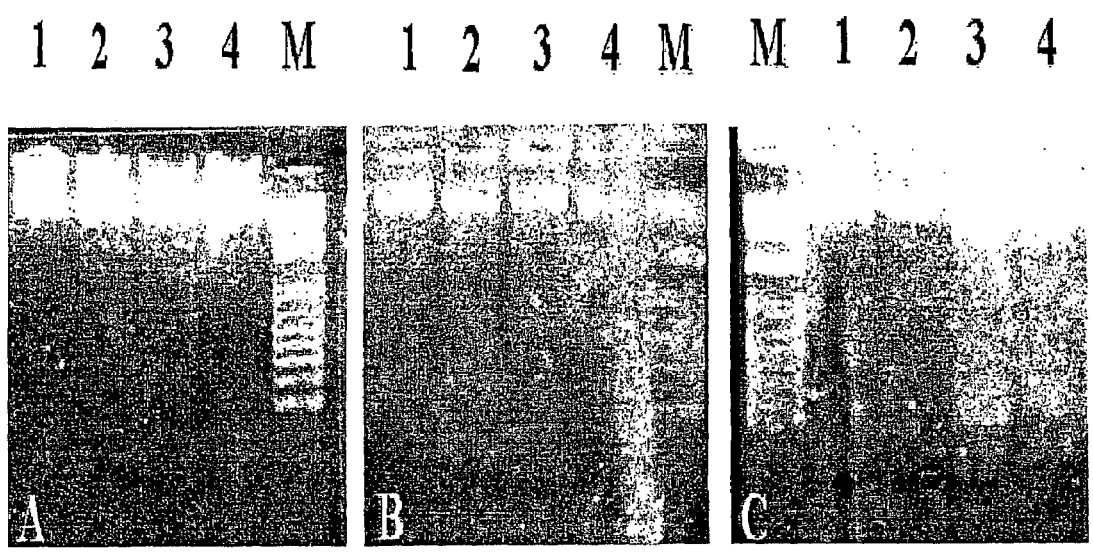

This induction of apoptosis does not occur in an undifferentiated population of osteoblasts. Cells freshly prepared from neo natal rat calvaria as well as the relatively immature MC3T3 osteoblasts are not affected by TRAP. However, freshly isolated osteoblasts that have been cultured for 14 days under differentiating conditions behave similarly to the ROS 17/2.8 cells. For these experiments the stage of maturation of the osteoblast cell lines was determined by measuring collagenase III levels and levels of the senescence-associated b-galactosidase enzyme (FIGS. 21A and B). Collagenase III (MP-13) is marker for late stage osteoblast differentiation. It is induced by hormones and factors that enhance osteoblast development. FIG. 21A shows that early passage rat osteoblasts (day 3) (D3 ROB) and MC3T3-E1 cells have very low levels of collagenase III. This level increases as the rat osteoblasts mature (day 14) (D14 ROB) and reaches a maximum in ROS 17/2.8 cells (FIG. 21C). FIG. 21B demonstrates an increase in the senescence-associated β-galactosidase in day 14 osteoblasts, with and without the addition of the differentiating agent β-glycerol phosphate. Examination of apoptotic DNA fragmentation in these cells is shown in FIG. 22. In these data, FIG. 22A (MC3T3-E1 cells) and FIG. 22B (D3 ROB) are representative of osteoblasts at an immature stage. There is no evidence of DNA fragmentation after exposure to TRAP at any concentration in these cells. However, rat calvarial osteoblasts that have been passaged and cultured for 14 days demonstrate DNA fragmentation after exposure to TRAP at concentrations of 1.0 and 5.0 ug/ml (FIG. 22C).

Verification of apoptosis in day 14 calvarial cells and ROS 17/2.8 cells was obtained with TUNEL staining. Both scenescent osteoblasts and ROS17/2.8 cells are virtually 100% positive for TUNEL staining after a 24 hour exposure to TRAP at 5.0 ug/ml. Etoposide, a potent non-cell-specific inducer of apoptosis, was used a positive control and demonstrated an effect that was very similar to the TRAP. Untreated rat calvarial cells and ROS 17/2.8 cells showed no indication of apoptosis by TUNEL staining.

Biochemical confirmation of the effect of TRAP on osteoblast apoptosis was obtained by assaying levels of caspase-3 and poly ADP-ribose polymerase (PARP) in these cells lines. Caspase-3 is an enzyme that is a key member of the apoptotic cascade. However, most cells have a constitutive amount of this enzyme. It is not until the caspase(s) are cleaved that they become activated. Thus, another indicator of a cells progression through apoptosis is a measurement of its cleaved caspase 3 levels. Similarly, poly ADP-ribose polymerase is a substrate for active caspase 3 and increased levels of cleave PARP are indicative of an active caspase.

Figure 23:
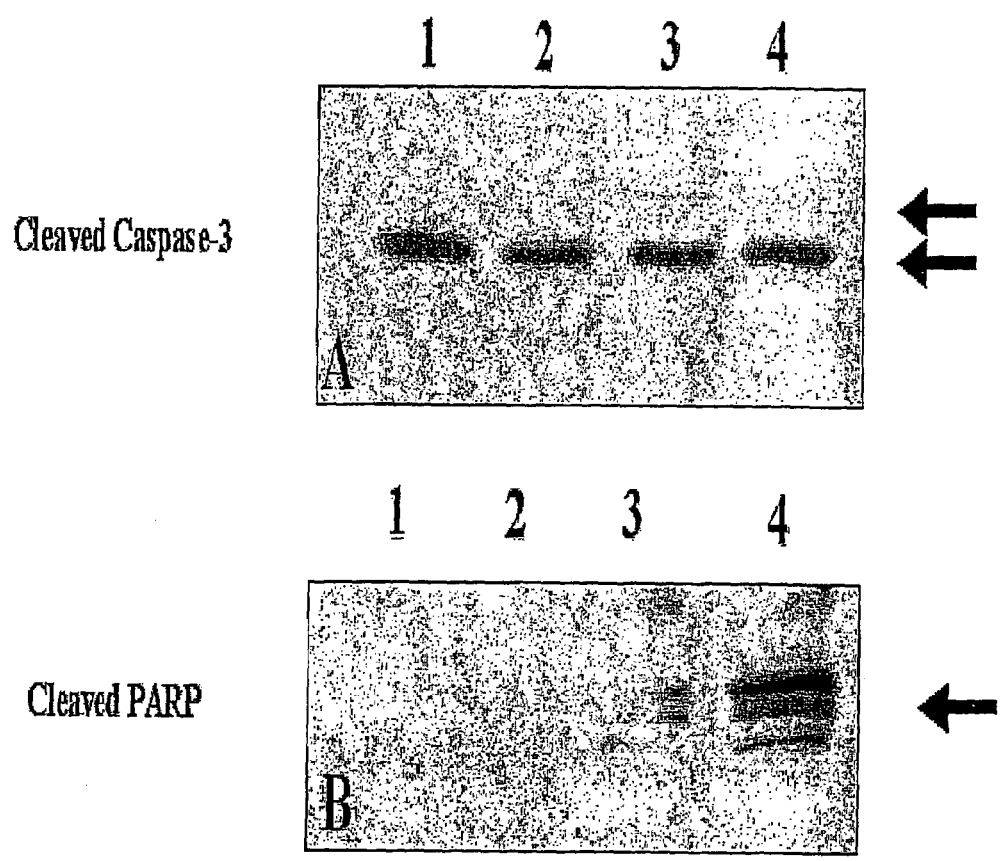
FIG. 23 shows that TRAP induces an increase in both cleaved caspase 3 and cleaved PARP in ROS 17/2.8 cells.
Figure 24:
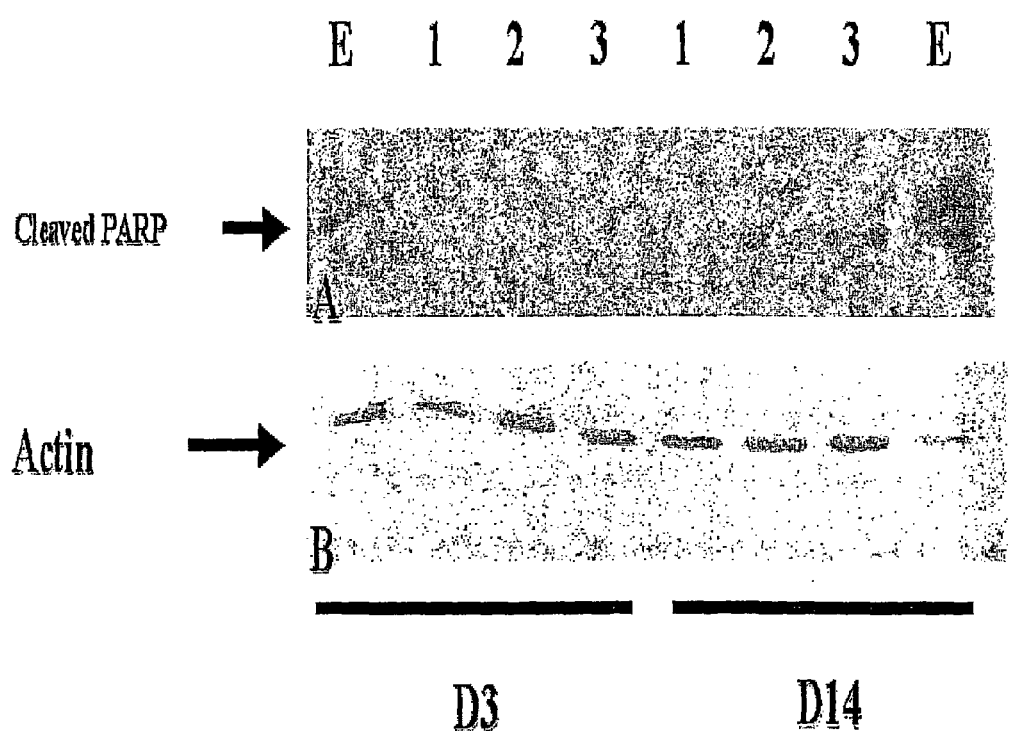
FIG. 24 shows the effect of TRAP on cleavage of PARP by day 14 cells but not day 3 cells.
Figure 25:
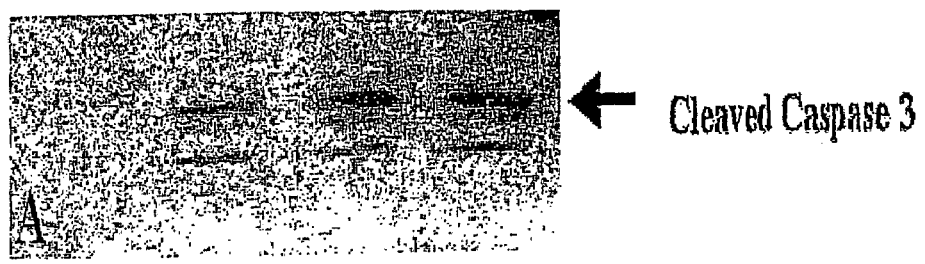
Figure 25:
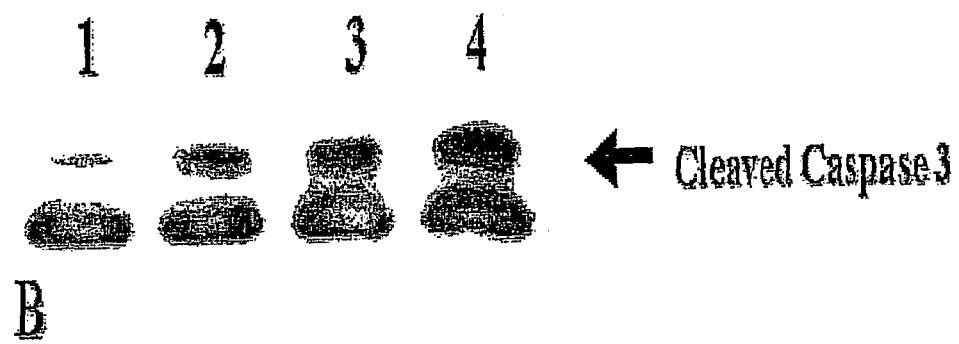
Figure 25:
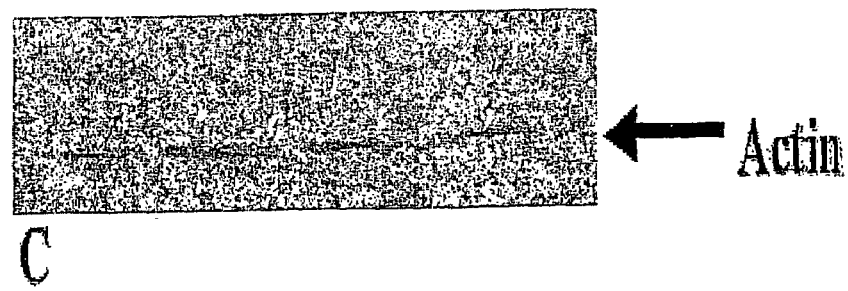

In FIG. 23 TRAP induces an increase in both cleaved caspase 3 and cleaved PARP in ROS 17/2.8 cells. This occurs after a 36 hour exposure at concentrations of 1.0 and 5.0 ug/ml TRAP. FIGS. 24 and 25 demonstrate that this same effect occurs only in rat calvarial osteoblasts after 14 days of culture and not in osteoblasts at 3 days of culture. FIG. 24 shows the effect of TRAP on cleavage of PARP by day 14 cells but not day 3 cells and FIG. 25 shows cleavage of caspase 3 in day 14 cells treated with TRAP. Also in FIG. 25, it was shown that both a purified preparation of TRAP as well as a recombinant fusion protein of GST and TRAP (GST-TRAP) have the same effect on the cells. Usually the regular peptide hormone $EC_{50}$ (TGF-b, BMP, PtHrP ) is around umol/L. The maximal dose of TRAP protein used in this paper is also around nmole/L range.

Having confirmed that the TRAP protein was responsible for cell death of osteoblasts at the late stage of differentiation, differences in phenotype between D3 and D14 primary osteoblasts may protect immature osteoblasts from TRAP-induced apoptosis were investigated. Because osteoprotegrin (OPG) is a known marker for osteoblasts, ELISA assays were performed to determine whether the two primary osteoblast cells produced different levels of OPG (FIG. 26). We found that the level of OPG in the D14 osteoblasts was the same as that in the D3 osteoblasts prior to exposure to TRAP. However, following TRAP treatment, the level of OPG increased in the D3 osteoblasts in a dose-dependent manner but decreased in the D14 osteoblasts.

(1) TRAP Apoptotic Signaling

There are two branches that are important in TGFβ signaling, the Smad pathway and the MAP kinase pathway. As disclosed herein, TRAP is stimulatory for osteoprogenitor cells differentiation through the Smad pathway and addition of TRAP to these cells did not cause apoptosis. However, addition of TRAP to aged osteoblasts induces apoptosis through the MAP kinase pathway. Transfection of ROS17/2.8 cells with either a dominant negative Ras or a dominant negative Raf, both of which are intermediates in the TGFb/MAP kinase pathway, blocked the apoptotic effect of TRAP. It was demonstrated that the induction of apoptosis by TRAP in control cells. It was also shown that blockade of Ras signaling prevents apoptosis. The same is true with a blockade of Raf signaling and was shown. These data indicate the MAP kinase branch of the TGFβ pathway in mediating the effect of TRAP on aged osteoblasts.

F. Sequences

| 1. SEQ ID NOS: 1–36 table 4. |
| --- |
| a) SEQ ID NO: 37 GPC4 nucleic acid genbank accession number XM_029542 start codon at coding 118–1788 |

```
   1 ccttctccct ccagctccac tcgctagtcc ccgactccgc cagccctcgg cccgctgccg
  61 tagcgccgct tcccgtccgg tcccaaaggt gggaacgcgt ccgccccggc ccgcaccatg
 121 gcacggttcg gcttgcccgc gcttctctgc accctggcag tgctcagcgc cgcgctgctg
 181 gctgccgagc tcaagtcgaa aagttgctcg gaagtgcgac gtctttacgt gtccaaaggc
 241 ttcaacaaga acgatgcccc cctccacgag atcaacggtg atcatttgaa gatctgtccc
 301 cagggttcta cctgctgctc tcaagagatg gaggagaagt acagcctgca agtaaagat
 361 gatttcaaaa gtgtggtcag cgaacagtgc aatcatttgc aagctgtctt tgcttcacgt
 421 tacaagaagt ttgatgaatt cttcaaagaa ctacttgaaa atgcagagaa atccctgaat
 481 gatatgtttg tgaagacata tggccattta tacatgcaaa attctgagct atttaaagat
 541 ctcttcgtag agttgaaacg ttactacgtg gtgggaaatg tgaacctgga agaaatgcta
 601 aatgacttct gggctcgcct cctggagcgg atgttccgcc tggtgaactc ccagtaccac
 661 tttacagatg agtatctgga atgtgtgagc aagtatacgg agcagctgaa gcccttcgga
 721 gatgtccctc gcaaattgaa gctccaggtt actcgtgctt tgtagcagc ccgtactttc
 781 gctcaaggct tagcggttgc gggagatgtc gtgagcaagg tctccgtggt aaaccccaca
 841 gcccagtgta cccatgccct gttgaagatg atctactgct cccactgccg gggtctcgtg
 901 actgtgaagc catgttacaa ctactgctca aacatcatga gagctgtttt ggccaaccaa
 961 ggggatctcg attttgaatg gaacaatttc atagatgcta tgctgatggt ggcagagagg
1021 ctagagggtc ctttcaacat tgaatcggtc atggatccca tcgatgtgaa gatttctgat
1081 gctattatga acatgcagga taatagtgtt caagtgtctc agaaggtttt ccagggatgt
1141 ggaccccca agcccctccc agctggacga atttctcgtt ccatctctga aagtgccttc
1201 agtgctcgct tcagaccaca tcaccccgag gaacgcccaa ccacagcagc tggcactagt
1261 ttggaccgac tggttactga tgtcaaggag aaactgaaac aggccaagaa attctggtcc
1321 tcccttccga gcaacgtttg caacgatgag aggatggctg caggaaacgg caatgaggat
1381 gactgttgga atgggaaagg caaaagcagg tacctgtttg cagtgacagg aaatggatta
1441 gccaaccagg gcaacaaccc agaggtccag gttgacacca gcaaaccaga catactgatc
1501 cttcgtcaaa tcatggctct tcgagtgatg accagcaaga tgaagaatgc atacaatggg
1561 aacgacgtgg acttctttga tatcagtgat gaaagtagtg gagaaggaag tggaagtggc
1621 tgtgagtatc agcagtgccc ttcagagttt gactacaatg ccactgacca tgctgggaag
1681 agtgccaatg agaaagccga cagtgctggt gtccgtcctg ggcacaggc ctacctcctc
1741 actgtcttct gcatcttgtt cctggttatg cagagagagt ggagataatt ctcaaactct
1801 gagaaaaagt gttcatcaaa aagttaaaag gcaccagtta tcactttct accatcctag
1861 tgactttgct ttttaaatga atggacaaca atgtacagtt tttactatgt ggccactggt
1921 ttaagaa
```

-continued

| 1. SEQ ID NOS: 1–36 table 4. |
|---|
| b) SEQ ID NO: 38 GPC4 peptide genbank accession number XM_029542 |

MARFGLPALLCTLAVLSAALLAAELKSKSCSEVRRLYVSKGFNK

NDAPLHEINGDHLKICPQGSTCCSQEMEEKYSLQSKDDFKSVVSEQCNHLQAVFASRY

KKFDEFFKELLENAEKSLNDMFVKTYGHLYMQNSELFKDLFVELKRYYVVGNVNLEEM

LNDFWARLLERMFRLVNSQYHFTDEYLECVSKYTEQLKPFGDVPRKLKLQVTRAFVAA

RTFAQGLAVAGDVVSKVSVVNPTAQCTHALLKMIYCSHCRGLVTVKPCYNYCSNIMRG

CLANQGDLDFEWNNFIDAMLMVAERLEGPFNIESVMDPIDVKISDAIMNMQDNSVQVS

QKVFQGCGPPKPLPAGRISRSISESAFSARFRPHHPEERPTTAAGTSLDRLVTDVKEK

LKQAKKFWSSLPSNVCNDERMAAGNGNEDDCWNGKGKSRYLFAVTGNGLANQGNNPEV

QVDTSKPDILILRQIMALRVMTSKMKNAYNGNDVDFFDISDESSGEGSGSGCEYQQCP

SEFDYNATDHAGKSANEKADSAGVPRGAQAYLLTVFCILFLVMQREWR

| c) SEQ ID NO: 39 TRIP nucleic acid genbank accession number U36764 |
|---|

```
   1 ggcacgaggt tgcggccttc ctcgcgtcac cgccgggatg aagccgatcc
  51 tactgcaggg ccatgagcgg tccattacgc agattaagta taaccgcgaa
 101 ggagacctcc tctttactgt ggccaaggac cctatcgtca atgtatggta
 151 ctctgtgaat ggtgagaggc tgggcaccta catgggccat accggagctg
 201 tgtggtgtgt ggacgctgac tgggacacca agcatgtcct cactggctca
 251 gctgacaaca gctgtcgtct ctgggactgt gaaacaggaa agcagctggc
 301 ccttctcaag accaattcgg ctgtccggac ctgcggtttt gactttgggg
 351 gcaacatcat catgttctcc acggacaagc agatgggcta ccagtgcttt
 401 gtgagctttt ttgacctgcg ggatccgagc cagattgaca caatgagcc
 451 ctacatgaag atcccttgca atgactctaa aatcaccagt gctgtttggg
 501 gaccctggg ggagtgcatc atcgctggcc atgagagtgg agagctcaac
 551 cagtatagtg ccaagtctgg agaggtgttg gtgaatgtta aggagcactc
 601 ccggcagatc aacgacatcc agttatccag ggacatgacc atgtttgtga
 651 ccgcgtccaa ggacaacaca gccaagcttt tgactccac aactcttgaa
 701 catcagaaga ctttccggac agaacgtcct gtcaactcag ctgccctctc
 751 ccccaactat gaccatgtgg tcctgggcgg tggtcaggaa gccatggatg
 801 taaccacaac ctccaccagg attggcaagt ttgaggccag gttcttccat
 851 ttggcctttg aagaagagtt tggaagagtc aagggtcact ttggacctat
 901 caacagtgtt gccttccatc ctgatggcaa gagctacagc agcggcggcg
 951 aagatggtta cgtccgtatc cattacttcg acccacagta cttcgaattt
1001 gagtttgagg cttaagaagc tggatctcct gccgggcgtg gtggctcatg
1051 cctgtaatcc caccactttt ttttaaggca ggcggatcac ctgaggtcag
1101 gagtttaaga ccagcctgac caacatggag aaactcgtct ctactaaaaa
1151 tacaaaaata caaaaattag ccaggcatgg tggcacacgc ctatagtccc
1201 agctactcag gaggctgagg caggagaatc acttgaaccc aggaggcata
```

-continued

1. SEQ ID NOS: 1–36 table 4.

```
1251 ggttgcagtg agctgagatc acgtcattgc actccatcct gagccacaag
1301 agcaaaactc cgtctcaaaa aaaaaaaa
``` d) SEQ ID NO: 40 TRIP peptide genbank accession number U36764

MKPILLQGHERSITQIKYNREGDLLFTVAKDPIVNVWYSVNGER

LGTYMGHTGAVWCVDADWDTKHVLTGSADNSCRLWDCETGKQLALLKTNSAVRTCGFD

FGGNIIMFSTDKQMGYQCFVSFFDLRDPSQIDNNEPYMKIPCNDSKITSAVWGPLGEC

IIAGHESGELNQYSAKSGEVLVNVKEHSRQINDIQLSRDMTMFVTASKDNTAKLFDST

TLEHQKTFRTERPVNSAALSPNYDHVVLGGGQEAMDVTTTSTRIGKFEARFFHLAFEE

EFGRVKGHFGPINSVAFHPDGKSYSSGGEDGYVRIHYFDPQYFEFEFEA e) SEQ ID NO: 41 TRAP nulceic acid XM_032796. Reading frame is 90–1067

```
   1 agggaataaa ggctcaggga ccggcagttc tactctagag cccaccagcc tctcagagcc
  61 tccggtgact ggcctgtgtc tccccctgga tggacatgtg gacggcgctg ctcatcctgc
 121 aagccttgtt gctaccctcc ctggctgatg gtgccacccc tgccctgcgc tttgtagccg
 181 tgggtgactg ggggaggggtc cccaatgccc cattccacac ggcccgggaa atggccaatg
 241 ccaaggagat cgctcggact gtgcagatcc tgggtgcaga cttcatcctg tctctagggg
 301 acaatttta cttcactggt gtgcaagaca tcaatgacaa gaggttccag agacctttg
 361 aggacgtatt ctctgaccgc tcccttcgca agtgccctg gtacgtgcta gccggaaacc
 421 atgaccacct tggcaatgtc tctgcccaga ttgcatactc taagatctcc aagcgctgga
 481 acttccccag cccctttctac cgcctgcact tcaagatccc acagaccaat gtgtctgtgg
 541 ccattttat gctggacaca gtgacactat gtggcaactc agatgacttc ctcagccagc
 601 agcctgagag gcccccgagac gtgaagctgg cccgcacaca gctgtcctgg ctcaagaaac
 661 agctggcggc ggccagggag gactacgtgc tggtggctgg ccactacccc gtgtggtcca
 721 tagccgagca cgggcctacc cactgcctgg tcaagcagct acgccactg ctggccacat
 781 acggggtcac tgcctacctg tgcggccacg atcacaatct gcagtacctg caagatgaga
 841 atggcgtggg ctacgtgctg agtggggctg ggaatttcat ggaccccctca aagcggcacc
 901 agcgcaaggt ccccaacggc tatctgcgct tccactatgg gactgaagac tcactgggtg
 961 gctttgccta tgtggagatc agctccaaag agatgactgt cacttacatc gaggcctcgg
1021 gcaagtccct ctttaagacc aggctgccga ggcgagccag gccctgaact cccatgactg
1081 cccagctctg aggcccgatc tccactgttg ggtgggtggg ccctgccggg accctgctca
1141 caggcaggct tttcctccaa cctgtggcgc tgcagcaggg caggaagggg aaacacagct
1201 gatgaactgt ggtgccacat gacccttgtg gcacagatgc ccacgtatgt gaaacacaca
1261 tggacatgtg tcccagccac agtgttatgc tctgtggctg gctcaccttt gctgagttcc
1321 ggggtgcaat gggggaggga gggagggaaa gcttcctcct aaatcaagca tctttctgtt
1381 actgatgttc aataaaagaa tagttgccaa ggctg
``` f) SEQ ID NO: 42 TRAP peptide

MDMWTALLILQALLLPSLADGATPALRFVAVGDWGGVPNAPFHT

AREMANAKEIARTVQILGADFILSLGDNFYFTGVQDINDKRFQETFEDVFSDRSLRKV

PWYVLAGNHDHLGNVSAQIAYSKISKRWNFPSPFYRLHFKIPQTNVSVAIFMLDTVTL

-continued

1. SEQ ID NOS: 1–36 table 4.

CGNSDDFLSQQPERPRDVKLARTQLSWLKKQLAAAREDYVLVAGHYPVWSIAEHGPTH

CLVKQLRPLLATYGVTAYLCGHDHNLQYLQDENGVGYVLSGAGNFMDPSKRHQRRVPN

GYLRFHYGTEDSLGGFAYVEISSKEMTVTYIEASGKSLFKTRLPRRARP g) SEQ ID NO: 43 Degenerate of nucleic acid encoding SEQ ID NO: 23 G at position 3 to A

5'-ACACCGCTTTCGTATCTGAAGGGTCTGGTGACGGTG-3' h) SEQ ID NO: 44 Conservative substitution in SEQ ID NO: 23

TPLSYLKGLVTI i) SEQ ID NO: 45 degenerate nucleic acid encoding SEQ ID NO: 44

5'-ACACCGCTTTCGTATCTGAAGGGTCTGGTGACGATA-3' j) SEQ ID NO: 46 degenerate nucleic acid encoding SEQ ID NO: 44

5'-ACTCCGCTTTCGTATCTCTAAGGGTCTGGTGACGATA-3' k) SEQ ID NO: 47 degenerate nucleic acid encoding SEQ ID NO: 38

Atg gcacggttcg gattgcccgc gcttctctgc accctggcag tgctcagcgc cgcgctgctg
gctgccgagc tcaagtcgaa aagttgctcg gaagtgcgac gtctttacgt gtccaaaggc
ttcaacaaga acgatgcccc cctccacgag atcaacggtg atcatttgaa gatctgtccc
cagggttcta cctgctgctc tcaagagatg gaggagaagt acagcctgca agtaaagat
gatttcaaaa gtgtggtcag cgaacagtgc aatcatttgc aagctgtctt tgcttcacgt
tacaagaagt ttgatgaatt cttcaaagaa ctacttgaaa atgcagagaa atccctgaat
gatatgtttg tgaagacata tggccattta tacatgcaaa attctgagct atttaaagat
ctcttcgtag agttgaaacg ttactacgtg gtgggaaatg tgaacctgga agaaatgcta
aatgacttct gggctcgcct cctggagcgg atgttccgcc tggtgaactc ccagtaccac
tttacagatg agtatctgga atgtgtgagc aagtatacgg agcagctgaa gcccttcgga
gatgtccctc gcaaattgaa gctccaggtt actcgtgctt ttgtagcagc ccgtactttc
gctcaaggct agcggttgc gggagatgtc gtgagcaagg tctccgtggt aaaccccaca
gcccagtgta cccatgccct gttgaagatg atctactgct cccactgccg gggtctcgtg
actgtgaagc catgttacaa ctactgctca acatcatga gaggctgttt ggccaaccaa
ggggatctcg attttgaatg gaacaatttc atagatgcta tgctgatggt ggcagagagg
ctagagggtc ctttcaacat tgaatcggtc atggatccca tcgatgtgaa gatttctgat
gctattatga acatgcagga taatagtgtt caagtgtctc agaaggtttt ccagggatgt
ggacccccca agccctccc agctggatga atttctcgtt ccatctctga agtgccttc
agtgctcgct tcagaccaca tcaccccgag gaacgcccaa ccacagcagc tggcactagt
ttggaccgac tggttactga tgtcaaggag aaactgaaac aggccaagaa attctggtcc
tcccttccga gcaacgtttg caacgatgag aggatggctg caggaaacgg caatgaggat
gactgttgga atgggaaagg caaaagcagg tacctgtttg cagtgacagg aaatggatta
gccaaccagg gcaacaaccc agaggtccga gttgacacca gcaaaccaga catactgatc
cttcgtcaaa tcatggctct tcgagtgatg accagcaaga tgaagaatgc atacaatggg -continued

1. SEQ ID NOS: 1-36 table 4.

aacgacgtgg acttctttga tatcagtgat gaaagtagtg gagaaggaag tggaagtggc tgtgagtatc agcagtgccc ttcagagttt gactacaatg ccactgacca tgctgggaag agtgccaatg agaaagccga cagtgctggt gtccgtcctg gggcacaggc ctacctcctc actgtcttct gcatcttgtt cctggttatg cagagagagt ggagataa l) SEQ ID NO: 48 Conservative substitution in SEQ ID NO: 38 position 5, G to A substitution

MARFALPALLCTLAVLSAALLAAELKSKSCSEVRRLYVSKGFNK

NDAPLHEINGDHLKICPQGSTCCSQEMEEKYSLQSKDDFKSVVSEQCNHLQAVFASRY

KKFDEFFKELLENAEKSLNDMFVKTYGHLYMQNSELFKDLFVELKRYYVVGNVNLEEM

LNDFWARLLERMFRLVNSQYHFTDEYLECVSKYTEQLKPFGDVPRKLKLQVTRAFVAA

RTFAQGLAVAGDVVSKVSVVNPTAQCTHALLKMIYCSHCRGLVTVKPCYNYCSNIMRG

CLANQGDLDFEWNNFIDAMLMYAERLEGPFNIESVMDPIDVKISDAIMNMQDNSVQVS

QKVFQGCGPPKPLPAGRISRSISESAFSARFRPHHPEERPTTAAGTSLDRLVTDVKEK

LKQAKKFWSSLPSNVCNDERMAAGNGNEDDCWNGKGKSRYLFAVTGNGLANQGNNPEV

QVDTSKPDILILRQIMALRVMTSKMKNAYNGNDVDFFDISDESSGEGSGSGCEYQQCP

SEFDYNATDHAGKSANEKADSAGVRPGAQAYLLTVFCILFLVMQREWR m) SEQ ID NO: 49 degenerate nucleic acid encoding SEQ ID NO: 48 position 5 gcc.

Atg gcacggttcg ccttgcccgc gcttctctgc acctggcag tgctcagcgc cgcgctgctg gctgccgagc tcaagtcgaa agttgctcg gaagtgcgac gtctttacgt gtccaaaggc ttcaacaaga acgatgcccc cctccacgag atcaacggtg atcatttgaa gatctgtccc cagggttcta cctgctgctc tcaagagatg gaggagaagt acagcctgca agtaaagat gatttcaaaa gtgtggtcag cgaacagtgc aatcatttgc aagctgtctt tgcttcacgt tacaagaagt ttgatgaatt cttcaaagaa ctacttgaaa atgcagagaa atccctgaat gatatgtttg tgaagacata tggccattta tacatgcaaa attctgagct atttaaagat ctcttcgtag agttgaaacg ttactacgtg gtgggaaatg tgaacctgga agaaatgcta aatgacttct gggctcgcct cctggagcgg atgttccgcc tggtgaactc ccagtaccac tttacagatg agtatctgga atgtgtgagc aagtatacgg agcagctgaa gcccttcgga gatgtccctc gcaaattgaa gctccaggtt actcgtgctt ttgtagcagc ccgtactttc gctcaaggct tagcggttgc gggagatgtc gtgagcaagg tctccgtggt aaacccaca gcccagtgta cccatgccct gttgaagatg atctactgct cccactgccg gggtctcgtg actgtgaagc catgttacaa ctactgctca acatcatga gaggctgttt ggccaaccaa ggggatctcg attttgaatg gaacaatttc atagatgcta tgctgatggt ggcagagagg ctagagggtc ctttcaacat tgaatcggtc atggatccca tcgatgtgaa gatttctgat gctattatga acatgcagga taatagtgtt caagtgtctc agaaggtttt ccagggatgt ggaccccca gcccctccc agctggacga atttctcgtt ccatctctga agtgccttc agtgctcgct tcagaccaca tcaccccgag gaacgcccaa ccacagcagc tggcactagt ttggaccgac tggttactga tgtcaaggag aaactgaaac aggccaagaa attctggtcc tcccttccga gcaacgtttg caacgatgag aggatggctg caggaaacgg caatgaggat gactgttgga atgggaaagg caaaagcagg tacctgtttg cagtgacagg aaatggatta -continued

1. SEQ ID NOS: 1-36 table 4.

```
gccaaccagg gcaacaaccc agaggtccag gttgacacca gcaaaccaga catactgatc
cttcgtcaaa tcatggctct tcgagtgatg accagcaaga tgaagaatgc atacaatggg
aacgacgtgg acttctttga tatcagtgat gaaagtagtg gagaaggaag tggaagtggc
tgtgagtatc agcagtgccc ttcagagttt gactacaatg ccactgacca tgctgggaag
agtgccaatg agaaagccga cagtgctggt gtccgtcctg gggcacaggc ctacctcctc
actgtcttct gcatcttgtt cctggttatg cagagagagt ggagataa
``` n) SEQ ID NO: 50 degenerate nucleic acid encoding SEQ ID NO: 48 position 5 gca.

```
Atg gcacggttcg cattgcccgc gcttctctgc accctggcag tgctcagcgc cgcgctgctg
gctgccgagc tcaagtcgaa aagttgctcg gaagtgcgac gtctttacgt gtccaaaggc
ttcaacaaga acgatgcccc cctccacgag atcaacggtg atcatttgaa gatctgtccc
cagggttcta cctgctgctc tcaagagatg gaggagaagt acagcctgca agtaaagat
gatttcaaaa gtgtggtcag cgaacagtgc aatcatttgc aagctgtctt tgcttcacgt
tacaagaagt ttgatgaatt cttcaaagaa ctacttgaaa atgcagagaa atccctgaat
gatatgtttg tgaagacata tggccattta tacatgcaaa attctgagct atttaaagat
ctcttcgtag agttgaaacg ttactacgtg gtgggaaatg tgaacctgga agaaatgcta
aatgacttct gggctcgcct cctggagcgg atgttccgcc tggtgaactc ccagtaccac
tttacagatg agtatctgga atgtgtgagc aagtatacgg agcagctgaa gcccttcgga
gatgtccctc gcaaattgaa gctccaggtt actcgtgctt ttgtagcagc ccgtactttc
gctcaaggct tagcggttgc gggagatgtc gtgagcaagg tctccgtggt aaaccccaca
gcccagtgta cccatgccct gttgaagatg atctactgct cccactgccg gggtctcgtg
actgtgaagc catgttacaa ctactgctca acatcatga gaggctgttt ggccaaccaa
ggggatctcg attttgaatg gaacaatttc atagatgcta tgctgatggt ggcagagagg
ctagagggtc cttttcaacat tgaatcggtc atggatccca tcgatgtgaa gatttctgat
gctattatga acatgcagga taatagtgtt caagtgtctc agaaggtttt ccagggatgt
ggaccccca agccctccc agctggacga atttctcgtt ccatctctga aagtgccttc
agtgctcgct tcagaccaca tcaccccgag aacgcccaa ccacagcagc tggcactagt
ttggaccgac tggttactga tgtcaaggag aaactgaaac aggccaagaa attctggtcc
tcccttccga gcaacgtttg caacgatgag aggatggctg caggaaacgg caatgaggat
gactgttgga atgggaaagg caaaagcagg tacctgtttg cagtgacagg aaatggatta
gccaaccagg gcaacaaccc agaggtccag gttgacacca gcaaaccaga catactgatc
cttcgtcaaa tcatggctct tcgagtgatg accagcaaga tgaagaatgc atacaatggg
aacgacgtgg acttctttga tatcagtgat gaaagtagtg gagaaggaag tggaagtggc
tgtgagtatc agcagtgccc ttcagagttt gactacaatg ccactgacca tgctgggaag
agtgccaatg agaaagccga cagtgctggt gtccgtcctg gggcacaggc ctacctcctc
actgtcttct gcatcttgtt cctggttatg cagagagagt ggagataa
``` o) SEQ ID NO: 51-78, sequences related to linkers

PRFKIIGG,      SEQ ID NO: 51

PRFRIIGG,      SEQ ID NO: 52

-continued

| 1. SEQ ID NOS: 1–36 table 4. |
|---|

| | |
|---|---|
| SSRHRRALD, | SEQ ID NO: 53 |
| RKSSIIIRMRDVVL, | SEQ ID NO: 54 |
| SSSFDKGKYKKGDDA, | SEQ ID NO: 55 |
| SSSFDKGKYKRGDDA, | SEQ ID NO: 56 |
| IEGR, | SEQ ID NO: 57 |
| IDGR, | SEQ ID NO: 58 |
| GGSIDGR, | SEQ ID NO: 59 |
| PLGLWA, | SEQ ID NO: 60 |
| GPQGIAGQ, | SEQ ID NO: 61 |
| GPQGLLGA, | SEQ ID NO: 62 |
| GIAQQ, | SEQ ID NO: 63 |
| QPLGIAGI, | SEQ ID NO: 64 |
| GPEGLRVG, | SEQ ID NO: 65 |
| YGAGLGVV, | SEQ ID NO: 66 |
| AGLGVVER, | SEQ ID NO: 67 |
| AGLGISST, | SEQ ID NO: 68 |
| EPQALAMS, | SEQ ID NO: 69 |
| QALAMSAI, | SEQ ID NO: 70 |
| AAYHLVSQ, | SEQ ID NO: 71 |
| MDAFLESS, | SEQ ID NO: 72 |
| ESLPVVAV, | SEQ ID NO: 73 |
| SAPAVESE, | SEQ ID NO: 74 |
| DVAQFVLT, | SEQ ID NO: 75 |
| VAQFVLTE, | SEQ ID NO: 76 |
| AQFVLTEG, | SEQ ID NO: 77 |
| PVQPIGPQ, | SEQ ID NO: 78 |

What is claimed is:

1. A method of regulating bone formation comprising administering to a patient in need of such regulation a composition, wherein the composition binds glypican 4 (GPC4), and wherein the composition comprises a peptide having at least 80% identity to SEQ ID NO:42, or a conservative variant or fragment thereof.

2. The method of claim 1, wherein the peptide is set forth in SEQ ID NO:42.

3. The method of claim 1, wherein regulating bone formation comprises decreasing bone formation.

4. The method of claim 3, wherein decreasing bone formation comprises inhibiting osteoblast binding to osteoclast lacunae.

5. The method of claim 1, wherein regulating bone formation comprises increasing bone formation.

6. The method of claim 5, wherein increasing bone formation comprises increasing osteoblast binding to osteoclast lacunae.

7. The method of claim 6, wherein increasing bone formation comprises increasing osteoblast differentiation.

8. The method of claim 1, wherein the composition is administered systemically.

9. The method of claim 8, wherein the composition is administered intravenously or intra-arterially.

10. The method of claim 1, wherein the composition is administered by implanting on bone.

11. The method of claim 1, wherein the composition is administered to a patient having a bone related disorder.

12. The method of claim 11, wherein the disorder is type I postmenopausal osteoporosis; type II age-related osteoporosis; male osteoporosis; secondary osteoporosis due to steroid or pharmaceutical use, renal osteodystrophy, renal stones, juvenile idiopathic osteoporosis, hyperparathyroidism, hyperthyroidism, hypercalcemia's, Fanconi syndrome, sarcoidosis, diabetes, osteomalacia, vitamin D resistant rickets (VDRR), vitamin D dependent rickets (VDDR), and nutritional rickets, hypervitaminosis A and D, Paget's Disease, osteopetrosis, skeletal tumors, rheumatoid and osteo arthritis, osteogensis imperfecta, chondrodystrophies or sclerosing bone dysplasias.

13. The method of claim 11, wherein the disorder comprises heterotopic bone formation, osteophyte formation, diffuse idiopathic skeletal hyperostosis (DISH), or myositis ossificans progressiva (MOP).

14. The method of claim 1, wherein the composition binds SEQ ID NO: 38.

15. The method of claim 1, wherein the composition binds amino acids 252-263 of SEQ ID NO: 38.

16. A method of regulating bone formation comprising administering to a patient in need of such regulation a composition, wherein the composition binds with TGF-β receptor interacting protein (TRIP), and wherein the composition comprises a peptide having at least 80% identity to SEQ ID NO:42, or a conservative variant or fragment thereof.

17. The method of claim 16, wherein the peptide is set forth in SEQ ID NO:42.

18. A method of stimulating bone formation in a bone cell culture comprising administering a composition, wherein the composition binds glvpican 4 (GPC4), and wherein the composition comprises a peptide having at least 80% identity to SEQ ID NO:42, or a conservative variant or fragment thereof.

19. The method of claims 18, wherein the bone cell culture comprises osteoblast cells or osteoclast cells.

* * * * *

SEQUENCE LISTING

<160> NUMBER OF SEQ ID NOS: 78

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 1
cactctacta tgggttttac ggctccgccg cattat                              36

<210> SEQ ID NO 2

```
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 2
actatgggtt ttacggctcc gcggtttccg cattat                                 36

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 3
tctcagtggc atccgcggtc tgcgtcgtat ccgatg                                 36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 4
acgccgtctc ttcctccgac tatgtttcgg ttgact                                 36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 5
acgccgcttt cgtatctgaa gggtctggtg acggtg                                 36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 6
cggccacgga acaccagtag acgtcccatg cgcaga                                 36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 7
ataatgcgga aaccgcggag ccgtaaaacc catagt                                 36

<210> SEQ ID NO 8
<211> LENGTH: 36
```

```
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 8
cggccaacgg aacaccagta gacgtcccat gcgcag                              36

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 9
accaagcccc gaatcacgcg aataaagcgg ccaaga                              36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 10
cagagcctcc ttcgtccaat ttcacacact aagccc                              36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 11
ccgatcatac ataaccgaaa tcagatgaaa cggcag                              36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 12
catcttgcgc cgatgcctcg ggcgttgcat acgggt                              36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 13
gggcttagtg tgtgaaattg gacgaaggag gctctg                              36

<210> SEQ ID NO 14
<211> LENGTH: 36
<212> TYPE: DNA
```

```
<213> ORGANISM: Artificial Sequence
<220> FEATURE:
<223> OTHER INFORMATION: Description of Artificial Sequence:/note =
      Synthetic Construct

<400> SEQUENCE: 14
catcttgcgc cgatgcctcg ggcgttgcat acgggt                                36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 15
tttgtgaagc ctaaggcgct gtctctgcag gctgtg                                36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 16
tttcatgtga atccgacgtc tccgacgcat ccgttg                                36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 17
cagcatgcga atcatcaggc ttggaataat cttcgt                                36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 18
tttcatgtga atccgacgtc tccgacgcat ccgttg                                36

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 19

His Ser Thr Met Gly Phe Arg Ala Pro Pro His Tyr
 1               5                  10

<210> SEQ ID NO 20
<211> LENGTH: 12
<212> TYPE: PRT
```

```
<213> ORGANISM: Artificial Sequence
<220> FEATURE:
<223> OTHER INFORMATION: Description of Artificial Sequence:/note =
      Synthetic Construct

<400> SEQUENCE: 20

Thr Met Gly Phe Arg Ala Pro Arg Phe Pro His Tyr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 21

Ser Gln Trp His Pro Arg Ser Ala Ser Tyr Pro Met
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 22

Thr Pro Ser Leu Pro Pro Thr Met Phe Arg Leu Thr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 23

Thr Pro Leu Ser Tyr Leu Lys Gly Leu Val Thr Val
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 24

Ser Ala His Gly Thr Ser Thr Gly Val Pro Trp Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 25

Thr Met Gly Phe Arg Ala Pro Arg Phe Pro His Tyr
1               5                   10
```

```
<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 26

Leu Arg Met Gly Arg Leu Leu Val Phe Arg Trp Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 27

Ser Trp Pro Leu Tyr Ser Arg Asp Ser Gly Leu Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 28

Gly Leu Ser Val Glu Ile Gly Arg Arg Arg Leu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 29

Leu Pro Phe His Leu Ile Ser Val Met Tyr Asp Arg
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 30

His Leu Ala Pro Met Pro Arg Ala Leu His Thr Gly
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence:/note =
      Synthetic Construct
```

```
<400> SEQUENCE: 31

Gly Leu Ser Val Asn Trp Thr Lys Glu Ala Leu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 32

His Leu Ala Pro Met Pro Arg Ala Leu His Thr Gly
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 33

Phe Val Lys Pro Lys Ala Leu Ser Leu Gln Ala Val
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 34

Phe His Val Asn Pro Thr Ser Pro Thr His Pro Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 35

Gln His Ala Asn His Gln Ala Trp Asn Asn Leu Arg
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 36

Phe His Val Asn Pro Thr Ser Pro Thr His Pro Leu
1               5                   10

<210> SEQ ID NO 37
<211> LENGTH: 1926
```

<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 37

```
ccttctccct ccagctccac tcgctagtcc ccgactccgc cagccctcgg cccgctgccg      60
tagcgccgct tcccgtccgg tcccaaaggt gggaacgcgt ccgccccggc ccgcaccatg     120
gcacggttcg gcttgcccgc gcttctctgc accctggcag tgctcagcgc cgcgctgctg     180
gctgccgagc tcaagtcgaa aagttgctcg gaagtgcgca gtctttacgt gtccaaaggc     240
ttcaacaaga acgatgcccc cctccacgag atcaacggtg atcatttgaa gatctgtccc     300
cagggttcta cctgctgctc tcaagagatg gaggagaagt acagcctgca agtaaagat      360
gatttcaaaa gtgtggtcag cgaacagtgc aatcatttgc aagctgtctt tgcttcacgt     420
tacaagaagt ttgatgaatt cttcaaagaa ctacttgaaa atgcagagaa atccctgaat     480
gatatgtttg tgaagacata tggccattta acatgcaaa attctgagct atttaaagat      540
ctcttcgtag agttgaaacg ttactacgtg gtgggaaatg tgaacctgga gaatgctaa      600
atgacttctg ggctcgcctc ctggagcgga tgttccgcct ggtgaactcc cagtaccact     660
ttacagatga gtatctggaa tgtgtgagca agtatacgga gcagctgaag cccttcggag     720
atgtccctcg caaattgaag ctccaggtta ctcgtgcttt tgtagcagcc cgtactttcg     780
ctcaaggctt agcggttgcg ggagatgtcg tgagcaaggt ctccgtggta aacccccacag    840
cccagtgtac ccatgccctg ttgaagatga tctactgctc ccactgccgg ggtctcgtga     900
ctgtgaagcc atgttacaac tactgctcaa acatcatgag aggctgtttg gccaaccaag     960
gggatctcga ttttgaatgg aacaatttca tagatgctat gctgatggtg gcagagaggc    1020
tagagggtcc tttcaacatt gaatcggtca tggatcccat cgatgtgaag atttctgatg    1080
ctattatgaa catgcaggat aatagtgttc aagtgtctca gaaggttttc cagggatgtg    1140
gacccccaa gcccctccca gctggacgaa tttctcgttc catctctgaa agtgccttca     1200
gtgctcgctt cagaccacat caccccgagg aacgcccaac cacagcagct ggcactagtt    1260
tggaccgact ggttactgat gtcaaggaga actgaaaca ggccaagaaa ttctggtcct    1320
cccttccgag caacgtttgc aacgatgaga ggatggctgc aggaaacggc aatgaggatg    1380
actgttggaa tgggaaaggc aaaagcaggt acctgtttgc agtgacagga atggattag    1440
ccaaccaggg caacaaccca gaggtccagg ttgacaccag caaaccagac atactgatcc    1500
ttcgtcaaat catggctctt cgagtgatga ccagcaagat gaagaatgca tacaatggga    1560
acgacgtgga cttctttgat atcagtgatg aaagtagtgg agaaggaagt ggaagtggct    1620
gtgagtatca gcagtgccct tcagagtttg actacaatgc cactgaccat gctgggaaga    1680
gtgccaatga gaaagccgac agtgctggtg tccgtcctgg ggcacaggcc tacctcctca    1740
ctgtcttctg catcttgttc ctggttatgc agagagagtg gagataattc tcaaactctg    1800
agaaaaagtg ttcatcaaaa agttaaaagg caccagttat cacttttcta ccatcctagt    1860
gactttgctt tttaaatgaa tggacaacaa tgtacagttt ttactatgtg gccactggtt    1920
taagaa                                                                1926
```

<210> SEQ ID NO 38
<211> LENGTH: 556
<212> TYPE: PRT
<213> ORGANISM: Artificial Sequence

```
<220> FEATURE:
<223> OTHER INFORMATION: Description of Artificial Sequence:/note =
      Synthetic Construct

<400> SEQUENCE: 38
```

| | | | | | | | | | | | | | | |
|---|---|---|---|---|---|---|---|---|---|---|---|---|---|---|
| Met | Ala | Arg | Phe | Gly | Leu | Pro | Ala | Leu | Leu | Cys | Thr | Leu | Ala | Val | Leu |
| 1 | | | | 5 | | | | | 10 | | | | | 15 |
| Ser | Ala | Ala | Leu | Leu | Ala | Ala | Glu | Leu | Lys | Ser | Lys | Ser | Cys | Ser | Glu |
| | | | 20 | | | | | 25 | | | | | 30 | | |
| Val | Arg | Arg | Leu | Tyr | Val | Ser | Lys | Gly | Phe | Asn | Lys | Asn | Asp | Ala | Pro |
| | | 35 | | | | | 40 | | | | | 45 | | | |
| Leu | His | Glu | Ile | Asn | Gly | Asp | His | Leu | Lys | Ile | Cys | Pro | Gln | Gly | Ser |
| | 50 | | | | | 55 | | | | | 60 | | | | |
| Thr | Cys | Cys | Ser | Gln | Glu | Met | Glu | Glu | Lys | Tyr | Ser | Leu | Gln | Ser | Lys |
| 65 | | | | | 70 | | | | | 75 | | | | | 80 |
| Asp | Asp | Phe | Lys | Ser | Val | Val | Ser | Glu | Gln | Cys | Asn | His | Leu | Gln | Ala |
| | | | | 85 | | | | | 90 | | | | | 95 | |
| Val | Phe | Ala | Ser | Arg | Tyr | Lys | Lys | Phe | Asp | Glu | Phe | Phe | Lys | Glu | Leu |
| | | | | 100 | | | | | 105 | | | | | 110 | |
| Leu | Glu | Asn | Ala | Glu | Lys | Ser | Leu | Asn | Asp | Met | Phe | Val | Lys | Thr | Tyr |
| | | | 115 | | | | | 120 | | | | | 125 | | |
| Gly | His | Leu | Tyr | Met | Gln | Asn | Ser | Glu | Leu | Phe | Lys | Asp | Leu | Phe | Val |
| | 130 | | | | | 135 | | | | | 140 | | | | |
| Glu | Leu | Lys | Arg | Tyr | Tyr | Val | Val | Gly | Asn | Val | Asn | Leu | Glu | Glu | Met |
| 145 | | | | | 150 | | | | | 155 | | | | | 160 |
| Leu | Asn | Asp | Phe | Trp | Ala | Arg | Leu | Leu | Glu | Arg | Met | Phe | Arg | Leu | Val |
| | | | | 165 | | | | | 170 | | | | | 175 | |
| Asn | Ser | Gln | Tyr | His | Phe | Thr | Asp | Glu | Tyr | Leu | Glu | Cys | Val | Ser | Lys |
| | | | 180 | | | | | 185 | | | | | 190 | | |
| Tyr | Thr | Glu | Gln | Leu | Lys | Pro | Phe | Gly | Asp | Val | Pro | Arg | Lys | Leu | Lys |
| | | | 195 | | | | | 200 | | | | | 205 | | |
| Leu | Gln | Val | Thr | Arg | Ala | Phe | Val | Ala | Ala | Arg | Thr | Phe | Ala | Gln | Gly |
| | 210 | | | | | 215 | | | | | 220 | | | | |
| Leu | Ala | Val | Ala | Gly | Asp | Val | Val | Ser | Lys | Val | Ser | Val | Val | Asn | Pro |
| 225 | | | | | 230 | | | | | 235 | | | | | 240 |
| Thr | Ala | Gln | Cys | Thr | His | Ala | Leu | Leu | Lys | Met | Ile | Tyr | Cys | Ser | His |
| | | | | 245 | | | | | 250 | | | | | 255 | |
| Cys | Arg | Gly | Leu | Val | Thr | Val | Lys | Pro | Cys | Tyr | Asn | Tyr | Cys | Ser | Asn |
| | | | 260 | | | | | 265 | | | | | 270 | | |
| Ile | Met | Arg | Gly | Cys | Leu | Ala | Asn | Gln | Gly | Asp | Leu | Asp | Phe | Glu | Trp |
| | | 275 | | | | | 280 | | | | | 285 | | | |
| Asn | Asn | Phe | Ile | Asp | Ala | Met | Leu | Met | Val | Ala | Glu | Arg | Leu | Glu | Gly |
| | 290 | | | | | 295 | | | | | 300 | | | | |
| Pro | Phe | Asn | Ile | Glu | Ser | Val | Met | Asp | Pro | Ile | Asp | Val | Lys | Ile | Ser |
| 305 | | | | | 310 | | | | | 315 | | | | | 320 |
| Asp | Ala | Ile | Met | Asn | Met | Gln | Asp | Asn | Ser | Val | Gln | Val | Ser | Gln | Lys |
| | | | | 325 | | | | | 330 | | | | | 335 | |
| Val | Phe | Gln | Gly | Cys | Gly | Pro | Pro | Lys | Pro | Leu | Pro | Ala | Gly | Arg | Ile |
| | | | 340 | | | | | 345 | | | | | 350 | | |
| Ser | Arg | Ser | Ile | Ser | Glu | Ser | Ala | Phe | Ser | Ala | Arg | Phe | Arg | Pro | His |
| | | 355 | | | | | 360 | | | | | 365 | | | |
| His | Pro | Glu | Glu | Arg | Pro | Thr | Thr | Ala | Ala | Gly | Thr | Ser | Leu | Asp | Arg |
| | 370 | | | | | 375 | | | | | 380 | | | | |
| Leu | Val | Thr | Asp | Val | Lys | Glu | Lys | Leu | Lys | Gln | Ala | Lys | Lys | Phe | Trp |

```
                385                 390                 395                 400
        Ser Ser Leu Pro Ser Asn Val Cys Asn Asp Glu Arg Met Ala Ala Gly
                        405                 410                 415

Asn Gly Asn Glu Asp Asp Cys Trp Asn Gly Lys Gly Lys Ser Arg Tyr
                        420                 425                 430

Leu Phe Ala Val Thr Gly Asn Gly Leu Ala Asn Gln Gly Asn Asn Pro
                        435                 440                 445

Glu Val Gln Val Asp Thr Ser Lys Pro Asp Ile Leu Ile Leu Arg Gln
                        450                 455                 460

Ile Met Ala Leu Arg Val Met Thr Ser Lys Met Lys Asn Ala Tyr Asn
        465                 470                 475                 480

Gly Asn Asp Val Asp Phe Phe Asp Ile Ser Asp Glu Ser Ser Gly Glu
                        485                 490                 495

Gly Ser Gly Ser Gly Cys Glu Tyr Gln Gln Cys Pro Ser Glu Phe Asp
                        500                 505                 510

Tyr Asn Ala Thr Asp His Ala Gly Lys Ser Ala Asn Glu Lys Ala Asp
                        515                 520                 525

Ser Ala Gly Val Arg Pro Gly Ala Gln Ala Tyr Leu Leu Thr Val Phe
                        530                 535                 540

Cys Ile Leu Phe Leu Val Met Gln Arg Glu Trp Arg
        545                 550                 555

<210> SEQ ID NO 39
<211> LENGTH: 1327
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 39
ggcacgaggt tgcggccttc ctcgcgtcac cgccgggatg aagccgatcc tactgcaggg      60
ccatgagcgg tccattacgc agattaagta taaccgcgaa ggagacctcc tctttactgt    120
ggccaaggac cctatcgtca atgtatggta ctctgtgaat ggtgagaggc tgggcaccta    180
catgggccat accggagctg tgtggtgtgt ggacgctgac tgggacacca agcatgtcct    240
cactggctca gctgacaaca gctgtcgtct ctgggactgt gaaacaggaa agcagctggc    300
ccttctcaag accaattcgg ctgtccggac ctgcggtttt gactttgggg caacatcat    360 catgttctcc acgacaagc agatgggcta ccagtgcttt gtgagctttt ttgacctgcg    420
ggatccgagc cagattgaca caatgagcc tacatgaag atcccttgca atgactctaa    480
aatcaccagt gctgtttggg gacccctggg ggagtgcatc atcgctggcc atgagagtgg    540
gagctcaacc agtatagtgc caagtctgga gaggtgttgg tgaatgttaa ggagcactcc    600
cggcagatca cgacatcca gttatccagg gacatgacca tgtttgtgac cgcgtccaag    660
gacaacacag ccaagctttt tgactccaca actcttgaac atcagaagac tttccggaca    720
gaacgtcctg tcaactcagc tgccctctcc ccaactatg accatgtggt cctgggcggt    780
ggtcaggaag ccatggatgt aaccacaacc tccaccagga ttgcaagtt tgaggccagg    840 ttcttccatt tggcctttga agaagagttt ggaagagtca aggtcactt tggacctatc    900 aacagtgttg ccttccatcc tgatggcaag agctacagca gcggcggcga agatggttac    960
gtccgtatcc attacttcga cccacagtac ttcgaatttg agtttgaggc ttaagaagct    1020
ggatctcctg ccgggcgtgg tggctcatgc ctgtaatccc accactttt tttaaggcag   1080
```

```
gcggatcacc tgaggtcagg agtttaagac cagcctgacc aacatggaga aactcgtctc   1140
tactaaaaat acaaaaatac aaaaattagc caggcatggt ggcacacgcc tatagtccca   1200
gctactcagg aggctgaggc aggagaatca cttgaaccca ggaggcatag gttgcagtga   1260
gctgagatca cgtcattgca ctccatcctg agccacaaga gcaaaactcc gtctcaaaaa   1320
aaaaaaa                                                              1327
```

<210> SEQ ID NO 40
<211> LENGTH: 325
<212> TYPE: PRT
<213> ORGANISM: Artificial Sequence
<220> FEATURE:
<223> OTHER INFORMATION: Description of Artificial Sequence:/note = Synthetic Construct

<400> SEQUENCE: 40

```
Met Lys Pro Ile Leu Leu Gln Gly His Glu Arg Ser Ile Thr Gln Ile
1               5                   10                  15

Lys Tyr Asn Arg Glu Gly Asp Leu Leu Phe Thr Val Ala Lys Asp Pro
            20                  25                  30

Ile Val Asn Val Trp Tyr Ser Val Asn Gly Glu Arg Leu Gly Thr Tyr
        35                  40                  45

Met Gly His Thr Gly Ala Val Trp Cys Val Asp Ala Asp Trp Asp Thr
    50                  55                  60

Lys His Val Leu Thr Gly Ser Ala Asp Asn Ser Cys Arg Leu Trp Asp
65                  70                  75                  80

Cys Glu Thr Gly Lys Gln Leu Ala Leu Leu Lys Thr Asn Ser Ala Val
                85                  90                  95

Arg Thr Cys Gly Phe Asp Phe Gly Gly Asn Ile Ile Met Phe Ser Thr
            100                 105                 110

Asp Lys Gln Met Gly Tyr Gln Cys Phe Val Ser Phe Asp Leu Arg
        115                 120                 125

Asp Pro Ser Gln Ile Asp Asn Asn Glu Pro Tyr Met Lys Ile Pro Cys
130                 135                 140

Asn Asp Ser Lys Ile Thr Ser Ala Val Trp Gly Pro Leu Gly Glu Cys
145                 150                 155                 160

Ile Ile Ala Gly His Glu Ser Gly Glu Leu Asn Gln Tyr Ser Ala Lys
                165                 170                 175

Ser Gly Glu Val Leu Val Asn Val Lys Glu His Ser Arg Gln Ile Asn
            180                 185                 190

Asp Ile Gln Leu Ser Arg Asp Met Thr Met Phe Val Thr Ala Ser Lys
        195                 200                 205

Asp Asn Thr Ala Lys Leu Phe Asp Ser Thr Thr Leu Glu His Gln Lys
    210                 215                 220

Thr Phe Arg Thr Glu Arg Pro Val Asn Ser Ala Ala Leu Ser Pro Asn
225                 230                 235                 240

Tyr Asp His Val Val Leu Gly Gly Gln Glu Ala Met Asp Val Thr
                245                 250                 255

Thr Thr Ser Thr Arg Ile Gly Lys Phe Glu Ala Arg Phe Phe His Leu
            260                 265                 270

Ala Phe Glu Glu Glu Phe Gly Arg Val Lys Gly His Phe Gly Pro Ile
        275                 280                 285

Asn Ser Val Ala Phe His Pro Asp Gly Lys Ser Tyr Ser Ser Gly Gly
    290                 295                 300

Glu Asp Gly Tyr Val Arg Ile His Tyr Phe Asp Pro Gln Tyr Phe Glu
```

Phe Glu Phe Glu Ala
              325

<210> SEQ ID NO 41
<211> LENGTH: 1415
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 41

| | | | | | |
|---|---|---|---|---|---|
| agggaataaa | ggctcaggga | ccggcagttc | tactctagag | cccaccagcc | tctcagagcc | 60 |
| tccggtgact | ggcctgtgtc | tccccctgga | tggacatgtg | gacggcgctg | ctcatcctgc | 120 |
| aagccttgtt | gctaccctcc | ctggctgatg | gtgccacccc | tgccctgcgc | tttgtagccg | 180 |
| tgggtgactg | gggaggggtc | cccaatgccc | cattccacac | ggcccgggaa | atggccaatg | 240 |
| ccaaggagat | cgctcggact | gtgcagatcc | tgggtgcaga | cttcatcctg | tctctagggg | 300 |
| acaatttta | cttcactggt | gtgcaagaca | tcaatgacaa | gaggttccag | agacctttg | 360 |
| aggacgtatt | ctctgaccgc | tcccttcgca | agtgccctg | gtacgtgcta | gccggaaacc | 420 |
| atgaccacct | tggcaatgtc | tctgcccaga | ttgcatactc | taagatctcc | aagcgctgga | 480 |
| acttccccag | cccttttctac | cgcctgcact | tcaagatccc | acagaccaat | gtgtctgtgg | 540 |
| ccattttat | gctggacaca | gtgacactat | gtggcaactc | agatgacttc | ctcagccagc | 600 |
| agcctgagag | gccccgagac | gtgaagctgg | cccgcacaca | gctgtcctgg | ctcaagaaac | 660 |
| agctggcggc | ggccagggag | gactacgtgc | tggtggctgg | ccactacccc | gtgtggtcca | 720 |
| tagccgagca | cggccctacc | cactgcctgg | tcaagcagct | acggccactg | ctggccacat | 780 |
| acggggtcac | tgcctacctg | tgcggccacg | atcacaatct | gcagtacctg | caagatgaga | 840 |
| atggcgtggg | ctacgtgctg | agtggggctg | ggaatttcat | ggaccctca | aagcggcacc | 900 |
| agcgcaaggt | ccccaacggc | tatctgcgct | tccactatgg | gactgaagac | tcactgggtg | 960 |
| gctttgccta | tgtggagatc | agctccaaag | agatgactgt | cacttacatc | gaggcctcgg | 1020 |
| gcaagtccct | ctttaagacc | aggctgccga | ggcgagccag | gccctgaact | cccatgactg | 1080 |
| cccagctctg | aggcccgatc | tccactgttg | ggtgggtggg | ccctgccggg | accctgctca | 1140 |
| caggcaggct | tttcctccaa | cctgtggcgc | tgcagcaggg | caggaagggg | aaacacagct | 1200 |
| gatgaactgt | ggtgccacat | gacccttgtg | gcacagatgc | ccacgtatgt | gaaacacaca | 1260 |
| tggacatgtg | tcccagccac | agtgttatgc | tctgtggctg | gctcacctt | gctgagttcc | 1320 |
| ggggtgcaat | gggggaggga | gggagggaaa | gcttcctcct | aaatcaagca | tctttctgtt | 1380 |
| actgatgttc | aataaaagaa | tagttgccaa | ggctg | | | 1415 |

<210> SEQ ID NO 42
<211> LENGTH: 325
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 42

Met Asp Met Trp Thr Ala Leu Leu Ile Leu Gln Ala Leu Leu Leu Pro
1               5                   10                  15

Ser Leu Ala Asp Gly Ala Thr Pro Ala Leu Arg Phe Val Ala Val Gly

-continued

```
                    20                  25                  30
Asp Trp Gly Gly Val Pro Asn Ala Pro Phe His Thr Ala Arg Glu Met
         35                  40                  45
Ala Asn Ala Lys Glu Ile Ala Arg Thr Val Gln Ile Leu Gly Ala Asp
     50                  55                  60
Phe Ile Leu Ser Leu Gly Asp Asn Phe Tyr Phe Thr Gly Val Gln Asp
 65                  70                  75                  80
Ile Asn Asp Lys Arg Phe Gln Glu Thr Phe Glu Asp Val Phe Ser Asp
                 85                  90                  95
Arg Ser Leu Arg Lys Val Pro Trp Tyr Val Leu Ala Gly Asn His Asp
            100                 105                 110
His Leu Gly Asn Val Ser Ala Gln Ile Ala Tyr Ser Lys Ile Ser Lys
        115                 120                 125
Arg Trp Asn Phe Pro Ser Pro Phe Tyr Arg Leu His Phe Lys Ile Pro
    130                 135                 140
Gln Thr Asn Val Ser Val Ala Ile Phe Met Leu Asp Thr Val Thr Leu
145                 150                 155                 160
Cys Gly Asn Ser Asp Asp Phe Leu Ser Gln Gln Pro Glu Arg Pro Arg
                165                 170                 175
Asp Val Lys Leu Ala Arg Thr Gln Leu Ser Trp Leu Lys Lys Gln Leu
            180                 185                 190
Ala Ala Ala Arg Glu Asp Tyr Val Leu Val Ala Gly His Tyr Pro Val
        195                 200                 205
Trp Ser Ile Ala Glu His Gly Pro Thr His Cys Leu Val Lys Gln Leu
    210                 215                 220
Arg Pro Leu Leu Ala Thr Tyr Gly Val Thr Ala Tyr Leu Cys Gly His
225                 230                 235                 240
Asp His Asn Leu Gln Tyr Leu Gln Asp Glu Asn Gly Val Gly Tyr Val
                245                 250                 255
Leu Ser Gly Ala Gly Asn Phe Met Asp Pro Ser Lys Arg His Gln Arg
            260                 265                 270
Lys Val Pro Asn Gly Tyr Leu Arg Phe His Tyr Gly Thr Glu Asp Ser
        275                 280                 285
Leu Gly Gly Phe Ala Tyr Val Glu Ile Ser Ser Lys Glu Met Thr Val
    290                 295                 300
Thr Tyr Ile Glu Ala Ser Gly Lys Ser Leu Phe Lys Thr Arg Leu Pro
305                 310                 315                 320
Arg Arg Ala Arg Pro
            325

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 43
acaccgcttt cgtatctgaa gggtctggtg acggtg                                  36

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence:/note =
```

-continued

Synthetic Construct

<400> SEQUENCE: 44

Thr Pro Leu Ser Tyr Leu Lys Gly Leu Val Thr Ile
1               5                   10

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 45
acaccgcttt cgtatctgaa gggtctggtg acgata                                  36

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 46
actccgcttt cgtatctgaa gggtctggtg acgata                                  36

<210> SEQ ID NO 47
<211> LENGTH: 1670
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 47

```
atggcacggt tcggattgcc cgcgcttctc tgcaccctgg cagtgctcag cgccgcgctg        60
ctggctgccg agctcaagtc gaaaagttgc tcggaagtgc gacgtcttta cgtgtccaaa       120
ggcttcaaca agaacgatgc cccctccac gagatcaacg gtgatcattt gaagatctgt        180
ccccagggtt ctacctgctg ctctcaagag atggaggaga agtacagcct gcaaagtaaa       240
gatgatttca aaagtgtggt cagcgaacag tgcaatcatt gcaagctgt ctttgcttca        300 cgttacaaga agtttgatga attcttcaaa gaactacttg aaaatgcaga gaaatccctg       360
aatgatatgt ttgtgaagac atatggccat ttatacatgc aaaattctga gctatttaaa      420
gatctcttcg tagagttgaa acgttactac gtggtgggaa atgtgaacct ggaagaaatg       480
ctaaatgact tctgggctcg cctcctggag cggatgttcc gcctggtgaa ctcccagtac       540
cactttacag atgagtatct ggaatgtgtg agcaagtata cggagcagct gaagcccttc       600
ggagatgtcc ctcgcaaatt gaagctccag gttactcgtg cttttgtagc agcccgtact      660
ttcgctcaag gcttagcggt tgcgggagat gtcgtgagca aggtctccgt ggtaaacccc      720
acagcccagt gtacccatgc cctgttgaag atgatctact gctcccactg ccggggtctc      780
gtgactgtga agccatgtta caactactgc tcaaacatca tgagaggctg tttggccaac      840 caagggggatc tcgattttga atggaacaat ttcatagatg ctatgctgat ggtggcagag      900
aggctagagg gtcctttcaa cattgaatcg gtcatggatc ccatcgatgt gaagatttct      960
gatgctatta tgaacatgca ggataatagt gttcaagtgt ctcagaaggt tttccaggga     1020
tgtggacccc ccaagccct cccagctgga cgaatttctc gttccatctc tgaaagtgcc     1080
```

-continued

```
ttcagtgctc gcttcagacc acatcacccc gaggaacgcc caaccacagc agctggcact    1140
agtttggacc gactggttac tgatgtcaag gagaaactga acaggccaa gaaattctgg    1200
tcctcccttc cgagcaacgt ttgcaacgat gagaggatgg ctgcaggaaa cggcaatgag    1260
gatgactgtt ggaatgggaa aggcaaaagc aggtacctgt ttgcagtgac aggaaatgga    1320
ttagccaacc agggcaacaa cccagaggtc caggttgaca ccagcaaacc agacatactg    1380
atccttcgtc aaatcatggc tcttcgagtg atgaccagca agatgaagaa tgctacaatg    1440
ggaacgacgt ggacttcttt gatatcagtg atgaaagtag tggagaagga agtggaagtg    1500
gctgtgagta tcagcagtgc ccttcagagt ttgactacaa tgccactgac catgctggga    1560
agagtgccaa tgagaaagcc gacagtgctg gtgtccgtcc tggggcacag gcctacctcc    1620
tcactgtctt ctgcatcttg ttcctggtta tgcagagaga gtggagataa              1670
```

<210> SEQ ID NO 48
<211> LENGTH: 556
<212> TYPE: PRT
<213> ORGANISM: Artificial Sequence
<220> FEATURE:
<223> OTHER INFORMATION: Description of Artificial Sequence:/note =
    Synthetic Construct

<400> SEQUENCE: 48

```
Met Ala Arg Phe Ala Leu Pro Ala Leu Leu Cys Thr Leu Ala Val Leu
 1               5                  10                  15

Ser Ala Ala Leu Leu Ala Ala Glu Leu Lys Ser Lys Ser Cys Ser Glu
             20                  25                  30

Val Arg Arg Leu Tyr Val Ser Lys Gly Phe Asn Lys Asn Asp Ala Pro
         35                  40                  45

Leu His Glu Ile Asn Gly Asp His Leu Lys Ile Cys Pro Gln Gly Ser
     50                  55                  60

Thr Cys Cys Ser Gln Glu Met Glu Glu Lys Tyr Ser Leu Gln Ser Lys
 65                  70                  75                  80

Asp Asp Phe Lys Ser Val Val Ser Glu Gln Cys Asn His Leu Gln Ala
                 85                  90                  95

Val Phe Ala Ser Arg Tyr Lys Lys Phe Asp Glu Phe Phe Lys Glu Leu
            100                 105                 110

Leu Glu Asn Ala Glu Lys Ser Leu Asn Asp Met Phe Val Lys Thr Tyr
        115                 120                 125

Gly His Leu Tyr Met Gln Asn Ser Glu Leu Phe Lys Asp Leu Phe Val
    130                 135                 140

Glu Leu Lys Arg Tyr Tyr Val Val Gly Asn Val Asn Leu Glu Glu Met
145                 150                 155                 160

Leu Asn Asp Phe Trp Ala Arg Leu Leu Glu Arg Met Phe Arg Leu Val
                165                 170                 175

Asn Ser Gln Tyr His Phe Thr Asp Glu Tyr Leu Glu Cys Val Ser Lys
            180                 185                 190

Tyr Thr Glu Gln Leu Lys Pro Phe Gly Asp Val Pro Arg Lys Leu Lys
        195                 200                 205

Leu Gln Val Thr Arg Ala Phe Val Ala Ala Arg Thr Phe Ala Gln Gly
    210                 215                 220

Leu Ala Val Ala Gly Asp Val Val Ser Lys Val Ser Val Val Asn Pro
225                 230                 235                 240

Thr Ala Gln Cys Thr His Ala Leu Leu Lys Met Ile Tyr Cys Ser His
                245                 250                 255
```

```
Cys Arg Gly Leu Val Thr Val Lys Pro Cys Tyr Asn Tyr Cys Ser Asn
            260                 265                 270
Ile Met Arg Gly Cys Leu Ala Asn Gln Gly Asp Leu Asp Phe Glu Trp
            275                 280                 285
Asn Asn Phe Ile Asp Ala Met Leu Met Val Ala Glu Arg Leu Glu Gly
            290                 295                 300
Pro Phe Asn Ile Glu Ser Val Met Asp Pro Ile Asp Val Lys Ile Ser
305                 310                 315                 320
Asp Ala Ile Met Asn Met Gln Asp Asn Ser Val Gln Val Ser Gln Lys
                325                 330                 335
Val Phe Gln Gly Cys Gly Pro Pro Lys Pro Leu Pro Ala Gly Arg Ile
            340                 345                 350
Ser Arg Ser Ile Ser Glu Ser Ala Phe Ser Ala Arg Phe Arg Pro His
            355                 360                 365
His Pro Glu Glu Arg Pro Thr Thr Ala Gly Thr Ser Leu Asp Arg
            370                 375                 380
Leu Val Thr Asp Val Lys Glu Lys Leu Lys Gln Ala Lys Lys Phe Trp
385                 390                 395                 400
Ser Ser Leu Pro Ser Asn Val Cys Asn Asp Glu Arg Met Ala Ala Gly
            405                 410                 415
Asn Gly Asn Glu Asp Asp Cys Trp Asn Gly Lys Gly Lys Ser Arg Tyr
            420                 425                 430
Leu Phe Ala Val Thr Gly Asn Gly Leu Ala Asn Gln Gly Asn Asn Pro
            435                 440                 445
Glu Val Gln Val Asp Thr Ser Lys Pro Asp Ile Leu Ile Leu Arg Gln
            450                 455                 460
Ile Met Ala Leu Arg Val Met Thr Ser Lys Met Lys Asn Ala Tyr Asn
465                 470                 475                 480
Gly Asn Asp Val Asp Phe Phe Asp Ile Ser Asp Glu Ser Ser Gly Glu
            485                 490                 495
Gly Ser Gly Ser Gly Cys Glu Tyr Gln Gln Cys Pro Ser Glu Phe Asp
            500                 505                 510
Tyr Asn Ala Thr Asp His Ala Gly Lys Ser Ala Asn Glu Lys Ala Asp
            515                 520                 525
Ser Ala Gly Val Arg Pro Gly Ala Gln Ala Tyr Leu Leu Thr Val Phe
            530                 535                 540
Cys Ile Leu Phe Leu Val Met Gln Arg Glu Trp Arg
545                 550                 555
```

<210> SEQ ID NO 49
<211> LENGTH: 1671
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 49

```
atggcacggt tcgccttgcc cgcgcttctc tgcaccctgg cagtgctcag cgccgcgctg      60
ctggctgccg agctcaagtc gaaaagttgc tcggaagtgc gacgtcttta cgtgtccaaa     120
ggcttcaaca agaacgatgc ccccctccac gagatcaacg tgatcatttg aagatctgt     180 ccccagggtt ctacctgctg ctctcaagag atggaggaga agtacagcct gcaaagtaaa     240
gatgatttca aaagtgtggt cagcgaacag tgcaatcatt gcaagctgt ctttgcttca     300
```

```
cgttacaaga agtttgatga attcttcaaa gaactacttg aaaatgcaga gaaatccctg        360
aatgatatgt ttgtgaagac atatggccat ttatacatgc aaaattctga gctatttaaa        420
gatctcttcg tagagttgaa acgttactac gtggtgggaa atgtgaacct ggaagaaatg        480
ctaaatgact tctgggctcg cctcctggag cggatgttcc gcctggtgaa ctcccagtac        540
cactttacag atgagtatct ggaatgtgtg agcaagtata cggagcagct gaagcccttc        600
ggagatgtcc ctcgcaaatt gaagctccag gttactcgtg cttttgtagc agcccgtact        660
ttcgctcaag gcttagcggt tgcgggagat gtcgtgagca aggtctccgt ggtaaacccc        720
acagcccagt gtacccatgc cctgttgaag atgatctact gctcccactg ccggggtctc        780
gtgactgtga agccatgtta caactactgc tcaaacatca tgagaggctg tttggccaac        840 caagggatc tcgattttga atggaacaat ttcatagatg ctatgctgat ggtggcagag        900
aggctagagg gtcctttcaa cattgaatcg tcatggatcc catcgatgt gaagatttct        960 gatgctatta tgaacatgca ggataatagt gttcaagtgt ctcagaaggt tttccaggga       1020
tgtggacccc ccaagcccct cccagctgga cgaatttctc gttccatctc tgaaagtgcc       1080
ttcagtgctc gcttcagacc acatcacccc gaggaacgcc caaccacagc agctggcact       1140
agtttggacc gactggttac tgatgtcaag gagaaactga acaggccaa gaaattctgg        1200 tcctcccttc cgagcaacgt ttgcaacgat gagaggatgg ctgcaggaaa cggcaatgag       1260
gatgactgtt ggaatgggaa aggcaaaagc aggtacctgt ttgcagtgac aggaaatgga       1320
ttagccaacc agggcaacaa cccagaggtc caggttgaca ccagcaaacc agacatactg       1380
atccttcgtc aaatcatggc tcttcgagtg atgaccagca agatgaagaa tgcatacaat       1440
gggaacgacg tggacttctt tgatatcagt gatgaaagta gtggagaagg aagtggaagt       1500
ggctgtgagt atcagcagtg cccttcagag tttgactaca atgccactga ccatgctggg       1560
aagagtgcca atgagaaagc cgacagtgct ggtgtccgtc ctggggcaca ggcctacctc       1620
ctcactgtct tctgcatctt gttcctggtt atgcagagag agtggagata a              1671

<210> SEQ ID NO 50
<211> LENGTH: 1671
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 50
atggcacggt tcgcattgcc cgcgcttctc tgcaccctgg cagtgctcag cgccgcgctg         60
ctggctgccg agctcaagtc gaaaagttgc tcggaagtgc gacgtcttta cgtgtccaaa        120
ggcttcaaca agaacgatgc cccctccac gagatcaacg tgatcatttt gaagatctgt        180
cccccagggt ctacctgctg ctctcaagag atggaggaga gtacagcct gcaaagtaaa         240 gatgatttca aagtgtggt cagcgaacag tgcaatcatt gcaagctgt cttttgcttca       300 cgttacaaga agtttgatga attcttcaaa gaactacttg aaaatgcaga gaaatccctg       360
aatgatatgt ttgtgaagac atatggccat ttatacatgc aaaattctga gctatttaaa       420
gatctcttcg tagagttgaa acgttactac gtggtgggaa atgtgaacct ggaagaaatg       480
ctaaatgact tctgggctcg cctcctggag cggatgttcc gcctggtgaa ctcccagtac       540
cactttacag atgagtatct ggaatgtgtg agcaagtata cggagcagct gaagcccttc       600
ggagatgtcc ctcgcaaatt gaagctccag gttactcgtg cttttgtagc agcccgtact       660
```

```
ttcgctcaag gcttagcggt tgcgggagat gtcgtgagca aggtctccgt ggtaaacccc    720
acagcccagt gtacccatgc cctgttgaag atgatctact gctcccactg ccgggtctc    780 gtgactgtga agccatgtta caactactgc tcaaacatca tgagaggctg tttggccaac    840 caagggatc tcgattttga atggaacaat ttcatagatg ctatgctgat ggtggcagag    900
aggctagagg gtccttcaa cattgaatcg gtcatggatc ccatcgatgt gaagatttct    960
gatgctatta tgaacatgca ggataatagt gttcaagtgt ctcagaaggt tttccaggga   1020
tgtggacccc ccaagcccct cccagctgga cgaatttctc gttccatctc tgaaagtgcc   1080
ttcagtgctc gcttcagacc acatcacccc gaggaacgcc caaccacagc agctggcact   1140
agtttggacc gactggttac tgatgtcaag gagaaactga acaggccaa gaaattctgg   1200 tcctcccttc cgagcaacgt ttgcaacgat gagaggatgg ctgcaggaaa cggcaatgag   1260
gatgactgtt ggaatgggaa aggcaaaagc aggtacctgt ttgcagtgac aggaaatgga   1320
ttagccaacc agggcaacaa cccagaggtc caggttgaca ccagcaaacc agacatactg   1380
atccttcgtc aaatcatggc tcttcgagtg atgaccagca agatgaagaa tgcatacaat   1440
gggaacgacg tggacttctt tgatatcagt gatgaaagta gtggagaagg aagtggaagt   1500
ggctgtgagt atcagcagtg cccttcagag tttgactaca atgccactga ccatgctggg   1560
aagagtgcca atgagaaagc cgacagtgct ggtgtccgtc ctgggcaca ggcctacctc   1620 ctcactgtct tctgcatctt gttcctggtt atgcagagag agtggagata a            1671
```

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 51

Pro Arg Phe Lys Ile Ile Gly Gly
  1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 52

Pro Arg Phe Arg Ile Ile Gly Gly
  1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 53

Ser Ser Arg His Arg Arg Ala Leu Asp
  1               5

<210> SEQ ID NO 54
<211> LENGTH: 14

```
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 54

Arg Lys Ser Ser Ile Ile Ile Arg Met Arg Asp Val Val Leu
 1               5                  10

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 55

Ser Ser Ser Phe Asp Lys Gly Lys Tyr Lys Lys Gly Asp Asp Ala
 1               5                  10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 56

Ser Ser Ser Phe Asp Lys Gly Lys Tyr Lys Arg Gly Asp Asp Ala
 1               5                  10                  15

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 57

Ile Glu Gly Arg
 1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 58

Ile Asp Gly Arg
 1

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 59

Gly Gly Ser Ile Asp Gly Arg
```

```
<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 60

Pro Leu Gly Leu Trp Ala
 1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 61

Gly Pro Gln Gly Ile Ala Gly Gln
 1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 62

Gly Pro Gln Gly Leu Leu Gly Ala
 1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 63

Gly Ile Ala Gln Gln
 1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 64

Gln Pro Leu Gly Ile Ala Gly Ile
 1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence:/note =
```

-continued

Synthetic Construct

<400> SEQUENCE: 65

Gly Pro Glu Gly Leu Arg Val Gly
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 66

Tyr Gly Ala Gly Leu Gly Val Val
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 67

Ala Gly Leu Gly Val Val Glu Arg
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 68

Ala Gly Leu Gly Ile Ser Ser Thr
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 69

Glu Pro Gln Ala Leu Ala Met Ser
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 70

Gln Ala Leu Ala Met Ser Ala Ile
1               5

<210> SEQ ID NO 71

```
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 71

Ala Ala Tyr His Leu Val Ser Gln
 1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 72

Met Asp Ala Phe Leu Glu Ser Ser
 1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 73

Glu Ser Leu Pro Val Val Ala Val
 1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 74

Ser Ala Pro Ala Val Glu Ser Glu
 1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 75

Asp Val Ala Gln Phe Val Leu Thr
 1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 76
```

```
Val Ala Gln Phe Val Leu Thr Glu
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 77

Ala Gln Phe Val Leu Thr Glu Gly
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 78

Pro Val Gln Pro Ile Gly Pro Gln
1               5
```